(12) United States Patent
Rohlff

(10) Patent No.: US 8,652,478 B2
(45) Date of Patent: Feb. 18, 2014

(54) METHOD FOR TREATING CANCER BY ADMINISTERING ANTIBODY TO EPHRIN TYPE-A RECEPTOR 7

(75) Inventor: Christian Rohlff, Abingdon (GB)

(73) Assignee: Oxford Biotherapeutics Ltd., Oxon (GB)

( * ) Notice: Subject to any disclaimer, the term of this patent is extended or adjusted under 35 U.S.C. 154(b) by 0 days.

(21) Appl. No.: 12/997,204

(22) PCT Filed: Jun. 9, 2009

(86) PCT No.: PCT/IB2009/005884
§ 371 (c)(1),
(2), (4) Date: Apr. 15, 2011

(87) PCT Pub. No.: WO2009/150513
PCT Pub. Date: Dec. 17, 2009

(65) Prior Publication Data
US 2011/0195074 A1    Aug. 11, 2011

Related U.S. Application Data

(60) Provisional application No. 61/060,067, filed on Jun. 9, 2008.

(51) Int. Cl.
*A61K 39/395* (2006.01)
*A61K 39/00* (2006.01)

(52) U.S. Cl.
USPC .................................... 424/158.1; 424/277.1

(58) Field of Classification Search
None
See application file for complete search history.

(56) References Cited

U.S. PATENT DOCUMENTS

| | | | |
|---|---|---|---|
| 5,981,245 | A | 11/1999 | Fox et al. |
| 5,981,246 | A | 11/1999 | Fox et al. |
| 6,300,482 | B1 | 10/2001 | Ciossek et al. |
| 6,812,339 | B1 | 11/2004 | Venter et al. |
| 6,992,175 | B1 | 1/2006 | Fox et al. |
| 7,034,112 | B2 | 4/2006 | Ciossek et al. |
| 7,473,531 | B1 | 1/2009 | Domon et al. |
| 7,659,374 | B2 | 2/2010 | Wu et al. |
| 2006/0121042 | A1 | 6/2006 | Dall'Acqua et al. |

FOREIGN PATENT DOCUMENTS

| | | |
|---|---|---|
| EP | 1464706 A | 10/2004 |
| EP | 1662259 A | 5/2006 |
| WO | 2004/081180 A | 9/2004 |
| WO | WO 2005/042006 | 5/2005 |
| WO | 2006/023403 A | 3/2006 |
| WO | WO 2006/085684 | 8/2006 |
| WO | 2008/126002 A | 10/2008 |
| WO | WO 2009/028581 | 3/2009 |

OTHER PUBLICATIONS

Figueroa, Johnny D., et al., "Inhibition of EphA7 Up-Regulation after Spinal Cord Injury Reduces Apoptosis and Promotes Locomotor Recovery," J. of Neuroscience Research, v. 84, n. 7, p. 1438-1451, Nov. 15, 2006.

Hafner, Christian, et al., "Differential Gene Expression of Eph Receptors and Ephrins in Benign Human Tissues and Cancers," Clinical Chemistry, v. 50, No. 3, p. 490-499, Mar. 1, 2004.

Holmberg, J. et al., "Regulation of Repulsion Versus Adhesion by Different Splice Forms of an Eph Receptor," Nature, v. 408, n. 6809, p. 203-206, Nov. 9, 2000.

Kao H-W et al., "Tyrosine-Kinase Expression Profiles in Human Gastric Caner Cell Lines and Therir Modulations with Retinoic Acids," British J. of Cancer, v. 88, n. 7, p. 1058-1064, Apr. 7, 2003.

Lin, K-Y et al., "Overexpression of Protein Kinase Calpha mRNA may be an Indepeendent Prognostic Marker for Gastric Carcinoma," J. of Surgical Oncology, v. 97, n. 6, p. 538-543, May 1, 2008.

Nakamura, R. et al., "EPHA2/EFNA1 Expression in Human Gastric Cancer," Cancer Science, v. 96, n. 1, p. 42-47, Jan. 2005.

Surawska, H. et al., "The Role of Ephrins and Eph Receptors in Cancer," Cytokine and Growth Factor Reviews, v. 15, n. 6, p. 430, Dec. 1, 2004.

Wang, Lin-Fang, et al., "Increased Expression of EphA7 Correlates with Adverse Outcome in Primary and Recurrent Glioblastoma Multiforme patients," BMC Cancer, v. 8, n. 1, p. 79, Mar. 25, 2008.

Wang, J. et al, "Differential Expression of EphA7 Receptor Tyrosine Kinase in Gastric Carcinoma," Human Pathology, v. 38, n. 11, p. 1649-1656, Nov. 2007.

Wimmer-Kleikamp, S., "Eph-Modulated Cell Morphology, Adhesion and Motility in Carcinogenesis," Life, v. 57, n. 6, p. 421-431, Jun. 2005.

Aasheim HC, et al., "Regulated expression of the Eph-related receptor tyrosine kinase Hek11 in early human B lymphopoiesis.", Blood, 1997, pp. 3613-3622, vol. 90, No. 9.

Alavizadeh A, et al., "The Wheels mutation in the mouse causes vascular, hindbrain, and inner ear defects.", Dev. Biol., 2001, pp. 244-260, vol. 234, No. 1.

Alvarez IS, et al., "Neural induction in whole chick embryo cultures by FGF.", Dev. Biol., 1998, pp. 42-54, vol. 199, No. 1.

Araujo M, et al., "The expression and regulation of chick EphA7 suggests roles in limb patterning and innervation.", Development, 1998, pp. 4195-4204, vol. 125, No. 21.

Araujo M, et al., "The expression of chick EphA7 during segmentation of the central and peripheral nervous system.", Mech. Dev., 1997, pp. 173-177, vol. 68, Nos. 1-2.

Bianchi LM, et al., "EphB receptors influence growth of ephrin-B1-positive statoacoustic nerve fibers.", Eur. J. Neurosci., 2002, pp. 1499-1506, vol. 16, No. 8.

(Continued)

*Primary Examiner* — Robert Landsman
(74) *Attorney, Agent, or Firm* — Morgan, Lewis & Bockius LLP

(57) ABSTRACT

The present invention provides methods and compositions for treatment, screening, diagnosis and prognosis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, for monitoring the effectiveness of treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, and for drug development.

13 Claims, 8 Drawing Sheets

(56) References Cited

OTHER PUBLICATIONS

Bianchi LM, et al., "Comparison of ephrin-A ligand and EphA receptor distribution in the developing inner ear.", Anat. Rec., 1999, pp. 127-134, vol. 254, No. 1.

Bishop KM, et al., "Distinct actions of Emx1, Emx2, and Pax6 in regulating the specification of areas in the developing neocortex.", J. Neurosci., 2002, pp. 7627-7638, vol. 22, No. 17.

Blanco MJ, et al., "Expression of EphA receptors and ligands during chick cerebellar development.", Mech. Dev., 2002, pp. 225-229, vol. 114, Nos. 1-2.

Caronia G, et al., "An I47L substitution in the HOXD13 homeodomain causes a novel human limb malformation by producing a selective loss of function.", Development, 2003, pp. 1701-1712, vol. 130, No. 8.

Ciossek T, et al., "Segregation of the receptor EphA7 from its tyrosine kinase-negative isoform on neurons in adult mouse brain.", Brain Res. Mol. Brain Res., 1999, pp. 231-236, vol. 74, issues 1-2.

Connor RJ, et al., "Expression and tyrosine phosphorylation of Eph receptors suggest multiple mechanisms in patterning of the visual system.", Dev. Biol., 1998, pp. 21-35, vol. 193, No. 1.

Dawson DW, et al., "Global DNA methylation profiling reveals silencing of a secreted form of Epha7 in mouse and human germinal center B-cell lymphomas.", Oncogene, 2007, pp. 4243-4252, vol. 26, No. 29.

De Saint-Vis B, et al., "Human dendritic cells express neuronal Eph receptor tyrosine kinases: role of EphA2 in regulating adhesion to fibronectin.", Blood, 2003, pp. 4431-4440, vol. 102, No. 13.

Depaepe V, et al., "Ephrin signalling controls brain size by regulating apoptosis of neural progenitors.", Nature, 2005, pp. 1244-1250, vol. 435, No. 7046.

Donoghue MJ, et al., "Molecular evidence for the early specification of presumptive functional domains in the embryonic primate cerebral cortex.", J. Neurosci., 1999, pp. 5967-5979, vol. 19, No. 14.

Feng W, et al., "Morphoproteomic Profile of mTOR, Ras/Raf Kinase/ERK, and NF-kappaB Pathways in Human Gastric Adenocarcinoma.", Ann. Clin. Lab. Sci., 2008, pp. 195-209, vol. 38, No. 3.

Foster RE, et al., "Characterization of a 3;6 translocation associated with renal cell carcinoma.", Genes Chromosomes Cancer, 2007, pp. 311-317, vol. 46, No. 4.

Fox GM, et al., "cDNA cloning and tissue distribution of five human EPH-like receptor protein-tyrosine kinases.", Oncogene, 1995, pp. 897-905, vol. 10, No. 5.

Garcia-Calero E, et al., "Early mammillary pouch specification in the course of prechordal ventralization of the forebrain tegmentum.", Dev. Biol., 2008, pp. 366-377, vol. 320, issue 2.

Garcia-Calero E, et al., "EphA7 receptor is expressed differentially at chicken prosomeric boundaries.", Neuroscience, 2006, pp. 1887-1897, vol. 141, No. 4.

Guan M, et al., "Aberrant methylation of EphA7 in human prostate cancer and its relation to clinicopathologic features.", Int. J. Cancer, 2009, pp. 88-94, vol. 124, issue 1.

Hafner C, et al., "Expression profile of Eph receptors and ephrin ligands in human skin and downregulation of EphA1 in nonmelanoma skin cancer.", Mod. Pathol., 2006, pp. 1369-1377, vol. 19, No. 10.

Hock B, et al., "PDZ-domain-mediated interaction of the Eph-related receptor tyrosine kinase EphB3 and the ras-binding protein AF6 depends on the kinase activity of the receptor.", Proc. Natl. Acad. Sci. USA., 1998, pp. 9779-9784, vol. 95, No. 17.

Holmberg J, et al., "Ephrin-A2 reverse signaling negatively regulates neural progenitor proliferation and neurogenesis.", Genes Dev., 2005, pp. 462-471, vol. 19, No. 4.

Honig MG, et al., "The contributions of BMP4, positive guidance cues, and repulsive molecules to cutaneous nerve formation in the chick hindlimb.", Dev. Biol., 2005, pp. 257-273, vol. 282, issue 1.

Janis LS, et al., "Ephrin-A binding and EphA receptor expression delineate the matrix compartment of the striatum.", J. Neurosci., 1999, pp. 4962-4971, vol. 19, No. 12.

Katoh Y, et al., "Comparative integromics on Eph family.", Oncol., Rep., 2006, pp. 1391-1395, vol. 15, No. 5.

Lai KO, et al., "Expression of Eph receptors in skeletal muscle and their localization at the neuromuscular junction.", Mol. Cell Neurosci., 2001, pp. 1034-1047, vol. 17, No. 6.

Luukko K, et al., "Expression of ephrin-A ligands and EphA receptors in the developing mouse tooth and its supporting tissues.", Cell Tissue Res., 2005, pp. 143-152, vol. 319, No. 1.

Marin O, et al., "Differential expression of Eph receptors and ephrins correlates with the formation of topographic projections in primary and secondary visual circuits of the embryonic chick forebrain.", Dev. Biol., 2001, pp. 289-303, vol. 234, issue 2.

Martin G, et al., "Differential expression of angioregulatory factors in normal and CNV-derived human retinal pigment epithelium.", Graefe's Arch. Clin. Exp. Ophthalmol., 2004, pp. 321-326, vol. 242, No. 4.

Matsunaga T, et al., "Distinct expression patterns of eph receptors and ephrins relate to the structural organization of the adult rat peripheral vestibular system.", Eur. J. Neurosci., 2000, pp. 1599-1616, vol. 12, issue 5.

Mellott DO, et al., "Divergent roles for Eph and ephrin in avian cranial neural crest.", BMC Dev. Biol., 2008, p. 56, vol. 8.

Miller K, et al., "EphA7-ephrin-A5 signaling in mouse somatosensory cortex: developmental restriction of molecular domains and postnatal maintenance of functional compartments.", J. Comp. Neurol., 2006, pp. 627-642, vol. 496, No. 5.

Miyashita-Lin EM, et al., "Early neocortical regionalization in the absence of thalamic innervation.", Science, 1999, pp. 906-909, vol. 285, No. 5429.

Murai KK, et al., "Targeting the EphA4 receptor in the nervous system with biologically active peptides.", Mol. Cell. Neurosci., 2003, pp. 1000-1011, vol. 24, No. 4.

Nakanishi H, et al., "ALL1 fusion proteins induce deregulation of EphA7 and ERK phosphorylation in human acute leukemias.", Proc. Natl. Acad. Sci. USA., 2007, pp. 14442-14447, vol. 104, No. 36.

Oudes AJ, et al., "Application of Affymetrix array and Massively Parallel Signature Sequencing for identification of genes involved in prostate cancer progression.", BMC Cancer, 2005, p. 86, vol. 5.

Park S, et al., "The Eek receptor, a member of the Eph family of tyrosine protein kinases, can be activated by three different Eph family ligands.", Oncogene, 1997, pp. 533-542, vol. 14, No. 5.

Pinon MC, et al., "Altered molecular regionalization and normal thalamocortical connections in cortex-specific Pax6 knock-out mice.", J. Neurosci., 2008, pp. 8724-8734, vol. 28, No. 35.

Rashid T, et al., "Opposing gradients of ephrin-As and EphA7 in the superior colliculus are essential for topographic mapping in the mammalian visual system.", Neuron, 2005, pp. 57-69, vol. 47, issue 1.

Rogers JH, et al., "Distribution of the receptor EphA7 and its ligands in development of the mouse nervous system.", Brain Res. Mol. Brain Res., 1999, pp. 225-230, vol. 74, Nos. 1-2.

Salsi V, et al., "Hoxd13 and Hoxa13 directly control the expression of the EphA7 Ephrin tyrosine kinase receptor in developing limbs.", J. Biol. Chem., pp. 1992-1999, vol. 281, No. 4, Nov. 28, 2005 (epub).

Shao RX, et al., "Absence of tyrosine kinase mutations in Japanese colorectal cancer patients.", Oncogene, 2007, pp. 2133-2135, vol. 26, No. 14.

Shaut CA, et al., "HOXA13 directly regulates EphA6 and EphA7 expression in the genital tubercle vascular endothelia.", Dev. Dyn., 2007, pp. 951-960, vol. 236, No. 4.

St John JA, et al., "EphA receptors and ephrin-A ligands exhibit highly regulated spatial and temporal expression patterns in the developing olfactory system.", Brain Res. Dev. Brain Res., 2002, pp. 1-14, vol. 138, issue 1.

Stadler HS, et al., "Loss of Eph-receptor expression correlates with loss of cell adhesion and chondrogenic capacity in Hoxa13 mutant limbs.", Development, 2001, pp. 4177-4188, vol. 128, No. 21.

Stubbs J, et al., "Graded expression of EphA3 in the retina and ephrin-A2 in the superior colliculus during initial development of coarse topography in the wallaby retinocollicular projection.", Eur. J. Neurosci., 2000, pp. 3626-3636, vol. 12, No. 10.

Tori M, et al., "Dissociation of corticothalamic and thalamocortical axon targeting by an EphA7-mediated mechanism.", Neuron, 2005, pp. 563-575, vol. 48, No. 4.

(56) References Cited

OTHER PUBLICATIONS

Valenzuela D, et al., "Identification of full-length and truncated forms of Ehk-3, a novel member of the Eph receptor tyrosine kinase family.", Oncogene, 1995, pp. 1573-1580, vol. 10, No. 8.

Vidovic M, et al., "Marsupial retinocollicular system shows differential expression of messenger RNA encoding EphA receptors and their ligands during development.", J. Neurosci. Res., 1999, pp. 244-254, vol. 57, No. 2.

Wang J, et al., "Downregulation of EphA7 by hypermethylation in colorectal cancer.", Oncogene, 2005, pp. 5637-5647, vol. 24, No. 36.

Willson CA, et al., "Upregulation of EphA receptor expression in the injured adult rat spinal cord.", Cell Transplant., 2002, pp. 229-239, vol. 11, No. 3.

Winter J, et al., "Comparative 3'UTR analysis allows identification of regulatory clusters that drive Eph/ephrin expression in cancer cell lines.", PLoS One, 2008, p. e2780, vol. 3, No. 7.

Wlodarczyk BJ, et al., "Arsenic-induced gene expression changes in the neural tube of folate transport defective mouse embryos.", Neurotoxicology, 2006, pp. 547-557, vol. 27, issue 4.

Xu Y, et al., "Expression of Eph receptor tyrosine kinases and their ligands in human Granulosa lutein cells and human umbilical vein endothelial cells.", Exp. Clin. Endocrinol. Diabetes, 2006, pp. 590-595, vol. 114, No. 10.

Yang JJ, et al., "Preparation and analysis of monoclonal antibody against EphA4 peptide.", Zhong Nan Da Xue Xue Bao Yi Xue Ban, 2005, pp. 529-532, vol. 30, No. 5.

Yun ME, et al., "EphA family gene expression in the developing mouse neocortex: regional patterns reveal intrinsic programs and extrinsic influence.", J. Comp. Neurol., 2003, pp. 203-216, vol. 456, No. 3.

Zhao X, et al., "Mutations in HOXD13 underlie syndactyly type V and a novel brachydactyly-syndactyly syndrome.", Am. J. Hum. Genet., 2007, pp. 361-371, vol. 80, No. 2.

FIG.1A

Ephrin type-A receptor 7

Peptide Source: iTRAQ Colorectal Cancer

```
Ephrin type-A receptor 7a (SEQ ID No: 1)    MVFQTRYPSWIILCYIWLLRFAHTGEAQAAKEVLLLDSKAQQTELEWISS  50
Ephrin type-A receptor 7b (SEQ ID No: 2)    MVFQTRYPSWIILCYIWLLRFAHTGEAQAAKEVLLLDSKAQQTELEWISS  50
                                            **************************************************

Ephrin type-A receptor 7a (SEQ ID No: 1)    PPNGWEEISGLDENYTPIRTYQVCQVMEPNQNNWLRTNWISKGNAQRIFV 100
Ephrin type-A receptor 7b (SEQ ID No: 2)    PPNGWEEISGLDENYTPIRTYQVCQVMEPNQNNWLRTNWISKGNAQRIFV 100
                                            **************************************************

Ephrin type-A receptor 7a (SEQ ID No: 1)    ELKFTLRDCNSLPGVLGTCKETFNLYYYETDYDTGRNIRENLYVKIDTIA 150
Ephrin type-A receptor 7b (SEQ ID No: 2)    ELKFTLRDCNSLPGVLGTCKETFNLYYYETDYDTGRNIRENLYVKIDTIA 150
                                            **************************************************

Ephrin type-A receptor 7a (SEQ ID No: 1)    ADESFTQGDLGERKMKLNTEVREIGPLSKKGFYLAFQDVGACIALVSVKV 200
Ephrin type-A receptor 7b (SEQ ID No: 2)    ADESFTQGDLGERKMKLNTEVREIGPLSKKGFYLAFQDVGACIALVSVKV 200
                                            **************************************************

Ephrin type-A receptor 7a (SEQ ID No: 1)    YYKKCWSIIENLAIFPDTVTGSEFSSLVEVRGTCVSSAEEEAENAPRMHC 250
Ephrin type-A receptor 7b (SEQ ID No: 2)    YYKKCWSIIENLAIFPDTVTGSEFSSLVEVRGTCVSSAEEEAENAPRMHC 250
                                            **************************************************

Ephrin type-A receptor 7a (SEQ ID No: 1)    SAEGEWLVPIGKCICKAGYQQKGDTCEPCGRGFYKSSSQDLQCSRCPTHS 300
Ephrin type-A receptor 7b (SEQ ID No: 2)    SAEGEWLVPIGKCICKAGYQQKGDTCEPCGRGFYKSSSQDLQCSRCPTHS 300
                                            **************************************************

Ephrin type-A receptor 7a (SEQ ID No: 1)    FSDKEGSSRCECEDGYYRAPSDPPYVACTRPPSAPQNLIFNINQTTVSLE 350
Ephrin type-A receptor 7b (SEQ ID No: 2)    FSDKEGSSRCECEDGYYRAPSDPPYVACTRPPSAPQNLIFNINQTTVSLE 350
                                            **************************************************

Ephrin type-A receptor 7a (SEQ ID No: 1)    WSPPADNGGRNDVTYRILCKRCSWEQGECVPCGSNIGYMPQQTGLEDNYV 400
Ephrin type-A receptor 7b (SEQ ID No: 2)    WSPPADNGGRNDVTYRILCKRCSWEQGECVPCGSNIGYMPQQTGLEDNYV 400
                                            **************************************************

Ephrin type-A receptor 7a (SEQ ID No: 1)    TVMDLLAHANYTFEVEAVNGVSDLSRSQRLFAAVSITTGQAAPSQVSGVM 450
Ephrin type-A receptor 7b (SEQ ID No: 2)    TVMDLLAHANYTFEVEAVNGVSDLSRSQRLFAAVSITTGQAAPSQVSGVM 450
                                            **************************************************

Ephrin type-A receptor 7a (SEQ ID No: 1)    KERVLQRSVELSWQEPEHPNGVITEYEIKYYEKDQRERTYSTVKTKSTSA 500
Ephrin type-A receptor 7b (SEQ ID No: 2)    KERVLQRSVELSWQEPEHPNGVITEYEIKYYEKDQRERTYSTVKTKSTSA 500
                                            **************************************************

Ephrin type-A receptor 7a (SEQ ID No: 1)    SINNLKPGTVYVFQIRAFTAAGYGNYSPRLDVATLEEATGKMFEATAVSS 550
Ephrin type-A receptor 7b (SEQ ID No: 2)    SINNLKPGTVYVFQIRAFTAAGYGNYSPRLDVATLEEAT-----ATAVSS 545
                                            **************************************     ******

Ephrin type-A receptor 7a (SEQ ID No: 1)    EQNPVIIAVVAVAGTIILVFMVFGFIIGRRHCGYSKADQEGDEELYFHF  600
Ephrin type-A receptor 7b (SEQ ID No: 2)    EQNPVIIAVVAVAGTIILVFMVFGFIIGRRHCGYSKADQEGDEELYFHF  595
                                            **************************************************

Ephrin type-A receptor 7a (SEQ ID No: 1)    KFPGTKTYIDPETYEDPNRAVHQFAKELDASCIKIERVIGAGEFGEVCSG 650
Ephrin type-A receptor 7b (SEQ ID No: 2)    KFPGTKTYIDPETYEDPNRAVHQFAKELDASCIKIERVIGAGEFGEVCSG 645
                                            **************************************************

Ephrin type-A receptor 7a (SEQ ID No: 1)    RLKLPGKRDVAVAIKTLKVGYTEKQRRDFLCEASIMGQFDHPNVVHLEGV 700
Ephrin type-A receptor 7b (SEQ ID No: 2)    RLKLPGKRDVAVAIKTLKVGYTEKQRRDFLCEASIMGQFDHPNVVHLEGV 695
                                            **************************************************

Ephrin type-A receptor 7a (SEQ ID No: 1)    VTRGKPVMIVIEFMENGALDAFLRKHDGQFTVIQLVGMLRGIAAGMRYLA 750
Ephrin type-A receptor 7b (SEQ ID No: 2)    VTRGKPVMIVIEFMENGALDAFLRKHDGQFTVIQLVGMLRGIAAGMRYLA 745
                                            **************************************************

Ephrin type-A receptor 7a (SEQ ID No: 1)    DMGYVHRDLAARNILVNSNLVCKVSDFGLSRVIEDDPEAVYTTTGGKIPV 800
Ephrin type-A receptor 7b (SEQ ID No: 2)    DMGYVHRDLAARNILVNSNLVCKVSDFGLSRVIEDDPEAVYTTTGGKIPV 795
                                            **************************************************

Ephrin type-A receptor 7a (SEQ ID No: 1)    RWTAPEAIQYRKFTSASDVWSYGIVMWEVMSYGERPYWDMSNQDVIKAIE 850
Ephrin type-A receptor 7b (SEQ ID No: 2)    RWTAPEAIQYRKFTSASDVWSYGIVMWEVMSYGERPYWDMSNQDVIKAIE 845
                                            **************************************************
```

FIG 1B

| | | |
|---|---|---|
| Ephrin type-A receptor 7a (SEQ ID No: 1) | EGYRLPAPMDCPAGLHQLMLDCWQKERAERPKFEQIVGILDKMIRNPNSL | 900 |
| Ephrin type-A receptor 7b (SEQ ID No: 2) | EGYRLPAPMDCPAGLHQLMLDCWQKERAERPKFEQIVGILDKMIRNPNSL | 895 |
| | ************************************************** | |
| Ephrin type-A receptor 7a (SEQ ID No: 1) | KTPLGTCSRPISPLLDQNTPDFTTFCSVGEWLQAIKMERYKDNFTAAGYN | 950 |
| Ephrin type-A receptor 7b (SEQ ID No: 2) | KTPLGTCSRPISPLLDQNTPDFTTFCSVGEWLQAIKMERYKDNFTAAGYN | 945 |
| | ************************************************** | |
| Ephrin type-A receptor 7a (SEQ ID No: 1) | SLESVARMTIEDVMSLGITLVGHQKKIMSSIQTMRAQMLHLHGTGIQV | 998 |
| Ephrin type-A receptor 7b (SEQ ID No: 2) | SLESVARMTIEDVMSLGITLVGHQKKIMSSIQTMRAQMLHLHGTGIQV | 993 |
| | *********************************************** | |

Mass Match Peptides (bold):
ADQEGDEELYFHFK [3]
CPTHSFSDK [6]
VSDFGLSR [10]
WTAPEAIQYR [11]

Tandem Peptides (underline):
ADQEGDEELYFHFK [3]
CPTHSFSDK [6]
VSDFGLSR [10]
WTAPEAIQYR [11]

Peptide Source: iTRAQ Non-Small Cell Lung Cancer

| | | |
|---|---|---|
| Ephrin type-A receptor 7a (SEQ ID No: 1) | MVFQTRYPSWIILCYIWLLRFAHTGEAQAAKEVLLLDSKAQQTELEWISS | 50 |
| Ephrin type-A receptor 7b (SEQ ID No: 2) | MVFQTRYPSWIILCYIWLLRFAHTGEAQAAKEVLLLDSKAQQTELEWISS | 50 |
| | ************************************************** | |
| Ephrin type-A receptor 7a (SEQ ID No: 1) | PPNGWEEISGLDENYTPIRTYQVCQVMEPNQNNWLRTNWISKGNAQRIFV | 100 |
| Ephrin type-A receptor 7b (SEQ ID No: 2) | PPNGWEEISGLDENYTPIRTYQVCQVMEPNQNNWLRTNWISKGNAQRIFV | 100 |
| | ************************************************** | |
| Ephrin type-A receptor 7a (SEQ ID No: 1) | ELKFTLRDCNSLPGVLGTCKETFNLYYYETDYDTGRNIRENLYVKIDTIA | 150 |
| Ephrin type-A receptor 7b (SEQ ID No: 2) | ELKFTLRDCNSLPGVLGTCKETFNLYYYETDYDTGRNIRENLYVKIDTIA | 150 |
| | ************************************************** | |
| Ephrin type-A receptor 7a (SEQ ID No: 1) | ADESFTQGDLGERKMKLNTEVREIGPLSKKGFYLAFQDVGACIALVSVKV | 200 |
| Ephrin type-A receptor 7b (SEQ ID No: 2) | ADESFTQGDLGERKMKLNTEVREIGPLSKKGFYLAFQDVGACIALVSVKV | 200 |
| | ************************************************** | |
| Ephrin type-A receptor 7a (SEQ ID No: 1) | YYKKCWSIIENLAIFPDTVTGSEFSSLVEVRGTCVSSAEEEAENAPRMHC | 250 |
| Ephrin type-A receptor 7b (SEQ ID No: 2) | YYKKCWSIIENLAIFPDTVTGSEFSSLVEVRGTCVSSAEEEAENAPRMHC | 250 |
| | ************************************************** | |
| Ephrin type-A receptor 7a (SEQ ID No: 1) | SAEGEWLVPIGKCICKAGYQQKGDTCEPCGRGFYKSSSQDLQCSRCPTHS | 300 |
| Ephrin type-A receptor 7b (SEQ ID No: 2) | SAEGEWLVPIGKCICKAGYQQKGDTCEPCGRGFYKSSSQDLQCSRCPTHS | 300 |
| | ************************************************** | |
| Ephrin type-A receptor 7a (SEQ ID No: 1) | FSDKEGSSRCECEDGYYRAPSDPPYVACTRPPSAPQNLIFNINQTTVSLE | 350 |
| Ephrin type-A receptor 7b (SEQ ID No: 2) | FSDKEGSSRCECEDGYYRAPSDPPYVACTRPPSAPQNLIFNINQTTVSLE | 350 |
| | ************************************************** | |
| Ephrin type-A receptor 7a (SEQ ID No: 1) | WSPPADNGGRNDVTYRILCKRCSWEQGECVPCGSNIGYMPQQTGLEDNYV | 400 |
| Ephrin type-A receptor 7b (SEQ ID No: 2) | WSPPADNGGRNDVTYRILCKRCSWEQGECVPCGSNIGYMPQQTGLEDNYV | 400 |
| | ************************************************** | |
| Ephrin type-A receptor 7a (SEQ ID No: 1) | TVMDLLAHANYTFEVEAVNGVSDLSRSQRLFAAVSITTGQAAPSQVSGVM | 450 |
| Ephrin type-A receptor 7b (SEQ ID No: 2) | TVMDLLAHANYTFEVEAVNGVSDLSRSQRLFAAVSITTGQAAPSQVSGVM | 450 |
| | ************************************************** | |
| Ephrin type-A receptor 7a (SEQ ID No: 1) | KERVLQRSVELSWQEPEHPNGVITEYEIKYYEKDQRERTYSTVKTKSTSA | 500 |
| Ephrin type-A receptor 7b (SEQ ID No: 2) | KERVLQRSVELSWQEPEHPNGVITEYEIKYYEKDQRERTYSTVKTKSTSA | 500 |
| | ************************************************** | |
| Ephrin type-A receptor 7a (SEQ ID No: 1) | SINNLKPGTVYVFQIRAFTAAGYGNYSPRLDVATLEEATGKMFEATAVSS | 550 |
| Ephrin type-A receptor 7b (SEQ ID No: 2) | SINNLKPGTVYVFQIRAFTAAGYGNYSPRLDVATLEEAT-----ATAVSS | 545 |
| | ******************************************     ***** | |
| Ephrin type-A receptor 7a (SEQ ID No: 1) | EQNPVIIAVVAVAGTIILVFMVFGFIIGRRHCGYSKADQEGDEELYFHF | 600 |
| Ephrin type-A receptor 7b (SEQ ID No: 2) | EQNPVIIAVVAVAGTIILVFMVFGFIIGRRHCGYSKADQEGDEELYFHF | 595 |
| | ************************************************* | |

FIG 1C

| | |
|---|---|
| Ephrin type-A receptor 7a (SEQ ID No: 1) | KPPGTKTYIDPETYEDPNRAVHQFAKELDASCIKIERVIGAGEFGEVCSG 650 |
| Ephrin type-A receptor 7b (SEQ ID No: 2) | KFPGTKTYIDPETYEDPNRAVHQFAKELDASCIKIERVIGAGEFGEVCSG 645 |

| | |
|---|---|
| Ephrin type-A receptor 7a (SEQ ID No: 1) | RLKLPGKRDVAVAIKTLKVGYTEKQRRDFLCEASIMGQFDHPNVVHLEGV 700 |
| Ephrin type-A receptor 7b (SEQ ID No: 2) | RLKLPGKRDVAVAIKTLKVGYTEKQRRDFLCEASIMGQFDHPNVVHLEGV 695 |

| | |
|---|---|
| Ephrin type-A receptor 7a (SEQ ID No: 1) | VTRGKPVMIVIEFMENGALDAFLRKHDGQFTVIQLVGMLRGIAAGMRYLA 750 |
| Ephrin type-A receptor 7b (SEQ ID No: 2) | VTRGKPVMIVIEFMENGALDAFLRKHDGQFTVIQLVGMLRGIAAGMRYLA 745 |

| | |
|---|---|
| Ephrin type-A receptor 7a (SEQ ID No: 1) | DMGYVHRDLAARNILVNSNLVCKVSDFGLSRVIEDDPEAVYTTTGGKIPV 800 |
| Ephrin type-A receptor 7b (SEQ ID No: 2) | DMGYVHRDLAARNILVNSNLVCKVSDFGLSRVIEDDPEAVYTTTGGKIPV 795 |

| | |
|---|---|
| Ephrin type-A receptor 7a (SEQ ID No: 1) | RWTAPEAIQYRKFTSASDVWSYGIVMWEVMSYGERPYWDMSNQDVIKAIE 850 |
| Ephrin type-A receptor 7b (SEQ ID No: 2) | RWTAPEAIQYRKFTSASDVWSYGIVMWEVMSYGERPYWDMSNQDVIKAIE 845 |

| | |
|---|---|
| Ephrin type-A receptor 7a (SEQ ID No: 1) | EGYRLPAPMDCPAGLHQLMLDCWQKERAERPKFEQIVGILDKMIRNPNSL 900 |
| Ephrin type-A receptor 7b (SEQ ID No: 2) | EGYRLPAPMDCPAGLHQLMLDCWQKERAERPKFEQIVGILDKMIRNPNSL 895 |

| | |
|---|---|
| Ephrin type-A receptor 7a (SEQ ID No: 1) | KTPLGTCSRPISPLLDQNTPDFTTFCSVGEWLQAIKMERYKDNFTAAGYN 950 |
| Ephrin type-A receptor 7b (SEQ ID No: 2) | KTPLGTCSRPISPLLDQNTPDFTTFCSVGEWLQAIKMERYKDNFTAAGYN 945 |

| | |
|---|---|
| Ephrin type-A receptor 7a (SEQ ID No: 1) | SLESVARMTIEDVMSLGITLVGHQKKIMSSIQTMRAQMLHLHGTGIQV 998 |
| Ephrin type-A receptor 7b (SEQ ID No: 2) | SLESVARMTIEDVMSLGITLVGHQKKIMSSIQTMRAQMLHLHGTGIQV 993 |

Mass Match Peptides (bold):
ADQEGDEELYFHFK [3]
CPTHSFSDK [6]
VSDFGLSR [10]
WTAPEAIQYR [11]

Tandem Peptides (underline):
ADQEGDEELYFHFK [3]
CPTHSFSDK [6]
VSDFGLSR [10]
WTAPEAIQYR [11]

Peptide Source: iTRAQ Breast Cancer

| | |
|---|---|
| Ephrin type-A receptor 7a (SEQ ID No: 1) | MVFQTRYPSWIILCYIWLLRFAHTGEAQAAKEVLLLDSKAQQTELEWISS 50 |
| Ephrin type-A receptor 7b (SEQ ID No: 2) | MVFQTRYPSWIILCYIWLLRFAHTGEAQAAKEVLLLDSKAQQTELEWISS 50 |

| | |
|---|---|
| Ephrin type-A receptor 7a (SEQ ID No: 1) | PPNGWEEISGLDENYTPIRTYQVCQVMEPNQNNWLRTNWISKGNAQRIFV 100 |
| Ephrin type-A receptor 7b (SEQ ID No: 2) | PPNGWEEISGLDENYTPIRTYQVCQVMEPNQNNWLRTNWISKGNAQRIFV 100 |

| | |
|---|---|
| Ephrin type-A receptor 7a (SEQ ID No: 1) | ELKFTLRDCNSLPGVLGTCKETFNLYYYETDYDTGRNIRENLYVKIDTIA 150 |
| Ephrin type-A receptor 7b (SEQ ID No: 2) | ELKFTLRDCNSLPGVLGTCKETFNLYYYETDYDTGRNIRENLYVKIDTIA 150 |

| | |
|---|---|
| Ephrin type-A receptor 7a (SEQ ID No: 1) | ADESFTQGDLGERKMKLNTEVREIGPLSKKGFYLAFQDVGACIALVSVKV 200 |
| Ephrin type-A receptor 7b (SEQ ID No: 2) | ADESFTQGDLGERKMKLNTEVREIGPLSKKGFYLAFQDVGACIALVSVKV 200 |

| | |
|---|---|
| Ephrin type-A receptor 7a (SEQ ID No: 1) | YYKKCWSIIENLAIFPDTVTGSEFSSLVEVRGTCVSSAEEEAENAPRMHC 250 |
| Ephrin type-A receptor 7b (SEQ ID No: 2) | YYKKCWSIIENLAIFPDTVTGSEFSSLVEVRGTCVSSAEEEAENAPRMHC 250 |

| | |
|---|---|
| Ephrin type-A receptor 7a (SEQ ID No: 1) | SAEGEWLVPIGKCICKAGYQQKGDTCEPCGRGFYKSSSQDLQCSRCPTHS 300 |
| Ephrin type-A receptor 7b (SEQ ID No: 2) | SAEGEWLVPIGKCICKAGYQQKGDTCEPCGRGFYKSSSQDLQCSRCPTHS 300 |

| | |
|---|---|
| Ephrin type-A receptor 7a (SEQ ID No: 1) | FSDKEGSSRCECEDGYYRAPSDPPYVACTRPPSAPQNLIFNINQTTVSLE 350 |
| Ephrin type-A receptor 7b (SEQ ID No: 2) | FSDKEGSSRCECEDGYYRAPSDPPYVACTRPPSAPQNLIFNINQTTVSLE 350 |

FIG 1D

```
Ephrin type-A receptor 7a (SEQ ID No: 1)    WSPPADNGGRNDVTYRILCKRCSWEQGECVPCGSNIGYMPQQTGLEDNYV  400
Ephrin type-A receptor 7b (SEQ ID No: 2)    WSPPADNGGRNDVTYRILCKRCSWEQGECVPCGSNIGYMPQQTGLEDNYV  400
                                            **************************************************

Ephrin type-A receptor 7a (SEQ ID No: 1)    TVMDLLAHANYTFEVEAVNGVSDLSRSQRLFAAVSITTGQAAPSQVSGVM  450
Ephrin type-A receptor 7b (SEQ ID No: 2)    TVMDLLAHANYTFEVEAVNGVSDLSRSQRLFAAVSITTGQAAPSQVSGVM  450
                                            **************************************************

Ephrin type-A receptor 7a (SEQ ID No: 1)    KERVLQRSVELSWQEPEHPNGVITEYEIKYYEKDQRERTYSTVKTKSTSA  500
Ephrin type-A receptor 7b (SEQ ID No: 2)    KERVLQRSVELSWQEPEHPNGVITEYEIKYYEKDQRERTYSTVKTKSTSA  500
                                            **************************************************

Ephrin type-A receptor 7a (SEQ ID No: 1)    SINNLKPGTVYVFQIRAFTAAGYGNYSPRLDVATLEEATGKMFEATAVSS  550
Ephrin type-A receptor 7b (SEQ ID No: 2)    SINNLKPGTVYVFQIRAFTAAGYGNYSPRLDVATLEEAT-----ATAVSS  545
                                            **************************************          *****

Ephrin type-A receptor 7a (SEQ ID No: 1)    EQNPVIIIAVVAVAGTIILVFMVFGFIIGRRHCGYSKADQEGDEELYFHF  600
Ephrin type-A receptor 7b (SEQ ID No: 2)    EQNPVIIIAVVAVAGTIILVFMVFGFIIGRRHCGYSKADQEGDEELYFHF  595
                                            **************************************************

Ephrin type-A receptor 7a (SEQ ID No: 1)    KPPGTKTYIDPETYEDPNRAVHQFAKELDASCIKIERVIGAGEFGEVCSG  650
Ephrin type-A receptor 7b (SEQ ID No: 2)    KPPGTKTYIDPETYEDPNRAVHQFAKELDASCIKIERVIGAGEFGEVCSG  645
                                            **************************************************

Ephrin type-A receptor 7a (SEQ ID No: 1)    RLKLPGKRDVAVAIKTLKVGYTEKQRRDFLCEASIMGQFDHPNVVHLEGV  700
Ephrin type-A receptor 7b (SEQ ID No: 2)    RLKLPGKRDVAVAIKTLKVGYTEKQRRDFLCEASIMGQFDHPNVVHLEGV  695
                                            **************************************************

Ephrin type-A receptor 7a (SEQ ID No: 1)    VTRGKPVMIVIEFMENGALDAFLRKHDGQFTVIQLVGMLRGIAAGMRYLA  750
Ephrin type-A receptor 7b (SEQ ID No: 2)    VTRGKPVMIVIEFMENGALDAFLRKHDGQFTVIQLVGMLRGIAAGMRYLA  745
                                            **************************************************

Ephrin type-A receptor 7a (SEQ ID No: 1)    DMGYVHRDLAARNILVNSNLVCKVSDFGLSRVIEDDPEAVYTTTGGKIPV  800
Ephrin type-A receptor 7b (SEQ ID No: 2)    DMGYVHRDLAARNILVNSNLVCKVSDFGLSRVIEDDPEAVYTTTGGKIPV  795
                                            **************************************************

Ephrin type-A receptor 7a (SEQ ID No: 1)    RWTAPEAIQYRKFTSASDVWSYGIVMWEVMSYGERPYWDMSNQDVIKAIE  850
Ephrin type-A receptor 7b (SEQ ID No: 2)    RWTAPEAIQYRKFTSASDVWSYGIVMWEVMSYGERPYWDMSNQDVIKAIE  845
                                            **************************************************

Ephrin type-A receptor 7a (SEQ ID No: 1)    EGYRLPAPMDCPAGLHQLMLDCWQKERAERPKFEQIVGILDKMIRNPNSL  900
Ephrin type-A receptor 7b (SEQ ID No: 2)    EGYRLPAPMDCPAGLHQLMLDCWQKERAERPKFEQIVGILDKMIRNPNSL  895
                                            **************************************************

Ephrin type-A receptor 7a (SEQ ID No: 1)    KTPLGTCSRPISPLLDQNTPDFTTFCSVGEWLQAIKMERYKDNFTAAGYN  950
Ephrin type-A receptor 7b (SEQ ID No: 2)    KTPLGTCSRPISPLLDQNTPDFTTFCSVGEWLQAIKMERYKDNFTAAGYN  945
                                            **************************************************

Ephrin type-A receptor 7a (SEQ ID No: 1)    SLESVARMTIEDVMSLGITLVGHQKKIMSSIQTMRAQMLHLHGTGIQV    998
Ephrin type-A receptor 7b (SEQ ID No: 2)    SLESVARMTIEDVMSLGITLVGHQKKIMSSIQTMRAQMLHLHGTGIQV    993
                                            ************************************************
```

Mass Match Peptides (bold):
ADQEGDEELYFHFK [3]
CPTHSFSDK [6]
WTAPEAIQYR [11]

Tandem Peptides (underline):
ADQEGDEELYFHFK [3]
CPTHSFSDK [6]
WTAPEAIQYR [11]

Peptide Source: 1D GE Colorectal Cancer

```
Ephrin type-A receptor 7a (SEQ ID No: 1)    MVFQTRYPSWIILCYIWLLRFAHTGEAQAAKEVLLLDSKAQQTELEWISS  50
Ephrin type-A receptor 7b (SEQ ID No: 2)    MVFQTRYPSWIILCYIWLLRFAHTGEAQAAKEVLLLDSKAQQTELEWISS  50
                                            **************************************************

Ephrin type-A receptor 7a (SEQ ID No: 1)    PPNGWEEISGLDENYTPIRTYQVCQVMEPNQNNWLRTNWISKGNAQRIFV  100
Ephrin type-A receptor 7b (SEQ ID No: 2)    PPNGWEEISGLDENYTPIRTYQVCQVMEPNQNNWLRTNWISKGNAQRIFV  100
                                            **************************************************
```

FIG 1E

| | | |
|---|---|---|
| Ephrin type-A receptor 7a (SEQ ID No: 1) | ELKFTLRDCNSLPGVLGTCKETFNLYYYETDYDTGRNIRENLYVKIDTIA | 150 |
| Ephrin type-A receptor 7b (SEQ ID No: 2) | ELKFTLRDCNSLPGVLGTCKETFNLYYYETDYDTGRNIRENLYVKIDTIA | 150 |
| | ************************************************** | |
| Ephrin type-A receptor 7a (SEQ ID No: 1) | ADESFTQGDLGERKMKLNTEVREIGPLSKKGFYLAFQDVGACIALVSVKV | 200 |
| Ephrin type-A receptor 7b (SEQ ID No: 2) | ADESFTQGDLGERKMKLNTEVREIGPLSKKGFYLAFQDVGACIALVSVKV | 200 |
| | ************************************************** | |
| Ephrin type-A receptor 7a (SEQ ID No: 1) | YYKKCWSIIENLAIFPDTVTGSEFSSLVEVRGTCVSSAEEEAENAPRMHC | 250 |
| Ephrin type-A receptor 7b (SEQ ID No: 2) | YYKKCWSIIENLAIFPDTVTGSEFSSLVEVRGTCVSSAEEEAENAPRMHC | 250 |
| | ************************************************** | |
| Ephrin type-A receptor 7a (SEQ ID No: 1) | SAEGEWLVPIGKCICKAGYQQKGDTCEPCGRGFYKSSSQDLQCSRCPTHS | 300 |
| Ephrin type-A receptor 7b (SEQ ID No: 2) | SAEGEWLVPIGKCICKAGYQQKGDTCEPCGRGFYKSSSQDLQCSRCPTHS | 300 |
| | ************************************************** | |
| Ephrin type-A receptor 7a (SEQ ID No: 1) | FSDKEGSSRCECEDGYYRAPSDPPYVACTRPPSAPQNLIFNINQTTVSLE | 350 |
| Ephrin type-A receptor 7b (SEQ ID No: 2) | FSDKEGSSRCECEDGYYRAPSDPPYVACTRPPSAPQNLIFNINQTTVSLE | 350 |
| | ************************************************** | |
| Ephrin type-A receptor 7a (SEQ ID No: 1) | WSPPADNGGRNDVTYRILCKRCSWEQGECVPCGSNIGYMPQQTGLEDNYV | 400 |
| Ephrin type-A receptor 7b (SEQ ID No: 2) | WSPPADNGGRNDVTYRILCKRCSWEQGECVPCGSNIGYMPQQTGLEDNYV | 400 |
| | ************************************************** | |
| Ephrin type-A receptor 7a (SEQ ID No: 1) | TVMDLLAHANYTFEVEAVNGVSDLSRSQRLFAAVSITTGQAAPSQVSGVM | 450 |
| Ephrin type-A receptor 7b (SEQ ID No: 2) | TVMDLLAHANYTFEVEAVNGVSDLSRSQRLFAAVSITTGQAAPSQVSGVM | 450 |
| | ************************************************** | |
| Ephrin type-A receptor 7a (SEQ ID No: 1) | KERVLQRSVELSWQEPEHPNGVITEYEIKYYEKDQRERTYSTVKTKSTSA | 500 |
| Ephrin type-A receptor 7b (SEQ ID No: 2) | KERVLQRSVELSWQEPEHPNGVITEYEIKYYEKDQRERTYSTVKTKSTSA | 500 |
| | ************************************************** | |
| Ephrin type-A receptor 7a (SEQ ID No: 1) | SINNLKPGTVYVFQIRAFTAAGYGNYSPRLDVATLEEATGKMFEATAVSS | 550 |
| Ephrin type-A receptor 7b (SEQ ID No: 2) | SINNLKPGTVYVFQIRAFTAAGYGNYSPRLDVATLEEAT-----ATAVSS | 545 |
| | **************************************      ****** | |
| Ephrin type-A receptor 7a (SEQ ID No: 1) | EQNPVIIAVVAVAGTIILVFMVFGFIIGRRECGYSKADQEGDEELYFHF | 600 |
| Ephrin type-A receptor 7b (SEQ ID No: 2) | EQNPVIIAVVAVAGTIILVFMVFGFIIGRRECGYSKADQEGDEELYFHF | 595 |
| | ************************************************** | |
| Ephrin type-A receptor 7a (SEQ ID No: 1) | KFPGTKTYIDPETYEDPNRAVHQFAKELDASCIKIERVIGAGEFGEVCSG | 650 |
| Ephrin type-A receptor 7b (SEQ ID No: 2) | KFPGTKTYIDPETYEDPNRAVHQFAKELDASCIKIERVIGAGEFGEVCSG | 645 |
| | ************************************************** | |
| Ephrin type-A receptor 7a (SEQ ID No: 1) | RLKLPGKRDVAVAIKTLKVGYTEKQRRDFLCEASIMGQFDHPNVVHLEGV | 700 |
| Ephrin type-A receptor 7b (SEQ ID No: 2) | RLKLPGKRDVAVAIKTLKVGYTEKQRRDFLCEASIMGQFDHPNVVHLEGV | 695 |
| | ************************************************** | |
| Ephrin type-A receptor 7a (SEQ ID No: 1) | VTRGKPVMIVIEFMENGALDAFLRKEDGQFTVIQLVGMLRGIAAGMRYLA | 750 |
| Ephrin type-A receptor 7b (SEQ ID No: 2) | VTRGKPVMIVIEFMENGALDAFLRKEDGQFTVIQLVGMLRGIAAGMRYLA | 745 |
| | ************************************************** | |
| Ephrin type-A receptor 7a (SEQ ID No: 1) | DMGYVHRDLAARNILVNSNLVCKVBDFGLSRVIEDDPEAVYTTTGGKIPV | 800 |
| Ephrin type-A receptor 7b (SEQ ID No: 2) | DMGYVHRDLAARNILVNSNLVCKVBDFGLSRVIEDDPEAVYTTTGGKIPV | 795 |
| | ************************************************** | |
| Ephrin type-A receptor 7a (SEQ ID No: 1) | RWTAPEAIQYRKFTSASDVWSYGIVMWEVMSYGERPYWDMSNQDVIKAIE | 850 |
| Ephrin type-A receptor 7b (SEQ ID No: 2) | RWTAPEAIQYRKFTSASDVWSYGIVMWEVMSYGERPYWDMSNQDVIKAIE | 845 |
| | ************************************************** | |
| Ephrin type-A receptor 7a (SEQ ID No: 1) | EGYRLPAPMDCPAGLHQLMLDCWQKERAERPKFEQIVGILDKMIRNPNSL | 900 |
| Ephrin type-A receptor 7b (SEQ ID No: 2) | EGYRLPAPMDCPAGLHQLMLDCWQKERAERPKFEQIVGILDKMIRNPNSL | 895 |
| | ************************************************** | |
| Ephrin type-A receptor 7a (SEQ ID No: 1) | KTPLGTCSRPISPLLDQNTPDFTTFCSVGEWLQAIKMERYKDNFTAAGYN | 950 |
| Ephrin type-A receptor 7b (SEQ ID No: 2) | KTPLGTCSRPISPLLDQNTPDFTTFCSVGEWLQAIKMERYKDNFTAAGYN | 945 |
| | ************************************************** | |
| Ephrin type-A receptor 7a (SEQ ID No: 1) | SLESVARMTIEDVMSLGITLVGHQKKIMSSIQTMRAQMLHLHGTGIQV | 998 |
| Ephrin type-A receptor 7b (SEQ ID No: 2) | SLESVARMTIEDVMSLGITLVGHQKKIMSSIQTMRAQMLHLHGTGIQV | 993 |
| | ************************************************ | |

Mass Match Peptides (bold):
AFTAAGYGNYSPR [4]
AIEEGYR [5]
CPTHSFSDK [6]

FIG 1F

HDGQFTVIQLVGMLR [7]
RHCGYSK [9]
VSDFGLSR [10]

Tandem Peptides (underline):
WTAPEAIQYR [11]

Peptide Source: 1D GE Osteosarcoma

```
Ephrin type-A receptor 7a (SEQ ID No: 1)    MVFQTRYPSWIILCYIWLLRFAHTGEAQAAKEVLLLDSKAQQTELEWISS 50
Ephrin type-A receptor 7b (SEQ ID No: 2)    MVFQTRYPSWIILCYIWLLRFAHTGEAQAAKEVLLLDSKAQQTELEWISS 50
                                            **************************************************

Ephrin type-A receptor 7a (SEQ ID No: 1)    PPNGWEEISGLDENYTPIRTYQVCQVMEPNQNNWLRTNWISKGNAQRIFV 100
Ephrin type-A receptor 7b (SEQ ID No: 2)    PPNGWEEISGLDENYTPIRTYQVCQVMEPNQNNWLRTNWISKGNAQRIFV 100
                                            **************************************************

Ephrin type-A receptor 7a (SEQ ID No: 1)    ELKFTLRDCNSLPGVLGTCKETFNLYYYETDYDTGRNIRENLYVKIDTIA 150
Ephrin type-A receptor 7b (SEQ ID No: 2)    ELKFTLRDCNSLPGVLGTCKETFNLYYYETDYDTGRNIRENLYVKIDTIA 150
                                            **************************************************

Ephrin type-A receptor 7a (SEQ ID No: 1)    ADESFTQGDLGERKMKLNTEVREIGPLSKKGFYLAFQDVGACIALVSVKV 200
Ephrin type-A receptor 7b (SEQ ID No: 2)    ADESFTQGDLGERKMKLNTEVREIGPLSKKGFYLAFQDVGACIALVSVKV 200
                                            **************************************************

Ephrin type-A receptor 7a (SEQ ID No: 1)    YYKKCWSIIENLAIFPDTVTGSEFSSLVEVRGTCVSSAEEEAENAPRMHC 250
Ephrin type-A receptor 7b (SEQ ID No: 2)    YYKKCWSIIENLAIFPDTVTGSEFSSLVEVRGTCVSSAEEEAENAPRMHC 250
                                            **************************************************

Ephrin type-A receptor 7a (SEQ ID No: 1)    SAEGEWLVPIGKCICKAGYQQKGDTCEPCGRGFYKSSSQDLQCSRCPTHS 300
Ephrin type-A receptor 7b (SEQ ID No: 2)    SAEGEWLVPIGKCICKAGYQQKGDTCEPCGRGFYKSSSQDLQCSRCPTHS 300
                                            **************************************************

Ephrin type-A receptor 7a (SEQ ID No: 1)    FSDKEGSSRCECEDGYYRAPSDPPYVACTRPPSAPQNLIFNINQTTVSLE 350
Ephrin type-A receptor 7b (SEQ ID No: 2)    FSDKEGSSRCECEDGYYRAPSDPPYVACTRPPSAPQNLIFNINQTTVSLE 350
                                            **************************************************

Ephrin type-A receptor 7a (SEQ ID No: 1)    WSPPADNGGRNDVTYRILCKRCSWEQGECVPCGSNIGYMPQQTGLEDNYV 400
Ephrin type-A receptor 7b (SEQ ID No: 2)    WSPPADNGGRNDVTYRILCKRCSWEQGECVPCGSNIGYMPQQTGLEDNYV 400
                                            **************************************************

Ephrin type-A receptor 7a (SEQ ID No: 1)    TVMDLLAHANYTFEVEAVNGVSDLSRSQRLFAAVSITTGQAAPSQVSGVM 450
Ephrin type-A receptor 7b (SEQ ID No: 2)    TVMDLLAHANYTFEVEAVNGVSDLSRSQRLFAAVSITTGQAAPSQVSGVM 450
                                            **************************************************

Ephrin type-A receptor 7a (SEQ ID No: 1)    KERVLQRSVELSWQEPEHPNGVITEYEIKYYEKDQRERTYSTVKTKSTSA 500
Ephrin type-A receptor 7b (SEQ ID No: 2)    KERVLQRSVELSWQEPEHPNGVITEYEIKYYEKDQRERTYSTVKTKSTSA 500
                                            **************************************************

Ephrin type-A receptor 7a (SEQ ID No: 1)    SINNLKPGTVYVFQIRAFTAAGYGNYSPRLDVATLEEATGKMFEATAVSS 550
Ephrin type-A receptor 7b (SEQ ID No: 2)    SINNLKPGTVYVFQIRAFTAAGYGNYSPRLDVATLEEAT-----ATAVSS 545
                                            ***************************************     ******

Ephrin type-A receptor 7a (SEQ ID No: 1)    EQNPVIIAVVAVAGTIILVFMVFGFIIGRRHCGYSKADQEGDEELYFHF 600
Ephrin type-A receptor 7b (SEQ ID No: 2)    EQNPVIIAVVAVAGTIILVFMVFGFIIGRRHCGYSKADQEGDEELYFHF 595
                                            **************************************************

Ephrin type-A receptor 7a (SEQ ID No: 1)    KFPGTKTYIDPETYEDPNRAVHQFAKELDASCIKIERVIGAGEFGEVCSG 650
Ephrin type-A receptor 7b (SEQ ID No: 2)    KFPGTKTYIDPETYEDPNRAVHQFAKELDASCIKIERVIGAGEFGEVCSG 645
                                            **************************************************

Ephrin type-A receptor 7a (SEQ ID No: 1)    RLKLPGKRDVAVAIKTLKVGYTEKQRRDFLCEASIMGQFDHPNVVHLEGV 700
Ephrin type-A receptor 7b (SEQ ID No: 2)    RLKLPGKRDVAVAIKTLKVGYTEKQRRDFLCEASIMGQFDHPNVVHLEGV 695
                                            **************************************************

Ephrin type-A receptor 7a (SEQ ID No: 1)    VTRGKPVMIVIEFMENGALDAFLRKHDGQFTVIQLVGMLRGIAAGMRYLA 750
Ephrin type-A receptor 7b (SEQ ID No: 2)    VTRGKPVMIVIEFMENGALDAFLRKHDGQFTVIQLVGMLRGIAAGMRYLA 745
                                            **************************************************

Ephrin type-A receptor 7a (SEQ ID No: 1)    DMGYVHRDLAARNILVNSNLVCKVSDFGLSRVIEDDPEAVYTTTGGKIPV 800
Ephrin type-A receptor 7b (SEQ ID No: 2)    DMGYVHRDLAARNILVNSNLVCKVSDFGLSRVIEDDPEAVYTTTGGKIPV 795
                                            **************************************************
```

FIG 1G

| | | |
|---|---|---|
| Ephrin type-A receptor 7a (SEQ ID No: 1) | RWTAPEAIQYRKFTSASDVWSYGIVMWEVMSYGERPYWDMSNQDVIKAIE | 850 |
| Ephrin type-A receptor 7b (SEQ ID No: 2) | RWTAPEAIQYRKFTSASDVWSYGIVMWEVMSYGERPYWDMSNQDVIKAIE | 845 |
| | ************************************************** | |
| Ephrin type-A receptor 7a (SEQ ID No: 1) | EGYRLPAPMDCPAGLHQLMLDCWQKERAERPKFEQIVGILDKMIRNPNSL | 900 |
| Ephrin type-A receptor 7b (SEQ ID No: 2) | EGYRLPAPMDCPAGLHQLMLDCWQKERAERPKFEQIVGILDKMIRNPNSL | 895 |
| | ************************************************** | |
| Ephrin type-A receptor 7a (SEQ ID No: 1) | KTPLGTCSRPISPLLDQNTPDFTTFCSVGEWLQAIKMERYKDNFTAAGYN | 950 |
| Ephrin type-A receptor 7b (SEQ ID No: 2) | KTPLGTCSRPISPLLDQNTPDFTTFCSVGEWLQAIKMERYKDNFTAAGYN | 945 |
| | ************************************************** | |
| Ephrin type-A receptor 7a (SEQ ID No: 1) | SLESVARMTIEDVMSLGITLVGHQKKIMSSIQTMRAQMLHLHGTGIQV | 998 |
| Ephrin type-A receptor 7b (SEQ ID No: 2) | SLESVARMTIEDVMSLGITLVGHQKKIMSSIQTMRAQMLHLHGTGIQV | 993 |
| | ************************************************** | |

Mass Match Peptides (bold):
MTIEDVMSLGITLVGHQK [8]

Tandem Peptides (underline):
ADQEGDEELYFHFK [3]

Peptide Source: ICAT Prostate Cancer

| | | |
|---|---|---|
| Ephrin type-A receptor 7a (SEQ ID No: 1) | MVFQTRYPSWIILCYIWLLRFAHTGEAQAAKEVLLLDSKAQQTELEWISS | 50 |
| Ephrin type-A receptor 7b (SEQ ID No: 2) | MVFQTRYPSWIILCYIWLLRFAHTGEAQAAKEVLLLDSKAQQTELEWISS | 50 |
| | ************************************************** | |
| Ephrin type-A receptor 7a (SEQ ID No: 1) | PPNGWEEISGLDENYTPIRTYQVCQVMEPNQNNWLRTNWISKGNAQRIFV | 100 |
| Ephrin type-A receptor 7b (SEQ ID No: 2) | PPNGWEEISGLDENYTPIRTYQVCQVMEPNQNNWLRTNWISKGNAQRIFV | 100 |
| | ************************************************** | |
| Ephrin type-A receptor 7a (SEQ ID No: 1) | ELKFTLRDCNSLPGVLGTCKETFNLYYYETDYDTGRNIRENLYVKIDTIA | 150 |
| Ephrin type-A receptor 7b (SEQ ID No: 2) | ELKFTLRDCNSLPGVLGTCKETFNLYYYETDYDTGRNIRENLYVKIDTIA | 150 |
| | ************************************************** | |
| Ephrin type-A receptor 7a (SEQ ID No: 1) | ADESFTQGDLGERKMKLNTEVREIGPLSKKGFYLAFQDVGACIALVSVKV | 200 |
| Ephrin type-A receptor 7b (SEQ ID No: 2) | ADESFTQGDLGERKMKLNTEVREIGPLSKKGFYLAFQDVGACIALVSVKV | 200 |
| | ************************************************** | |
| Ephrin type-A receptor 7a (SEQ ID No: 1) | YYKKCWSIIENLAIFPDTVTGSEFSSLVEVRGTCVSSAEEEAENAPRMHC | 250 |
| Ephrin type-A receptor 7b (SEQ ID No: 2) | YYKKCWSIIENLAIFPDTVTGSEFSSLVEVRGTCVSSAEEEAENAPRMHC | 250 |
| | ************************************************** | |
| Ephrin type-A receptor 7a (SEQ ID No: 1) | SAEGEWLVPIGKCICKAGYQQKGDTCEPCGRGFYKSSSQDLQCSRC<u>PTHS</u> | 300 |
| Ephrin type-A receptor 7b (SEQ ID No: 2) | SAEGEWLVPIGKCICKAGYQQKGDTCEPCGRGFYKSSSQDLQCSRC<u>PTHS</u> | 300 |
| | ************************************************** | |
| Ephrin type-A receptor 7a (SEQ ID No: 1) | <u>FSDKEGSSRCECEDGYYRAPSDPPYVACTRPPSAPQNLIFNINQTTVSLE</u> | 350 |
| Ephrin type-A receptor 7b (SEQ ID No: 2) | <u>FSDKEGSSRCECEDGYYRAPSDPPYVACTRPPSAPQNLIFNINQTTVSLE</u> | 350 |
| | ************************************************** | |
| Ephrin type-A receptor 7a (SEQ ID No: 1) | WSPPADNGGRNDVTYRILCKRCSWEQGECVPCGSNIGYMPQQTGLEDNYV | 400 |
| Ephrin type-A receptor 7b (SEQ ID No: 2) | WSPPADNGGRNDVTYRILCKRCSWEQGECVPCGSNIGYMPQQTGLEDNYV | 400 |
| | ****************************************** | |
| Ephrin type-A receptor 7a (SEQ ID No: 1) | TVMDLLAHANYTFEVEAVNGVSDLSRSQRLFAAVSITTGQAAPSQVSGVM | 450 |
| Ephrin type-A receptor 7b (SEQ ID No: 2) | TVMDLLAHANYTFEVEAVNGVSDLSRSQRLFAAVSITTGQAAPSQVSGVM | 450 |
| | ************************************************** | |
| Ephrin type-A receptor 7a (SEQ ID No: 1) | KERVLQRSVELSWQEPEHPNGVITEYEIKYYEKDQRERTYSTVKTKSTSA | 500 |
| Ephrin type-A receptor 7b (SEQ ID No: 2) | KERVLQRSVELSWQEPEHPNGVITEYEIKYYEKDQRERTYSTVKTKSTSA | 500 |
| | ************************************************** | |
| Ephrin type-A receptor 7a (SEQ ID No: 1) | SINNLKPGTVYVFQIRAFTAAGYGNYSPRLDVATLEEATGKMFEATAVSS | 550 |
| Ephrin type-A receptor 7b (SEQ ID No: 2) | SINNLKPGTVYVFQIRAFTAAGYGNYSPRLDVATLEEAT-----ATAVSS | 545 |
| | **************************************       ***** | |
| Ephrin type-A receptor 7a (SEQ ID No: 1) | EQNPVIIAVVAVAGTIILVFMVFGFIIGRRHCGYSKADQEGDEELYFHF | 600 |
| Ephrin type-A receptor 7b (SEQ ID No: 2) | EQNPVIIAVVAVAGTIILVFMVFGFIIGRRHCGYSKADQEGDEELYFHF | 595 |
| | ************************************************* | |
| Ephrin type-A receptor 7a (SEQ ID No: 1) | KFPGTKTYIDPETYEDPNRAVHQFAKELDASCIKIERVIGAGEFGEVCSG | 650 |
| Ephrin type-A receptor 7b (SEQ ID No: 2) | KFPGTKTYIDPETYEDPNRAVHQFAKELDASCIKIERVIGAGEFGEVCSG | 645 |
| | ************************************************** | |

FIG 1H

| | | |
|---|---|---|
| Ephrin type-A receptor 7a (SEQ ID No: 1) | RLKLPGKRDVAVAIKTLKVGYTEKQRRDFLCEASIMGQFDHPNVVHLEGV | 700 |
| Ephrin type-A receptor 7b (SEQ ID No: 2) | RLKLPGKRDVAVAIKTLKVGYTEKQRRDFLCEASIMGQFDHPNVVHLEGV | 695 |

```
Ephrin type-A receptor 7a (SEQ ID No: 1)    VTRGKPVMIVIEFMENGALDAFLRKHDGQFTVIQLVGMLRGIAAGMRYLA 750
Ephrin type-A receptor 7b (SEQ ID No: 2)    VTRGKPVMIVIEFMENGALDAFLRKHDGQFTVIQLVGMLRGIAAGMRYLA 745

Ephrin type-A receptor 7a (SEQ ID No: 1)    DMGYVHRDLAARNILVNSNLVCKVSDFGLSRVIEDDPEAVYTTTGGKIPV 800
Ephrin type-A receptor 7b (SEQ ID No: 2)    DMGYVHRDLAARNILVNSNLVCKVSDFGLSRVIEDDPEAVYTTTGGKIPV 795

Ephrin type-A receptor 7a (SEQ ID No: 1)    RWTAPEAIQYRKFTSASDVWSYGIVMWEVMSYGERPYWDMSNQDVIKAIE 850
Ephrin type-A receptor 7b (SEQ ID No: 2)    RWTAPEAIQYRKFTSASDVWSYGIVMWEVMSYGERPYWDMSNQDVIKAIE 845

Ephrin type-A receptor 7a (SEQ ID No: 1)    EGYRLPAPMDCPAGLHQLMLDCWQKERAERPKFEQIVGILDKMIRNPNSL 900
Ephrin type-A receptor 7b (SEQ ID No: 2)    EGYRLPAPMDCPAGLHQLMLDCWQKERAERPKFEQIVGILDKMIRNPNSL 895

Ephrin type-A receptor 7a (SEQ ID No: 1)    KTPLGTCSRPISPLLDQNTPDFTTFCSVGEWLQAIKMERYKDNFTAAGYN 950
Ephrin type-A receptor 7b (SEQ ID No: 2)    KTPLGTCSRPISPLLDQNTPDFTTFCSVGEWLQAIKMERYKDNFTAAGYN 945

Ephrin type-A receptor 7a (SEQ ID No: 1)    SLESVARMTIEDVMSLGITLVGHQKKIMSSIQTMRAQMLHLHGTGIQV 998
Ephrin type-A receptor 7b (SEQ ID No: 2)    SLESVARMTIEDVMSLGITLVGHQKKIMSSIQTMRAQMLHLHGTGIQV 993
```

Mass Match Peptides (bold):

Tandem Peptides (underline):
CPTHSFSDK [6]

METHOD FOR TREATING CANCER BY ADMINISTERING ANTIBODY TO EPHRIN TYPE-A RECEPTOR 7

CROSS-REFERENCE TO RELATED APPLICATIONS

This application is a U.S. National Phase of PCT Patent Application No. PCT/IB2009/005884 filed Jun. 9, 2009 and claims priority to Provisional Patent Application No. 61/060,067 filed Jun. 9, 2008 the disclosures of which are incorporated herein by reference in their entirety for all purposes.

INTRODUCTION

The present invention relates to the identification of membrane protein associated with bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer which has utility as a marker for bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer metastases and which also forms a biological target against which therapeutic antibodies (or other affinity reagents) or other pharmaceutical agents can be made, formulations/compositions comprising said protein/polypeptide, use of said protein/polypeptide or a composition comprising same in therapy, antibodies for use in therapy, compositions comprising a therapeutic antibody against a relevant polypeptide or a combination of antibodies and use of same in therapy. The invention also extends to use of the relevant protein, fragments thereof or antibodies directed against the same for diagnosis of one or more of bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer and kits comprising said protein, fragments or antibodies and use of said kits in methods of diagnosis.

BACKGROUND OF THE INVENTION

Bladder Cancer

In the United States, bladder cancer is the fourth most common type of cancer in men and the ninth most common cancer in women. More than 51,000 men and 17,000 women are diagnosed with bladder cancer each year, with around 14,000 deaths in total. One reason for its higher incidence in men is that the androgen receptor, which is much more active in men than in women, plays a major part in the development of the cancer.

Incidence of bladder cancer increases with age. People over the age of 70 develop the disease 2 to 3 times more often than those aged 55-69 and 15 to 20 times more often than those aged 30-54. Bladder cancer is 2 to 3 times more common in men. Smoking is a major contributory factor, accounting for up to 65 percent of cases in men and 30 percent of cases in women in developed countries.

It has been estimated that approximately US$2 billion is spent in the United States on treating bladder cancer. The NCI's investment in bladder cancer research has increased from US$19.1 million in 2000 to an estimated US$34.8 million in 2005.

Bladder Cancer Diagnosis

Most patients when first diagnosed with bladder cancer have their cancer confined to the bladder (74%). In 19% of the cases, the cancer has spread to nearby tissues outside the bladder and in 3% it has spread to distant sites.

Bladder cancer can be diagnosed using cystoscopy, biopsy, urine cytology and imaging tests such as an intravenous pyelogram (IVP), computed tomography (CT) scan, magnetic resonance imaging (MRI) scan or ultrasound.

Bladder Cancer Staging

Bladder cancer is staged using the American Joint Committee on Cancer (AJCC) TNM system—stage I-IV.

Bladder Cancer Treatment

The main types of treatment for bladder cancer are surgery, radiation therapy, immunotherapy and chemotherapy. Surgery, alone or combined with other treatments, is used in more than 90% of cases. For early stage or superficial bladder cancer, a transurethral resection (TUR) is most common. About 70-80% of patients have superficial cancer when first diagnosed. When the bladder cancer is invasive, a cystectomy is sometimes necessary. An alternative approach for locally advanced bladder cancer can be a TUR along with radiation therapy and chemotherapy.

*Bacillus* Calmette-Guerin (BCG) can be used as immunotherapy for treating low-stage bladder cancer.

Neoadjuvant or adjuvant chemotherapy can be used in the treatment of bladder cancer. Mitomycin and thiotepa are the drugs most often used for intravesical chemotherapy. Systemic chemotherapy combinations used to treat bladder cancer include M-VAC (methotrexate, vinblastine, doxorubicin and cisplatin), MCV (methotrexate, cisplatin and vinblastine) and GemCIS (gemcitabine and cisplatin).

External beam radiation therapy or local or interstitial radiation therapy can be combined with chemotherapy after surgery.

Bladder Cancer Survival by Stage:

| Stage | Relative 5-year Survival Rate |
|---|---|
| 0 | 95% |
| I | 85% |
| II | 55% |
| III | 38% |
| IV | 16% |

Breast Cancer

Globally, breast cancer is both the most common cancer (10% of all cancer cases) and the leading cause of cancer death (6% of cancer deaths) in women. Global incidence of breast cancer is over 1 million cases per year, with about 400,000 deaths. Women in North America have the highest rate of breast cancer in the world (over 200,000 new cases per year, with about 40,000 deaths). The chance of developing invasive breast cancer at some time in a woman's life is about 1 in 8. Breast cancer incidence increases with age, rising sharply after age 40. In the USA, about 77% of invasive breast cancers occur in women over age 50. It has been estimated that approximately US$8.1 billion is spent in the USA each year on treating breast cancer.

Breast Cancer Diagnosis

Early diagnosis improves the likelihood that treatment will be successful. Screening methods such as mammograms, clinical breast examinations and breast self-examinations are useful in detecting breast cancer. Current diagnostic methods include breast ultrasound, ductogram, full-field digital mammography (FFDM), scintimammography and MRI. A biopsy (fine needle aspiration biopsy, core biopsy or surgical biopsy)

is then performed to confirm the presence of breast cancer. Imaging tests such as a chest x-ray, bone scan, CT, MRI and PET are used to detect if the breast cancer has spread.

Breast Cancer Staging

Breast cancer is staged using the American Joint Committee on Cancer (AJCC) TNM system—Stage 0-Stage IV. Ductal carcinoma in situ (DCIS), a non-invasive cancer which accounts for 20% of new breast cancer cases is Stage 0. Nearly all women diagnosed at this early stage of breast cancer can be cured. Infiltrating (invasive) ductal carcinoma (IDC), which accounts for 80% of invasive breast cancer and infiltrating (invasive) lobular carcinoma (ILC), which accounts for 5% of invasive breast cancers are more severe Stage I-IV cancers and can metastasize.

Breast Cancer Treatment

Breast-conserving surgery (lumpectomy) or mastectomy are the usual treatments for breast cancer. For stage I or II breast cancer, breast-conserving surgery is as effective as mastectomy. Patients can then undergo reconstructive surgery. Axillary lymph node sampling and removal or sentinel lymph node biopsy (SLNB) is performed to see if the cancer has spread to the lymph nodes.

Neoadjuvant chemotherapy can be given before surgery to shrink large cancers. Adjuvant chemotherapy after surgery reduces the risk of breast cancer recurrence. Chemotherapy can also be used as the main treatment for women whose cancer has spread outside the breast and underarm area. Chemotherapeutic agents used include anthracyclines (e.g. methotrexate, fluorouracil, doxorubicin, epirubicin), taxanes (e.g. paclitaxel, docetaxel, vinorelbine) and alkylating agents (e.g. cyclophosphamide).

Radiation therapy (usually external beam radiation but sometimes brachytherapy) is given once chemotherapy is complete.

Hormone therapy with selective estrogen receptor modulators (e.g. tamoxifen) can be given to women with estrogen receptor positive breast cancers. Taking tamoxifen after surgery for 5 years can reduce recurrence by about 50% in women with early breast cancer. Aromatase inhibitors such as exemestane, letrozole or anastrozole can also be used.

Women with HER2 positive cancers (about 1/3 of breast cancers) can be given biological response modifiers such as trastuzumab (Herceptin). Clinical trials have shown that adding trastuzumab to chemotherapy lowers the recurrence rate and death rate over chemotherapy alone after surgery in women with HER2 positive early breast cancers.

Breast Cancer Survival by Stage

Patients diagnosed with breast cancer between 1995 and 1998 had a 5 year relative survival rate of 100% for stage 0 and I, 92% for stage IIA, 81% for stage IIB, 67% for stage IIIA, 54% for stage IIIB and 20% for stage IV.

Colorectal Cancer

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis

Today, the fecal occult blood test and colonoscopy, a highly invasive procedure, are the most frequently used screening and diagnostic methods for colorectal cancer. Other diagnostic tools include Flexible Sigmoidoscopy (allowing the observation of only about half of the colon) and Double Contrast Barium Enema (DCBE, to obtain X-ray images).

Colorectal Cancer Staging

CRC has four distinct stages: patients with stage I disease have a five-year survival rate of >90%, while those with metastatic stage IV disease have a <5% survival rate according to the US National Institutes of Health (NIH).

Colorectal Cancer Treatment

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep vein thrombosis and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognised that the majority of CRC tumours develop in a series of well-defined stages from benign adenomas.

Colorectal Cancer Survival by Stage:

For stage I 93%, for stage IIA 85%, for stage IIB 72%, for stage IIIA 83%, for stage IIIB 64%, for stage IIIC 44% and for stage IV 8%.

Gastric Cancer

Gastric cancer is the second-leading cause of cancer-related deaths in the world, with about 700,000 deaths per year, mostly in less developed countries. In the USA, about 22,000 people are diagnosed with gastric cancer each year, with about 11,000 deaths. This figure is approximately ten times higher in Japan. Two thirds of people diagnosed with gastric cancer are older than 65.

Gastric Cancer Diagnosis

Early stage gastric cancer rarely causes symptoms so only about 10-20% of gastric cancers in the USA are found in the early stages, before they have spread to other areas of the body. Studies in the USA have not found mass screening for gastric cancer to be useful because the disease is not that common. Endoscopy followed by a biopsy is the main procedure used to diagnose gastric cancer. Other diagnostic methods include barium upper gastrointestinal radiographs, endoscopic ultrasound, CT scan, PET scan, MRI scan, chest x-ray, laparoscopy, complete blood count (CBC) test and fecal occult blood test.

Gastric Cancer Staging

Gastric cancer is staged using the American Joint Commission on Cancer (AJCC) TNM system—Stage 0-Stage IV. Patients with stage 0 disease have a 5-year survival rate of >90%, while there is usually no cure for patients with stage IV disease where the 5-year survival rate is only 7%. The overall 5-year relative survival rate of people with gastric cancer in the USA is about 23%. The 5-year survival rate for cancers of the proximal stomach is lower than for cancers in the distal stomach.

Gastric Cancer Treatment

Surgery is the only way to cure gastric cancer. There are three types of surgery used—endoscopic mucosal resection (only for early stage gastric cancer), subtotal gastrectomy or total gastrectomy. Gastric cancer often spreads to lymph nodes so these must also be removed. If the cancer has extended to the spleen, the spleen is also removed. Surgery for gastric cancer is difficult and complications can occur.

Chemotherapy may be given as the primary treatment for gastric cancer that has spread to distant organs. Chemotherapy together with external beam radiation therapy may delay cancer recurrence and extend the life span of people with less advanced gastric cancer, especially when the cancer could not be removed completely by surgery. Chemotherapeutic agents used include fluorouracil, doxorubicin, methotrexate, etoposide and cisplatin. More recently, imatinib mesylate (Gleevec) has been trialled in gastrointestinal stromal tumours (GIST), improving progression free survival.

Gastric Cancer Survival by Stage:

For stage 0 greater than 90%, for stage IA 80% for stage IB 60%, for stage II 34%, for stage IIIA 17%, for stage IIIB 12% and stage IV 7%.

Head and Neck Cancer

The term head and neck cancer refers to a group of biologically similar cancers originating from the upper aerodigestive tract, including the lip, oral cavity (mouth), nasal cavity, paranasal sinuses, pharynx, and larynx. Most head and neck cancers are squamous cell carcinomas, originating from the mucosal lining (epithelium) of these regions. Head and neck cancers often spread to the lymph nodes of the neck, and this is often the first manifestation of the disease at the time of diagnosis.

The number of new cases of head and neck cancers in the United States was 40,490 in 2006, accounting for about 3% of adult malignancies. 11,170 patients died of their disease in 2006. The worldwide incidence exceeds half a million cases annually. 85% of head and neck cancers are linked to tobacco use. In North America and Europe, the tumours usually arise from the oral cavity, oropharynx, or larynx, whereas nasopharyngeal cancer is more common in the Mediterranean countries and in the Far East. In Southeast China and Taiwan, head and neck cancer, specifically nasopharyngeal cancer is the most common cause of death in young men. African Americans are disproportionately affected by head and neck cancer, with younger ages of incidence, increased mortality, and more advanced disease at presentation.

Head and Neck Cancer Diagnosis

Head and neck cancer is diagnosed using a combination of tests which can include a physical examination, endoscopy, X-ray, computed tomography (CT) scan, magnetic resonance imaging (MRI) scan, PET scan and a biopsy. Early signs of head and neck cancer are often not detected and the majority of head and neck cancer patients present with advanced disease and often have secondary tumours.

Head and Neck Cancer Staging

Head and neck cancer is staged using the American Joint Committee on Cancer (AJCC) TNM system—stage I-IV. The 5-year survival for all stages of head and neck cancer is 35-50%, due, in part, to late presentation. Stage I and II survival rates range from 40-95% and stage III and IV survival rates range from 0-50%. It is predicted that at least one third of patients with head and neck cancer will ultimately die as a result of their disease. The 5-year mortality rate has not altered significantly in the last few decades, despite advances in treatment modalities.

Head and Neck Cancer Treatment

Surgery and radiation therapy are the primary modalities of therapy, often in combination. Chemotherapy can be used as an induction therapy or as an adjuvant to radiation therapy, with or without surgery.

Kidney Cancer

Kidney cancer accounts for about 1.9% of cancer cases globally and 1.5% of deaths. Global incidence of kidney cancer is around 208,000 cases, with over 100,000 deaths. The incidence of kidney cancer is much higher in developed countries, being the sixth most common form of cancer in Western Europe. Around 38,900 new cases of kidney cancer are diagnosed in the USA each year, with around 12,800 deaths. It is very uncommon under age 45, and its incidence is highest between the ages of 55 and 84. The rate of people developing kidney cancer has been increasing at about 1.5% per year but the death rate has not been increasing. Renal cell carcinoma accounts for more than 90% of malignant kidney tumours. It has been estimated that approximately US$1.9 billion is spent in the USA each year on treating kidney cancer.

Kidney Cancer Diagnosis

Many renal cell cancers are found at a late stage; they can become quite large without causing any pain or discomfort and there are no simple tests that can detect renal cell cancer early. About 25% of patients with renal cell carcinoma will already have metastatic spread of their cancer when they are diagnosed.

Renal cell cancer can often be diagnosed without the need for a biopsy using a CT scan, MRI, ultrasound, positron emission tomography (PET) scan, intravenous pyelogram (IVP) and/or angiography. Fine needle aspiration biopsy may however be valuable when imaging results are not conclusive enough to warrant removing a kidney.

Kidney Cancer Staging

Renal cell cancers are usually graded on a scale of 1-4. Renal cell cancer is also staged using the American Joint Committee on Cancer (AJCC) TNM system—stage I-IV. The University of California Los Angeles Integrated Staging System can also be used, which divides patients without any tumour spread into three groups—low risk, intermediate risk and high risk. The 5-year cancer-specific survival for the low-risk group is 91%, for the intermediate-risk group is 80%, and for the high-risk group is 55%. Patients with tumour spread are also divided into three groups—low, intermediate and high risk. The 5-year cancer-specific survival for the low-risk group is 32%, for the intermediate-risk group 20% and for the high-risk group 0%.

Kidney Cancer Treatment

Surgery by radical nephrectomy (and sometimes regional lymphadenectomy), partial nephrectomy or laparoscopic nephrectomy is the main treatment for renal cell carcinoma. Renal cell carcinomas are not very sensitive to radiation so using radiation therapy before or after removing the cancer is not routinely recommended because studies have shown no improvement in survival rates.

Renal cell cancers are very resistant to present forms of chemotherapy. Some drugs, such as vinblastine, floxuridine, and 5-fluorouracil (5-FU) are mildly effective. A combination of 5-FU and gemcitabine has benefited some patients. A 5-FU-like drug, capecitabine, may also have some benefit.

Cytokines (interleukin-2 (IL-2) and interferon-alpha) have become one of the standard treatments for metastatic renal cell carcinoma. These cause the cancers to shrink to less than half their original size in about 10% to 20% of patients. Patients who respond to IL-2 tend to have lasting responses. Recent research with a combination of IL-2, interferon, and chemotherapy (using 5-fluorouracil) is also promising and may offer a better chance of partial or complete remission. Cytokine therapy does have severe side affects however.

Sorafenib (Nexavar), Sunitinib (Sutent) and Bevacizumab (Avastin) are other drugs which may also be effective against renal cell cancer.

Kidney Cancer Survival by Stage

| T stage cancer | 5/10-year cancer-specific survival |
|---|---|
| T1 | 95%/91% |
| T2 | 80%/70% |
| T3a | 66%/53% |
| T3b | 52%/43% |
| T3c | 43%/42% |

Lung Cancer

Lung cancer is the most common form of cancer worldwide (accounting for about 12% of cancer cases) and the main cause of death from cancer (accounting for about 18% of deaths).

Global incidence of lung cancer is over 1,300,000 per year, with the number of deaths over 1,100,000. In the USA, there are about 170,000 new cases per year (about 13% of all cancers), with about 160,000 deaths (about 28% of cancer deaths). Lung cancer is much more prevalent among men than women. Nearly 70% of people diagnosed with lung cancer are older than 65; fewer than 3% of all cases are found in people under the age of 45. Around 15% of all lung cancers are small cell type (SCLC), which tend to spread widely through the body, while the remaining 85% are non-small cell (NSCLC). It has been estimated that approximately US$9.6 billion is spent in the USA each year on treating lung cancer.

Lung Cancer Diagnosis

Lung cancer is a life-threatening disease because it often metastasises even before it can be detected on a chest x-ray. Usually symptoms of lung cancer do not appear until the disease is in an advanced stage. So far, there is no screening test that has been shown to improve a person's chance for a cure. Imaging tests such as a chest x-ray, CT scan, MRI scan or PET scan may be used to detect lung cancer. Tests to confirm the diagnosis are then performed and include sputum cytology, needle biopsy, bronchoscopy, endobronchial ultrasound and complete blood count (CBC).

Lung Cancer Staging

Nearly 60% of people diagnosed with lung cancer die within one year of diagnosis; 75% die within 2 years. The 5-year survival rate for people diagnosed with NSCLC is about 15%; for SCLC the 5-year survival rate is about 6%. NSCLC is staged using the American Joint Committee on Cancer (AJCC) TNM system—Stage 0-Stage IV. The 5-year survival rates by stage are as follows: stage I: 47%; stage II; 26%; stage III: 8% and stage IV: 2%. SCLC has a 2-stage system—limited stage and extensive stage. About two thirds of SCLC patients have extensive disease at diagnosis. If SCLC is found very early and is localised to the lung alone, the 5-year survival rate is around 21%, but only 6% of patients fall into this category. Where the cancer has spread, the 5-year survival is around 11%. For patients with extensive disease, the 5-year survival is just 2%.

Lung Cancer Treatment

Surgery is the only reliable method to cure NSCLC. Types of surgery include lobectomy, pneumonectomy, segmentectomy and video-assisted thoracic surgery (for small tumours).

External beam radiation therapy is sometimes used as the primary treatment, especially if the patient's health is too poor to undergo surgery. Radiation therapy can also be used after surgery. Chemotherapy may be given as the primary treatment or as an adjuvant to surgery. Targeted therapy using epidermal growth factor receptor (EGFR) antagonists such as gefitinib or erlotinib can also be given after other treatments have failed. Antiangiogenic drugs, such as bevacizumab, have been found to prolong survival of patients with advanced lung cancer. Photodynamic therapy is also being researched as a treatment for lung cancer.

The main treatment for SCLC is chemotherapy, either alone or in combination with external beam radiation therapy and very rarely, surgery.

Chemotherapeutic agents used for NSCLC and SCLC include cisplatin, carboplatin, mitomycin C, ifosfamide, vinblastine, gemcitabine, etoposide, vinorelbine, paclitaxel, docetaxel and irinotecan.

Osteosarcoma

Osteosarcoma is the most common bone cancer in children, adolescents and young adults (accounting for approximately 5% of childhood tumours) but it is still a rare disease with an annual incidence of 2-3 per million in the general population. There are about 900 new cases of osteosarcoma diagnosed in the United States each year (about 400 of which occur in children and adolescents younger than 20 years old), with approximately 300 deaths each year. Osteosarcoma is a primary malignant tumour of the appendicular skeleton that is characterized by the direct formation of bone or osteoid tissue by the tumour cells. In children and adolescents, more than 50% of these tumours arise from the bones around the knee. Many people with osteosarcoma can be cured but not all and the price of cure even with the most modern treatments is high.

Osteosarcoma Diagnosis

Diagnostic methods for osteosarcoma include an X-ray, bone scan, CT scan, PET scan and MRI of the affected area. A CT scan of the chest is also conducted to see if the cancer has spread to the lungs. Blood tests can be used to detect serum levels of alkaline phosphatase and/or LDH, which are increased in a considerable number of osteosarcoma patients, although serum levels do not correlate reliably with disease extent. The diagnosis of osteosarcoma must be verified histologically with a core needle biopsy or open biopsy. Micrometastatic disease is present at diagnosis in 80-90% of patients but undetectable with any of present tests.

Osteosarcoma Staging

There are two staging systems for osteosarcoma: the Enneking system where low-grade tumours are stage I, high-grade tumours are stage II, and metastatic tumours (regardless of grade) are stage III and the American Joint Commission on Cancer (AJCC) system which stages osteosarcoma from IA to IVB.

There are essentially 2 categories of patients: those who present without clinically detectable metastatic disease (localized osteosarcoma) and the 15-20% of patients who present with clinically detectable metastatic disease (metastatic osteosarcoma). 85% to 90% of metastatic disease is in the lungs.

Osteosarcoma has one of the lowest survival rates for pediatric cancer. The overall 5-year survival rate for patients with non-metastatic osteosarcoma is over 70%. The 5-year survival rate for patients whose cancers have already metastasised at the time of their diagnosis is about 30%.

Osteosarcoma Treatment

Once osteosarcoma has been diagnosed, the correct treatment needs to be selected. Successful treatment generally requires the combination of effective systemic chemotherapy and complete resection (amputation, limb preservation, or rotationplasty) of all clinically detectable disease (including resection of all overt metastatic disease). Protective weight bearing is recommended for patients with tumours of weight-bearing bones to prevent pathological fractures that could preclude limb-preserving surgery.

At least 80% of patients with localized osteosarcoma treated with surgery alone will develop metastatic disease. Randomized clinical trials have established that adjuvant chemotherapy is effective in preventing relapse or recurrence in patients with localized resectable primary tumours. The chemotherapeutic agents used include high-dose methotrexate, doxorubicin, cisplatin, high-dose ifosfamide, etoposide, carboplatin, cyclophosphamide, actinomycin D and bleomycin. Bone-seeking radioactive chemicals are sometimes used to treat osteosarcoma. Samarium-153 may be given in addition to external beam radiation therapy.

There is no difference in overall survival (OS) between patients initially treated by amputation and those treated with a limb-sparing procedure. In general, more than 80% of patients with extremity osteosarcoma can be treated by a limb-sparing operation and do not require amputation. Complications of limb-salvage surgery include infection and grafts or rods that become loose or broken. Limb-salvage surgery patients may need more surgery during the following 5 years, and some may eventually need an amputation. Limb length inequality is also a major potential problem for young children. Treatment options include extensible prostheses, amputation, and rotationplasty for these children.

Most recurrences of osteosarcoma develop within 2 to 3 years after treatment completion. Fewer than 30% of patients with localized resectable primary tumours treated with surgery alone can be expected to survive free of relapse. Recurrence of osteosarcoma is most often in the lung.

The ability to achieve a complete resection of recurrent disease is the most important prognostic factor at first relapse, with a 5-year survival rate of 20% to 45% following complete resection of metastatic pulmonary tumours and 20% following complete resection of metastases at other sites. Repeated resections of pulmonary recurrences can lead to extended disease control and possibly cure for some patients. Survival for patients with unresectable metastatic disease is less than 5%. Resection of metastatic disease followed by observation alone results in low overall and disease-free survival.

Pancreatic Cancer

Pancreatic cancer is a very difficult cancer to detect and the prognosis for patients is usually very poor. The number of new cases and deaths per year is almost equal. Global incidence of pancreatic cancer is approximately 230,000 cases (about 2% of all cancer cases), with about 225,000 deaths (3.4% of cancer deaths) per year. It is much more prevalent in the developed world. In the USA, there are about 34,000 new cases per year, with about 32,000 deaths. It has been estimated that approximately US$1.5 billion is spent in the USA each year on treating pancreatic cancer.

Pancreatic Cancer Diagnosis

Pancreatic cancer is very difficult to detect and very few pancreatic cancers are found early. Patients usually have no symptoms until the cancer has spread to other organs. There are currently no blood tests or easily available screening tests that can accurately detect early cancers of the pancreas. An endoscopic ultrasound followed by a biopsy is the best way to diagnose pancreatic cancer. Other detection methods include CT, CT-guided needle biopsy, PET, ultrasonography and MRI. Blood levels of CA 19-9 and carcinoembryonic antigen (CEA) may be elevated but by the time blood levels are high enough to be detected, the cancer is no longer in its early stages.

Pancreatic Cancer Staging

Pancreatic cancer has four stages, stage I to stage IV according to the American Joint Committee on Cancer (AJCC) TNM system. Pancreatic cancer is also divided into resectable, locally advanced (unresectable) and metastatic cancer. For patients with advanced cancers, the overall survival rate is <1% at 5 years with most patients dying within 1 year.

Pancreatic Cancer Treatment

Surgery is the only method of curing pancreatic cancer. About 10% of pancreatic cancers are contained entirely within the pancreas at the time of diagnosis and attempts to remove the entire cancer by surgery may be successful in some of these patients. The 5-year survival for those undergoing surgery with the intent of completely removing the cancer is about 20%. Potentially curative surgery, usually by pancreaticoduodenectomy (Whipple procedure), is used when it may be possible to remove all of the cancer. Palliative surgery may be performed if the tumour is too widespread to be completely removed. Removing only part of the cancer does not allow patients to live longer. Pancreatic cancer surgery is difficult to perform with a high likelihood of complications.

External beam radiation therapy combined with chemotherapy can be given before or after surgery and can also be given to patients whose tumours are too widespread to be removed by surgery. The main chemotherapeutic agents which are used are gemcitabine and 5-fluorouracil. Targeted therapy using drugs such as erlotinib and cetuximab may be of benefit to patients with advanced pancreatic cancer.

Prostate Cancer

Prostate cancer is the third most common cancer in the world amongst men and it accounts for 5.4% of all cancer cases globally and 3.3% of cancer-related deaths. Global incidence of prostate cancer is around 680,000 cases, with about 221,000 deaths. In the USA, prostate cancer is the most common cancer, other than skin cancers, in American men. About 234,460 new cases of prostate cancer are diagnosed in the USA each year. About 1 man in 6 will be diagnosed with prostate cancer during his lifetime, but only 1 in 34 will die of it. A little over 1.8 million men in the USA are survivors of prostate cancer. The risk of developing prostate cancer rises significantly with age and 60% of cases occur in men over the age of 70. Prostate cancer is the second leading cause of cancer death in American men. Around 27,350 men in the USA die of prostate cancer each year. Prostate cancer accounts for about 10% of cancer-related deaths in men. Modern methods of detection and treatment mean that prostate cancers are now found earlier and treated more effectively. This has led to a yearly drop in death rates of about 3.5% in-recent years. Prostate cancer is most common in North America and northwestern Europe. It is less common in Asia, Africa, Central America, and South America. It has been estimated that approximately US$8.0 billion is spent in the USA each year on treating prostate cancer.

Prostate Cancer Diagnosis

Prostate cancer can often be found early by testing the amount of prostate-specific antigen (PSA) in the blood. A digital rectal exam (DRE) can also be performed. However, there are potential problems with the current screening methods. Neither the PSA test nor the DRE is 100% accurate. A core needle biopsy is the main method used to diagnose prostate cancer. A transrectal ultrasound (TRUS) may be used during a prostate biopsy.

Prostate Cancer Staging

Prostate cancers are graded according to the Gleason system, graded from 1-5, which results in the Gleason score, from 1-10. Prostate cancer is staged using the American Joint Committee on Cancer (AJCC) TNM system and combined with the Gleason score to give stages from I-IV.

Ninety one percent of all prostate cancers are found in the local and regional stages; the 5-year relative survival rate for these men is nearly 100%. The 5-year relative survival rate for men whose prostate cancers have already spread to distant parts of the body at the time of diagnosis is about 34%.

Prostate Cancer Treatment

Because prostate cancer often grows very slowly, some men never have treatment and expectant management is recommended. If treatment is required and the cancer is not thought to have spread outside of the gland, a radical prostatectomy can be performed. Transurethral resection of the prostate (TURP) can be performed to relieve symptoms but not to cure prostate cancer.

External beam radiation therapy (three-dimensional conformal radiation therapy (3DCRT), intensity modulated radiation therapy (IMRT) or conformal proton beam radiation therapy) or brachytherapy can also be used as treatment.

Cryosurgery is sometimes used to treat localized prostate cancer but as not much is known about the long-term effectiveness of cryosurgery, it is not routinely used as a first treatment for prostate cancer. It can be used for recurrent cancer after other treatments.

Androgen deprivation therapy (ADT) (orchiectomy or luteinizing hormone-releasing hormone (LHRH) analogs or antagonists) can be used to shrink prostate cancers or make them grow more slowly.

Chemotherapy is sometimes used if prostate cancer has spread outside of the prostate gland and is hormone therapy resistant. Chemotherapeutic agents include docetaxel, prednisone, doxorubicin, etoposide, vinblastine, paclitaxel, carboplatin, estramustine, vinorelbine. Like hormone therapy, chemotherapy is unlikely to result in a cure.

Skin Cancer

Skin cancer is the most common type of cancer, accounting for at least half of all cancers. Skin cancers that develop from melanocytes are called melanomas. Melanoma accounts for about 4% of skin cancer cases but causes a large majority of skin cancer deaths. In the USA, about 62,000 new melanomas are diagnosed each year, with around 8,000 deaths.

A much more common type of skin cancer is keratinocyte cancer which includes basal cell carcinoma and squamous cell carcinoma. Basal cell carcinomas account for about 80% of non-melanoma skin cancers and squamous cell carcinomas account for about 20%. More than 1 million basal and squamous cell skin cancers are diagnosed each year. Death from these cancers is uncommon; about 2,000 people die every year from non-melanoma skin cancers. The death rate has dropped about 30% in the past 30 years.

Skin Cancer Diagnosis

A skin biopsy is used to diagnose skin cancer. Types of skin biopsy include excisional biopsy, incisional biopsy, shave biopsy and punch biopsy. Metastatic skin cancer can be diagnosed using a number of methods including fine needle aspiration biopsy, surgical lymph node biopsy and sentinel lymph node mapping and biopsy. Imaging tests such as a chest x-ray, computed tomography (CT), magnetic resonance imaging (MRI), positron emission tomography (PET) and nuclear bone scans can also be used.

Skin Cancer Staging

Melanoma is staged using the American Joint Committee on Cancer (AJCC) TNM system—Stage 0-Stage IV. The thickness of the melanoma is measured using the Breslow measurement. Basal cell cancer rarely spreads to other organs and so it is seldomly staged. Staging using the AJCC TNM system is sometimes done for squamous cell cancers.

Skin Cancer Treatment

Most basal cell and squamous cell carcinomas can often be completely cured by fairly minor surgery including simple excision, curettage and electrodesiccation or Mohs surgery (microscopically-controlled surgery). Cryotherapy, photodynamic therapy or topical chemotherapy using 5-fluorouracil can also be used as treatment options for these skin cancers. For certain squamous cell cancers with a high risk of spreading, surgery may sometimes be followed by radiation or chemotherapy. Chemotherapeutic drugs which can be used include cisplatin, doxorubicin, fluorouracil (5-FU), and mitomycin. Radiation may be used as the primary treatment in cases where the tumour is very large or is located on an area of the skin that makes surgery difficult.

Thin melanomas can be completely cured by excision. If the melanoma is on a finger or toe, treatment may involve amputation of the digit. If the melanoma has spread to the lymph nodes, lymph node dissection may be required.

No current treatment is usually able to cure stage IV melanoma. Although chemotherapy is usually not as effective in melanoma as in some other types of cancer, it may relieve symptoms or extend survival of some patients with stage N melanoma. Chemotherapy drugs often used to treat melanoma include dacarbazine, carmustine, cisplatin, vinblastine and temozolomide. Recent studies have found that biochemotherapy, combining several chemotherapy drugs with 1 or more immunotherapy drugs may be more effective than a single chemotherapy drug alone. Immunotherapy drugs include interferon-alpha and/or interleukin-2. Radiation therapy may be used to treat recurrent melanoma and is used as palliation of metastases to the bone and brain.

Melanoma Survival By Stage

| Stage | 5-year relative survival rate | 10-year relative survival rate |
|-------|-------------------------------|--------------------------------|
| 0     | 97%                           | —                              |
| I     | 90-95%                        | 80%                            |
| IIA   | 78%                           | 64%                            |
| IIB   | 63-67%                        | 51-54%                         |
| IIC   | 45%                           | 32%                            |
| IIIA  | 63-70%                        | 57-63%                         |
| IIIB  | 46-53%                        | 38%                            |
| IIIC  | 28%                           | 15-25%                         |
| IV    | 18%                           | 14%                            |

Thyroid Cancer

The two most common types of thyroid cancer are papillary carcinoma which accounts for 80% of thyroid cancers and follicular carcinoma which accounts for 10% of thyroid cancers. These are differentiated thyroid cancers which develop from the thyroid follicular cells. Papillary carcinomas grow very slowly; they often spread to lymph nodes in the neck but most of the time, this can be successfully treated and is rarely fatal. Follicular carcinomas usually don't spread to the lymph nodes but can spread to other parts of the body, such as the lungs or bones. The prognosis is not as good as for papillary carcinoma but it still very good in most cases. Other types of thyroid cancer include Hurthle cell carcinoma, medullary thyroid carcinoma and anaplastic carcinoma all of which are less common but harder to treat and have a worse prognosis than papillary carcinoma and follicular carcinoma.

There are around 37,000 new cases of thyroid cancer each year in the United States with about 1,600 deaths. The 5-year survival rate is very good at about 97%. Thyroid cancer mainly affects younger people with around 66% of cases found in people between the ages of 20 and 55.

Thyroid Cancer Diagnosis

Thyroid cancer is diagnosed by fine needle aspiration biopsy. Imaging tests such as a chest x-ray to see if the cancer has spread to the lungs, an ultrasound, a computed tomography (CT) scan, a magnetic resonance imaging (MRI) scan or a radioiodine scan may also be performed. Blood levels of thyroid-stimulating hormone (TSH) may be checked to determine the activity of the thyroid gland. For medullary thyroid carcinoma, levels of calcitonic and carcinoembryonic antigen (CEA) are often high so this can be measured to aid in diagnosis.

Thyroid Cancer Staging

Thyroid cancer has four stages, stage I to stage IV according to the American Joint Committee on Cancer (AJCC) TNM system. Unlike most other cancers, thyroid cancers are grouped into stages in a way that takes into account both the subtype of cancer and the patient's age. For papillary or follicular thyroid carcinoma, all people under the age of 45 are either stage I or stage II. Patients 45 years and older can be stage I-IV. Stage grouping for medullary thyroid carcinoma in people of any age is the same as for papillary or follicular carcinoma in people older than age 45. All anaplastic thyroid cancers are considered stage N, reflecting the poor prognosis of this type of cancer.

Thyroid Cancer Treatment

Surgery is the main treatment for thyroid cancer and is used in almost every case, except some anaplastic thyroid cancers. Lobectomy can be used for small differentiated thyroid cancers but thyroidectomy is the most common surgery. Lymph node removal is performed when the cancer has spread outside the thyroid gland. Patients who have undergone total thyroidectomy will need to take daily thyroid hormone replacement pills.

Radioactive iodine can be used to destroy any thyroid tissue not removed by surgery or to treat thyroid cancer that has spread to lymph nodes and other parts of the body. Radioactive iodine therapy is not used to treat anaplastic and medullary thyroid carcinomas because these types of cancer do not take up iodine. External beam radiation therapy can be used in these cases.

Thyroid Cancer Survival By Stage

Relative 5-year survival rates by stage for papillary thyroid cancer are: Stage I: 100%; Stage II: 100%; Stage III: 96%; Stage IV: 45%; for follicular thyroid cancer: Stage I: 100%; Stage II: 100%; Stage III: 79%; Stage IV: 47%; for medullary thyroid cancer: Stage I: 100%; Stage II: 97%; Stage III: 78%; Stage IV: 24% and for anaplastic thyroid cancer all are stage N and the relative 5-year survival rate is around 9%.

Uterine Cancer

Endometrial cancer is the most common form of uterine cancer. It refers to several types of malignancy which arise from the endometrium, or lining of the uterus. Other types of uterine cancer, such as uterine sarcoma, develop from other tissues of the uterus. Uterine sarcoma is much less common than endometrial cancer, accounting for about 4% of cancers of the uterus. Uterine cancer is the most common gynaecologic cancer in the United States, with over 40,000 women diagnosed each year. Uterine cancer is the third most common cause of gynaecologic cancer death (behind ovarian and cervical cancer), with over 7,000 deaths per year in the United States.

Most cases of uterine cancer are found in women aged 55 and over. The average chance of a woman being diagnosed with uterine cancer during her lifetime is about one in 41.

Uterine Cancer Diagnosis

Most uterine cancers are detected at an early stage. About 90% of patients diagnosed with uterine cancer have abnormal vaginal bleeding. An endometrial biopsy is the most commonly performed test for uterine cancer, often with a hysteroscopy. Sometimes, a dilation and curettage will be performed. Imaging tests such as a transvaginal ultrasound and blood tests such as a complete blood count (CBC) and a CA 125 blood test can also be performed.

Uterine Cancer Staging

Uterine cancer is graded based on how much it looks like normal endometrium. A cancer is called grade 1 if 95% or more of the cancer forms glands similar to those of normal endometrial tissue. Grade 2 tumours have between 50% and 94% gland formations. Cancers with less than half of the tissue forming glands are given a grade of 3.

The main system used to stage uterine cancer is the FIGO (International Federation of Gynecology and Obstetrics) system, which is a surgical staging system. The FIGO system classifies the cancer in stages I through IV. The American Joint Committee on Cancer (AJCC) TNM system can also be used and the stages exactly match those in FIGO.

The overall 5-year relative survival rate is about 88%. When the cancer is found at an early stage, the 5-year survival rate is over 95%.

Uterine Cancer Treatment

A total abdominal hysterectomy with bilateral salpingo-oophorectomy is the most common therapeutic approach for uterine cancer. A radical hysterectomy is sometimes performed when the cancer has spread to the cervix. Lymph node sampling can be done at the same time as the hysterectomy. After hysterectomy, brachytherapy or external beam radiation therapy can be given. Chemotherapeutic drugs that can be used to treat endometrial cancer include doxorubicin (Adriamycin), cisplatin, carboplatin, and paclitaxel (Taxol). Ifosfamide is often used to treat carcinosarcoma.

Uterine Cancer Survival By Stage

Relative 5-year survival rates by stage for endometrial adenocarcinoma are: Stage IA: 99%; Stage IB: 99%; Stage IC: 92%; Stage II: 80%; Stage III: 60% and Stage IV: 30%. Relative 5-year survival rates for uterine carcinosarcoma are: Stage I: 70%; Stage II: 45%; Stage III: 30% and Stage IV: 15%.

Therapeutic Challenges

The major challenges in treatment of the above mentioned cancers are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer patients' stratification, for monitoring the effectiveness of treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, and for drug development for treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

We have used mass spectrometry to identify peptides generated by 1D gel electrophoresis or tagging with iTRAQ or ICAT reagents and tryptic digest of membrane proteins or lysates extracted from breast cancer, colorectal cancer, lung cancer, osteosarcoma or prostate cancer tissue samples. Peptide sequences were compared to existing protein and cDNA databases and the corresponding gene sequences identified. Immunohistohemistry was also performed and staining observed in colorectal cancer, lung cancer, bladder cancer, uterine cancer, head and neck cancer, skin cancer, kidney cancer, thyroid cancer and pancreatic cancer and metastatic breast cancer, colorectal cancer, gastric cancer, lung cancer and thyroid cancer. The protein of the invention has not been previously reported to originate from bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer cell membranes and represents a protein of new diagnostic and therapeutic value.

A first aspect of the invention is an agent capable of specific binding to Ephrin type-A receptor 7, or a fragment thereof, or a hybridising agent capable of hybridizing to nucleic acid encoding Ephrin type-A receptor 7 or an agent capable of detecting the activity of Ephrin type-A receptor 7 for use in treating, screening for, detecting and/or diagnosing disease, such as cancer, and especially bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Another aspect of the invention is Ephrin type-A receptor 7, or a fragment thereof for use in treating, screening for, detecting and/or diagnosing disease such as cancer, and especially bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Another aspect of the invention is an affinity reagent capable of specific binding to Ephrin type-A receptor 7 or a fragment thereof, for example an affinity reagent which contains or is conjugated to a detectable label or contains or is conjugated to a therapeutic moiety such as a cytotoxic moiety. The affinity reagent may, for example, be an antibody.

In some embodiments, the antibody of the present invention is selected from the group consisting of: a whole antibody, an antibody fragment, a humanized antibody, a single chain antibody, an immunoconjugate, a defucosylated antibody, and a bispecific antibody. The antibody fragment may be selected from the group consisting of: a UniBody, a domain antibody, and a Nanobody. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody, a DARPin, an Anticalin, an Avimer, a Versabody, and a Duocalin.

Another aspect of the invention is a hybridizing agent capable of hybridizing to nucleic acid encoding Ephrin type-A receptor 7, for example, a hybridizing agent which contains or is conjugated to a detectable label. One example of a hybridizing agent is an inhibitory RNA (RNAi). Other examples include anti-sense oligonucleotides and ribozymes.

The invention also provides a kit containing Ephrin type-A receptor 7 and/or one or more fragments thereof or containing one or more aforementioned affinity reagents and/or hybridizing agents or containing one or more agents capable of detecting the activity of Ephrin type-A receptor 7 together with instructions for their use in an aforementioned method. The kit may further contain reagents capable of detecting and reporting the binding of said affinity reagents and/or hybridizing agents to their binding partners.

Another aspect of the invention is a pharmaceutical composition comprising a therapeutically effective amount of an affinity reagent capable of specific binding to Ephrin type-A receptor 7 or a fragment thereof.

Another aspect of the invention is a pharmaceutically acceptable diluent or carrier and a pharmaceutical composition comprising one or more affinity reagents or hybridizing reagents as aforesaid and a pharmaceutically acceptable diluent or carrier.

In some embodiments, the present invention is a method for preparing an anti-Ephrin type-A receptor 7 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

Other aspects of the invention are directed to methods of making the antibodies of the invention, comprising the steps of: immunizing a transgenic animal comprising human immunoglobulin genes with an Ephrin type-A receptor 7 peptide; recovering B-cells from said transgenic animal; making hybridomas from said B-cells; selecting hybridomas that express antibodies that bind Ephrin type-A receptor 7; and recovering said antibodies that bind Ephrin type-A receptor 7 from said selected hybridomas.

In other embodiments, the method of making anti-Ephrin type-A receptor 7 antibodies, comprises the steps of:

immunizing a transgenic animal comprising human immunoglobulin genes with an Ephrin type-A receptor 7 peptide;

recovering mRNA from the B cells of said transgenic animal;

converting said mRNA to cDNA;

expressing said cDNA in phages such that anti-Ephrin type-A receptor 7 antibodies encoded by said cDNA are presented on the surface of said phages;

selecting phages that present anti-Ephrin type-A receptor 7 antibodies;

recovering nucleic acid molecules from said selected phages that encode said anti-Ephrin type-A receptor 7 immunoglobulins;

expressing said recovered nucleic acid molecules in a host cell; and recovering antibodies from said host cell that bind Ephrin type-A receptor 7.

Another aspect of the invention provides use of an Ephrin type-A receptor 7 polypeptide, one or more immunogenic fragments or derivatives thereof for the treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

In another aspect, the invention provides methods of treating bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, comprising administering to a patient a therapeutically effective amount of a compound that modulates (e.g., upregulates or downregulates) or complements the expression or the biological activity (or both) of the protein of the invention in patients having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, in order to (a) prevent the onset or development of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer; (b) prevent the progression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer; or (c) ameliorate the symptoms of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

According to another aspect of the invention we provide a method of detecting, diagnosing and/or screening for or monitoring the progression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or of monitoring the effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy in a subject which comprises detecting the presence or level of Ephrin type-A receptor 7, or one or more fragments thereof, or the presence or level of nucleic acid encoding Ephrin type-A receptor 7 or the presence or level of the activity of Ephrin type-A receptor 7 or which comprises detecting a change in the level thereof in said subject.

According to another aspect of the invention we provide a method of detecting, diagnosing and/or screening for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a candidate subject which comprises detecting the presence of Ephrin type-A receptor 7, or one or more fragments thereof, or the presence of nucleic acid encoding Ephrin type-A receptor 7 or the presence of the activity of Ephrin type-A receptor 7 in said candidate subject, in which either (a) the presence of an elevated level of Ephrin type-A receptor 7 or said one or more fragments thereof or an elevated level of nucleic acid encoding Ephrin type-A receptor 7 or the presence of an elevated level of Ephrin type-A receptor 7 activity in the candidate subject as compared with the level in a healthy subject or (b) the presence of a detectable level of Ephrin type-A receptor 7 or said one or more fragments thereof or a detectable level of nucleic acid encoding Ephrin type-A receptor 7 or the presence of a detectable level of Ephrin type-A receptor 7 activity in the candidate subject as compared with a corresponding undetectable level in a healthy subject indicates the presence of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in said subject.

According to another aspect of the invention we provide a method of monitoring the progression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a subject or of monitoring the effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy which comprises detecting the presence of Ephrin type-A receptor 7, or one or more fragments thereof, or the presence of nucleic acid encoding Ephrin type-A receptor 7 or the presence of the activity of Ephrin type-A receptor 7 in said candidate subject at a first time point and at a later time point, the presence of an elevated or lowered level of Ephrin type-A receptor 7 or said one or more fragments thereof or an elevated or lowered level of nucleic acid encoding Ephrin type-A receptor 7 or the presence of an elevated or lowered level of Ephrin type-A receptor 7 activity in the subject at the later time point as compared with the level in the subject at said first time point, indicating the progression or regression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or indicating the effect or non-effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy in said subject.

The presence of Ephrin type-A receptor 7, or one or more fragments thereof, or the presence of nucleic acid encoding Ephrin type-A receptor 7 or the presence of the activity of Ephrin type-A receptor 7 may, for example, be detected by analysis of a biological sample obtained from said subject.

The method of invention may typically include the step of obtaining a biological sample for analysis from said subject.

The biological sample used can be from any source such as a serum sample or a tissue sample e.g. bladder, breast, colorectal, gastric, head and neck, kidney, lung, osteoblast, pancreatic, prostate, skin, thyroid or uterine tissue. For instance, when looking for evidence of metastatic bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, one would look at major sites of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer metastasis, e.g. the prostate, uterus, vagina, bones, liver or lungs for bladder cancer; the liver, lungs and bones for breast cancer; the liver, peritoneal cavity, pelvis, retroperitoneum and lungs for colorectal cancer; the liver, lungs, brain, bones, kidneys and pancreas for gastric cancer; the lungs, bones and liver for head and neck cancer; the bones, lungs and liver for kidney cancer; the brain, liver, bones and adrenal glands for lung cancer; the lungs and other bones for osteosarcoma; the liver for pancreatic cancer; the bladder, ectum and bones for prostate cancer; the lungs, brain and bones for skin cancer; the lungs and bones for thyroid cancer; and the bladder, rectum, lungs and bones for uterine cancer.

Alternatively the presence of Ephrin type-A receptor 7, or one or more fragments thereof, or the presence of nucleic acid encoding Ephrin type-A receptor 7 or the presence of the activity of Ephrin type-A receptor 7 may be detected by analysis in situ.

In certain embodiments, methods of diagnosis described herein may be at least partly, or wholly, performed in vitro.

Suitably the presence of Ephrin type-A receptor 7, or one or more fragments thereof, or the presence of nucleic acid encoding Ephrin type-A receptor 7 or the presence of the activity of Ephrin type-A receptor 7 is detected quantitatively.

For example, quantitatively detecting may comprise:
(a) contacting a biological sample with an affinity reagent that is specific for Ephrin type-A receptor 7, said affinity reagent optionally being conjugated to a detectable label; and
(b) detecting whether binding has occurred between the affinity reagent and at least one species in the sample, said detection being performed either directly or indirectly.

Alternatively the presence of Ephrin type-A receptor 7, or one or more fragments thereof, or the presence of nucleic acid encoding Ephrin type-A receptor 7 or the presence of the activity of Ephrin type-A receptor 7 may be detected quantitatively by means involving use of an imaging technology.

In another embodiment, the method of the invention involves use of immunohistochemistry on bladder, breast, colorectal, gastric, head and neck, kidney, lung, osteoblast, pancreatic, prostate, skin, thyroid or uterine tissue sections in order to determine the presence of Ephrin type-A receptor 7, or one or more fragments thereof, or the presence of nucleic acid encoding Ephrin type-A receptor 7 or the presence of the activity of Ephrin type-A receptor 7, and thereby to localise bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer cells.

In one embodiment the presence of Ephrin type-A receptor 7 or one or more epitope-containing fragments thereof is detected, for example using an affinity reagent capable of specific binding to Ephrin type-A receptor 7 or one or more fragments thereof, such as an antibody.

In another embodiment the activity of Ephrin type-A receptor 7 is detected. Ephrin type-A receptor 7 is a receptor protein tyrosine kinase. The activity of Ephrin type-A receptor 7 is detected by measuring the phosphorylation of tyrosine, serine or threonine residues, preferably tyrosine, in response to the binding of a specific ligand. Preferably, the activity of Ephrin type-A receptor 7 is detected by measuring the phosphorylation of Ephrin type-A receptor 7 amino acid sequences in response to the binding of a specific ligand. Alternatively, one might measure the specific phosphorylation of an Ephrin type-A receptor 7-binding protein, preferably another member of the Eph family of receptor protein tyrosine kinases, in response to binding of a specific ligand to Ephrin type-A receptor 7. A description of the activities of the Eph family of receptor protein tyrosine kinases, and their respective naturally binding ligands, is contained in H. Surawska et al., *Cytokine & Growth Factor Reviews* 15:419-433, 2004.

According to another aspect of the invention there is provided a method of detecting, diagnosing and/or screening for or monitoring the progression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or of monitoring the effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy in a subject which comprises detecting the presence or level of antibodies capable of immunospecific binding to Ephrin type-A receptor 7, or one or more epitope-containing fragments thereof or which comprises detecting a change in the level thereof in said subject.

According to another aspect of the invention there is also provided a method of detecting, diagnosing and/or screening for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a subject which comprises detecting the presence of antibodies capable of immunospecific binding to Ephrin type-A receptor 7, or one or more epitope-containing fragments thereof in said subject, in which (a) the presence of an elevated level of antibodies capable of immunospecific binding to Ephrin type-A receptor 7 or said one or more epitope-containing fragments thereof in said subject as compared with the level in a healthy subject or (b) the presence of a detectable level of antibodies capable of immunospecific binding to Ephrin type-A receptor 7 or said one or more epitope-containing fragments thereof in said subject as compared with a corresponding undetectable level in a healthy subject indicates the presence of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in said subject.

One particular method of detecting, diagnosing and/or screening for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer comprises:
(a) bringing into contact with a biological sample to be tested Ephrin type-A receptor 7, or one or more epitope-containing fragments thereof; and
(b) detecting the presence of antibodies in the subject capable of immunospecific binding to Ephrin type-A receptor 7, or one or more epitope-containing fragments thereof.

According to another aspect of the invention there is provided a method of monitoring the progression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or of monitoring the effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy in a subject which comprises detecting the presence of antibodies capable of immunospecific binding to Ephrin type-A receptor 7, or one or more epitope-containing fragments thereof in said subject at a first time point and at a later time point, the presence of an elevated or lowered level of antibodies capable of immunospecific binding to Ephrin type-A receptor 7, or one or more epitope-containing fragments thereof in said subject at the later time point as compared with the level in said subject at said first time point, indicating the progression or regression of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or the effect or non-effect of an anti-bladder cancer, anti-breast cancer, anti-colorectal cancer, anti-gastric cancer, anti-head and neck cancer, anti-kidney cancer, anti-lung cancer, anti-osteosarcoma, anti-pancreatic cancer, anti-prostate cancer, anti-skin cancer, anti-thyroid cancer or anti-uterine cancer, including anti-metastatic cancer drug or therapy in said subject.

The presence of antibodies capable of immunospecific binding to Ephrin type-A receptor 7, or one or more epitope-containing fragments thereof is typically detected by analysis of a biological sample obtained from said subject (exemplary biological samples are mentioned above, e.g. the sample is a sample of bladder, breast, colorectal, gastric, head and neck, kidney, lung, osteoblast, pancreatic, prostate, skin, thyroid or uterine tissue, or else a sample of blood or saliva).

The method typically includes the step of obtaining said biological sample for analysis from said subject.

The antibodies that may be detected include IgA, IgM and IgG antibodies.

In any of the above methods, the level that may be detected in the candidate subject who has bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is 2 or more fold higher than the level in the healthy subject.

In one embodiment the cancer to be detected, prevented or treated is bladder cancer.

In another embodiment the cancer to be detected, prevented or treated is breast cancer.

In another embodiment the cancer to be detected, prevented or treated is colorectal cancer.

In another embodiment the cancer to be detected, prevented or treated is gastric cancer.

In another embodiment the cancer to be detected, prevented or treated is head and neck cancer.

In another embodiment the cancer to be detected, prevented or treated is kidney cancer.

In another embodiment the cancer to be detected, prevented or treated is lung cancer.

In another embodiment the cancer to be detected, prevented or treated is osteosarcoma.

In another embodiment the cancer to be detected, prevented or treated is pancreatic cancer.

In another embodiment the cancer to be detected, prevented or treated is prostate cancer.

In another embodiment the cancer to be detected, prevented or treated is skin cancer.

In another embodiment the cancer to be detected, prevented or treated is thyroid cancer.

In another embodiment the cancer to be detected, prevented or treated is uterine cancer.

In another embodiment the cancer to be detected, prevented or treated is metastatic cancer.

Other aspects of the present invention are set out below and in the claims herein.

BRIEF DESCRIPTION OF THE FIGURES

FIGS. 1A-1H show the amino acid sequences of the two isoforms of the protein of the invention. The tryptic peptides detected experimentally by mass spectrometry are highlighted—mass match peptides are shown in bold, tandem peptides are underlined.

DETAILED DESCRIPTION OF THE INVENTION

The invention described in detail below encompasses the administration of therapeutic compositions to a mammalian subject to treat or prevent bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. The invention also provides methods and compositions for clinical screening, diagnosis and prognosis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a mammalian subject, for identifying patients most likely to respond to a particular therapeutic treatment, for monitoring the results of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer therapy, for drug screening and drug development.

In one aspect the invention provides an agent capable of specific binding to Ephrin type-A receptor 7, or a fragment thereof, or a hybridising agent capable of hybridizing to nucleic acid encoding Ephrin type-A receptor 7 or an agent capable of detecting the activity of Ephrin type-A receptor 7 for use in treating, screening for, detecting and/or diagnosing disease, such as cancer, and especially bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Another aspect of the invention is an affinity reagent capable of specific binding to Ephrin type-A receptor 7 or a fragment thereof, for example an affinity reagent which contains or is conjugated to a detectable label or contains or is conjugated to a therapeutic moiety such as a cytotoxic moiety. The affinity reagent may, for example, be an antibody.

Another aspect of the invention is a pharmaceutical composition comprising a therapeutically effective amount of an affinity reagent capable of specific binding to Ephrin type-A receptor 7 or a fragment thereof.

In another aspect the invention provides use of an Ephrin type-A receptor 7 polypeptide, or one or more fragments or derivatives thereof, for the treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

The invention also provides use of an Ephrin type-A receptor 7 polypeptide, one or more fragments or derivatives thereof in the manufacture of a medicament for the treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

In one aspect there is provided a method of treatment comprising administering a therapeutically effective amount of an Ephrin type-A receptor 7 polypeptide, one or more fragments or derivatives thereof, or one or more fragments or derivatives thereof, for the treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

The invention further provides a method for the treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a subject, or of vaccinating a subject against bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, which comprises the step of administering to the subject an effective amount of an Ephrin type-A receptor 7 polypeptide and/or one or more antigenic or immunogenic fragments thereof, for example as a vaccine.

The mammalian subject may be a non-human mammal, but is generally human, such as a human adult, i.e. a human subject at least 21 (for example at least 35, at least 50, at least 60, at least 70, or at least 80) years old.

In one aspect there is provided a composition capable of eliciting an immune response in a subject, which composition comprises an Ephrin type-A receptor 7 polypeptide and/or one or more antigenic or immunogenic fragments thereof, and one or more suitable adjuvants (suitable adjuvants are discussed below).

The composition capable of eliciting an immune response may for example be provided as a vaccine comprising an Ephrin type-A receptor 7 polypeptide or derivatives thereof, and/or one or more antigenic or immunogenic fragments thereof.

For clarity of disclosure, and not by way of limitation, the invention will be described with respect to the analysis of bladder, breast, colorectal, gastric, head and neck, kidney, lung, osteoblast, pancreatic, prostate, skin, thyroid or uterine tissue. However, as one skilled in the art will appreciate, the assays and techniques described below can be applied to other types of patient samples, including body fluids (e.g. blood, urine or saliva), a tissue sample from a patient at risk of having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer (e.g. a biopsy such as a bladder, breast, colorectal, gastric, head and neck, kidney, lung, bone, pancreatic, prostate, skin, thyroid or uterine biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

Ephrin Type-A Receptor 7

In one aspect of the invention, one-dimensional electrophoresis, isotope-coded affinity tags (ICAT), isobaric tags for relative and absolute quantification (iTRAQ) or another appropriate method is used to analyze bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer tissue samples from a subject, preferably a living subject, in order to measure the expression of the protein of the invention for screening or diagnosis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, to determine the prognosis of a bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer patient, to monitor the effectiveness of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer therapy, or for drug development.

As used herein, the term "Protein of the invention", or "Ephrin type-A receptor 7", refers to the protein illustrated in FIG. 1 in its two different isoforms detected experimentally by 1D gel electrophoresis, ICAT and iTRAQ analysis of breast cancer, colorectal cancer, lung cancer, osteosarcoma or prostate cancer tissue samples (Ephrin type-A receptor 7a [SEQ ID No: 1] and Ephrin type-A receptor 7b [SEQ ID No: 2]). Protein derivatives of these sequences may also be useful for the same purposes as described herein.

This protein has been identified in membrane protein extracts or lysates of breast cancer, colorectal cancer, lung cancer, osteosarcoma or prostate cancer tissue samples from breast cancer, colorectal cancer, lung cancer, osteosarcoma or prostate cancer patients, through the methods and apparatus of the Preferred Technologies described in Examples 1-4 (1D gel electrophoresis, ICAT or iTRAQ and tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the following entry: Q15375, Ephrin type-A receptor 7 was identified.

According to SWISS-PROT, Ephrin type-A receptor 7 is widely expressed. It is a receptor for members of the ephrin-A family and it binds to ephrin-A1, -A2, -A3, -A4 and -A5.

Immunohistochemistry experiments (see Example 5) showed strong staining in colorectal cancer, lung cancer, bladder cancer, uterine cancer, head and neck cancer, skin cancer, kidney cancer, thyroid cancer and pancreatic cancer and metastatic breast, colorectal, gastric, lung and thyroid cancer.

The protein of the invention is useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full protein e.g. 90% or more e.g. 75% or 50% or 25% or 10% or more of the length of the full protein.

Alternatively, the protein/polypeptide employed or referred to herein may be limited to those specifically recited/described in the present specification or a moiety 80, 85, 90, 91, 92, 93, 94, 95, 96, 97, 98 or 99% identical or similar thereto.

Epitope containing fragments including antigenic or immunogenic fragments will be capable of eliciting a relevant immune response in a patient. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Derivatives of proteins also include chemically treated protein such as carboxymethylated, carboxyamidated, acetylated proteins, for example treated during purification.

Tables 1a-1c below illustrates the occurrences of Ephrin type-A receptor 7 as detected by iTRAQ and mass spectrometry of membrane protein extracts or lysates of breast, colorectal and lung tissue samples from breast cancer, colorectal cancer and lung cancer patients. The first column provides the samples batch number, the second column gives the iTRAQ experiment number and the last column provides the sequences observed by mass spectrometry and the corresponding SEQ ID Nos.

Tables 2a-2b below illustrates the occurrences of Ephrin type-A receptor 7 as detected by 1D gel electrophoresis and mass spectrometry of membrane protein extracts of colorectal and osteoblast tissue samples from colorectal cancer and osteosarcoma patients. The first column provides the molecular weight, the second column gives information on the subfractionation protocol used, if any (see Example 1 below), and the last column provides a list of the sequences observed by mass spectrometry and the corresponding SEQ ID Nos.

Table 3 below illustrates the different occurrences of OGTA278 as detected by ICAT and mass spectrometry of membrane protein extracts of prostate tissue samples from prostate cancer patients. The first column provides the sample number and the last column provides a list of the sequences observed by mass spectrometry and the corresponding SEQ ID Nos.

TABLE 1a

Breast cancer iTRAQ

| Sample batch no. | Experiment no. | Tryptics identified [SEQ ID No] |
|---|---|---|
| Samples 1 | Experiment 1 | ADQEGDEELYFHFK [4], CPTHSFSDK [7], WTAPEAIQYR [12] |

TABLE 1b

Colorectal cancer iTRAQ

| Sample batch no. | Experiment no. | Tryptics identified [SEQ ID No] |
|---|---|---|
| Samples 1 | Experiment 1 | ADQEGDEELYFHFK [4], VSDFGLSR [11], WTAPEAIQYR [12] |
| Samples 2 | Experiment 1 | CPTHSFSDK [7], VSDFGLSR [11], WTAPEAIQYR [12] |

TABLE 1c

Lung cancer iTRAQ

| Sample batch no. | Experiment no. | Tryptics identified [SEQ ID No] |
|---|---|---|
| Samples 1 | Experiment 1 | ADQEGDEELYFHFK [4] |
| Samples 2 | Experiment 1 | CPTHSFSDK [7], VSDFGLSR [11], WTAPEAIQYR [12] |

TABLE 2a

Colorectal cancer 1D GE

| MW (Da) | Subfractionation | Tryptics identified [SEQ ID No] |
|---|---|---|
| — | Heparin Binding | AFTAAGYGNYSPR [5], AIEEGYR [6], CPTHSFSDK [7], HDGQFTVIQLVGMLR [8], RHCGYSK [10], VSDFGLSR [11], WTAPEALQYR [12] |

TABLE 2b

Osteosarcoma 1D GE

| MW (Da) | Subfractionation | Tryptics identified [SEQ ID No] |
|---|---|---|
| 25763 | | ADQEGDEELYFHFK [4], MTIEDVMSLGITLVGHQK [9] |

TABLE 3

Prostate cancer ICAT

| Sample | Tryptics identified [SEQ ID No] |
|---|---|
| Sample 1 | CPTHSFSDK [7] |
| Sample 2 | CPTHSFSDK [7] |
| Sample 3 | CPTHSFSDK [7] |
| Sample 4 | CPTHSFSDK [7] |

For Ephrin type-A receptor 7, the detected level obtained upon analyzing tissue from subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer relative to the detected level obtained upon analyzing tissue from subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer will depend upon the particular analytical protocol and detection technique that is used. Accordingly, the present invention contemplates that each laboratory will establish a reference range in subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, according to the analytical protocol and detection technique in use, as is conventional in the diagnostic art. Preferably, at least one control positive tissue sample from a subject known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or at least one control negative tissue sample from a subject known to be free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer (and more preferably both positive and negative control samples) are included in each batch of test samples analysed.

Ephrin type-A receptor 7 can be used for detection, prognosis, diagnosis, or monitoring of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or for drug development. In one embodiment of the invention, tissue from a subject (e.g. a subject suspected of having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer) is analysed by 1D gel, ICAT or iTRAQ for detection of Ephrin type-A receptor 7. An increased abundance of Ephrin type-A receptor 7 in the tissue from the subject relative to tissue from a subject or subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer (e.g. a control sample) or a previously determined reference range indicates the presence of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

The sequences shown in Tables 1-3 may be employed in any relevant aspect of the invention.

In relation to fragments, epitope containing fragments, immunogenic fragments or antigenic fragments of Ephrin type-A receptor 7:

for breast cancer applications, in one aspect of the invention these comprise the sequences identified as tryptic sequences in the 3$^{rd}$ column of Table 1a;

for colorectal cancer applications, in one aspect of the invention these comprise the sequences identified as tryptic sequences in the 3$^{rd}$ column of Table 1b or Table 2a;

for lung cancer applications, in one aspect of the invention these comprise the sequences identified as tryptic sequences in the 3$^{rd}$ column of Table 1c;

for osteosarcoma applications, in one aspect of the invention these comprise the sequences identified as tryptic sequences in the 3$^{rd}$ column of Table 2b;

for prostate cancer applications, in one aspect of the invention these comprise the sequences identified as tryptic sequences in the 3$^{rd}$ column of Table 3.

Ephrin type-A receptor 7 may, in particular, be characterized as an isoform having a MW substantially as recited (e.g. +/−10%, particularly +/−5% of the value) in column 1 of Table 2b.

As used herein, Ephrin type-A receptor 7 is "isolated" when it is present in a preparation that is substantially free of contaminating proteins, i.e. a preparation in which less than 10% (for example less than 5%, such as less than 1%) of the total protein present is contaminating protein(s). A contaminating protein is a protein having a significantly different amino acid sequence from that of isolated Ephrin type-A receptor 7, as determined by mass spectral analysis. As used herein, a "significantly different" sequence is one that permits the contaminating protein to be resolved from Ephrin type-A receptor 7 by mass spectral analysis, performed according to the Reference Protocols described herein in Examples 1-4.

Thus in one aspect the invention provides a pharmaceutical composition for the treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer comprising a therapeutically effective amount of an Ephrin type-A receptor 7 polypeptide (particularly those defined above) or an immunogenic fragment thereof and an adjuvant.

Ephrin type-A receptor 7 can be assayed by any method known to those skilled in the art, including but not limited to, the Preferred Technologies described herein, kinase assays, enzyme assays, binding assays and other functional assays, immunoassays, and western blotting. In one embodiment, Ephrin type-A receptor 7 is separated on a 1-D gel by virtue of its MW and visualized by staining the gel. In one embodiment, Ephrin type-A receptor 7 is stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety. In another embodiment, Ephrin type-A receptor 7 is analysed using isobaric tags for relative and absolute quantification (iTRAQ). In another embodiment, Ephrin type-A receptor 7 is analysed using isotope-coded affinity tags (ICAT).

Alternatively, Ephrin type-A receptor 7 can be detected in an immunoassay. In one embodiment, an immunoassay is performed by contacting a sample from a subject to be tested with an anti-Ephrin type-A receptor 7 antibody (or other affinity reagent) under conditions such that binding (e.g. immunospecific binding) can occur if Ephrin type-A receptor 7 is present, and detecting or measuring the amount of any binding (e.g. immunospecific binding) by the agent. Ephrin type-A receptor 7 binding agents can be produced by the methods and techniques taught herein.

Ephrin type-A receptor 7 may be detected by virtue of the detection of a fragment thereof e.g. an epitope containing (e.g. an immunogenic or antigenic) fragment thereof. Fragments may have a length of at least 10, more typically at least 20 amino acids e.g. at least 50 or 100 amino acids e.g. at least 200 or 400 amino acids; e.g. at least 600 or 900 amino acids.

In one embodiment, binding of an affinity reagent (e.g. an antibody) in tissue sections can be used to detect aberrant Ephrin type-A receptor 7 localization or an aberrant level of Ephrin type-A receptor 7. In a specific embodiment, an antibody (or other affinity reagent) to Ephrin type-A receptor 7 can be used to assay a patient tissue (e.g. a bladder, breast, colorectal, gastric, head and neck, kidney, lung, osteoblast, pancreatic, prostate, skin, thyroid or uterine tissue) for the level of Ephrin type-A receptor 7 where an aberrant level of Ephrin type-A receptor 7 is indicative of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. As used herein, an "aberrant level" means a level that is increased compared with the level in a subject free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, Ephrin type-A receptor 7 can be detected in a fluid sample (e.g. blood, urine, or saliva) by means of a two-step sandwich assay. In the first step, a capture reagent (e.g. an anti-Ephrin type-A receptor 7 antibody or other affinity reagent) is used to capture Ephrin type-A receptor 7. The capture reagent can optionally be immobilized on a solid phase. In the second step, a directly or indirectly labeled detection reagent is used to detect the captured Ephrin type-A receptor 7. In one embodiment, the detection reagent is a lectin. Any lectin can be used for this purpose that preferentially binds to Ephrin type-A receptor 7 rather than to other isoforms that have the same core protein as Ephrin type-A receptor 7 or to other proteins that share the antigenic determinant recognized by the antibody. In a preferred embodiment, the chosen lectin binds Ephrin type-A receptor 7 with at least 2-fold greater affinity, more preferably at least 5-fold greater affinity, still more preferably at least 10-fold greater affinity, than to said other isoforms that have the same core protein as Ephrin type-A receptor 7 or to said other proteins that share the antigenic determinant recognized by the affinity reagent. Based on the present description, a lectin that is suitable for detecting Ephrin type-A receptor 7 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent), e.g. an antibody that specifically (e.g. immunospecifically) detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding Ephrin type-A receptor 7, a related gene, or related nucleic acid sequences or subsequences, including complementary sequences, can also be used in hybridization assays. A nucleotide encoding Ephrin type-A receptor 7, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding Ephrin type-A receptor 7, or for differential diagnosis of subjects with signs or symptoms suggestive of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. In particular, such a hybridization assay can be carried out by a method comprising contacting a subject's sample containing nucleic acid with a nucleic acid probe capable of hybridizing to a DNA or RNA that encodes Ephrin type-A receptor 7, under conditions such that hybridization can occur, and detecting or measuring any resulting hybridization.

Hence nucleic acid encoding Ephrin type-A receptor 7 (e.g. DNA or more suitably RNA) may be detected, for example, using a hybridizing agent capable of hybridizing to nucleic acid encoding Ephrin type-A receptor 7.

One such exemplary method comprises:
(a) contacting one or more oligonucleotide probes comprising 10 or more consecutive nucleotides complementary to a nucleotide sequence encoding Ephrin type-A receptor 7, with an RNA obtained from a biological sample from the subject or with cDNA copied from the RNA, wherein said contacting occurs under conditions that permit hybridization of the probe to the nucleotide sequence if present;
(b) detecting hybridization, if any, between the probe and the nucleotide sequence; and
(c) comparing the hybridization, if any, detected in step (b) with the hybridization detected in a control sample, or with a previously determined reference range.

The invention also provides diagnostic kits, comprising an anti-Ephrin type-A receptor 7 antibody (or other affinity reagent). In addition, such a kit may optionally comprise one or more of the following: (1) instructions for using the anti-Ephrin type-A receptor 7 affinity reagent for diagnosis, prognosis, therapeutic monitoring or any combination of these applications; (2) a labeled binding partner to the affinity reagent; (3) a solid phase (such as a reagent strip) upon which the anti-Ephrin type-A receptor 7 affinity reagent is immobilized; and (4) a label or insert indicating regulatory approval for diagnostic, prognostic or therapeutic use or any combination thereof. If no labeled binding partner to the affinity reagent is provided, the anti-Ephrin type-A receptor 7 affinity reagent itself can be labeled with a detectable marker, e.g. a chemiluminescent, enzymatic, fluorescent, or radioactive moiety.

The invention also provides a kit comprising a nucleic acid probe capable of hybridizing to nucleic acid, suitably RNA, encoding Ephrin type-A receptor 7. In a specific embodiment, a kit comprises in one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding Ephrin type-A receptor 7, such as by polymerase chain reaction (see, e.g. Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of Ephrin type-A receptor 7 or a nucleic acid encoding Ephrin type-A receptor 7, e.g. for use as a standard or control.

Use in Clinical Studies

The diagnostic methods and compositions of the present invention can assist in monitoring a clinical study, e.g. to evaluate drugs for therapy of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. In one embodiment, candidate molecules are tested for their ability to restore Ephrin type-A receptor 7 levels in a subject having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer to levels found in subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer or, in a treated subject, to preserve Ephrin type-A receptor 7 levels at or near non-bladder cancer, non-breast cancer, non-colorectal cancer, non-gastric cancer, non-head and neck cancer, non-kidney cancer, non-lung cancer, non-osteosarcoma, non-pancreatic cancer, non-prostate cancer, non-skin cancer, non-thyroid cancer or non-uterine cancer values.

In another embodiment, the methods and compositions of the present invention are used to screen candidates for a clinical study to identify individuals having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer; such individuals can then be excluded from the study or can be placed in a separate cohort for treatment or analysis.

Production of Protein of the Invention and Corresponding Nucleic Acid

In one aspect the invention provides a method of treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, comprising administering to a subject in need of such treatment or prevention a therapeutically effective amount of nucleic acid encoding Ephrin type-A receptor 7 or one or more fragments or derivatives thereof, for example in the form of a vaccine.

In another aspect there is provided a method of treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer comprising administering to a subject in need of such treatment or prevention a therapeutically effective amount of nucleic acid that inhibits the function or expression of Ephrin type-A receptor 7.

The methods (and/or other DNA aspects disclosed herein) of the invention may, for example include wherein the nucleic acid is an Ephrin type-A receptor 7 anti-sense nucleic acid or ribozyme.

Thus the invention includes the use of nucleic acid encoding Ephrin type-A receptor 7 or one or more fragments or derivatives thereof, in the manufacture of a medicament for treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

There is also provided the use of nucleic acid that inhibits the function or expression of Ephrin type-A receptor 7 in the manufacture of a medicament for treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

A DNA employed in the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined.

Furthermore, databases of known genes are searched for homology using the thus obtained terminal nucleotide sequences as queries.

In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from bladder, breast, colorectal, gastric, head and neck, kidney, lung, osteoblast, pancreatic, prostate, skin, thyroid or uterine tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of Ephrin type-A receptor 7 or DNA encoding the above polypeptide consisting of an amino acid sequence derived from the amino acid sequence of Ephrin type-A receptor 7 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of Ephrin type-A receptor 7 and DNA hybridizing under stringent conditions to the DNA and encoding a polypeptide (protein) having biological activity (function) equivalent to the function of the polypeptide consisting of the amino acid sequence of Ephrin type-A receptor 7. Under such conditions, an example of such DNA capable of hybridizing to DNA comprising the nucleotide sequence that encodes the amino acid sequence of Ephrin type-A receptor 7 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

In the methods/uses of the invention, Ephrin type-A receptor 7 may for example be provided in isolated form, such as where the Ephrin type-A receptor 7 polypeptide has been purified at least to some extent. Ephrin type-A receptor 7 polypeptide may be provided in substantially pure form, that is to say free, to a substantial extent, from other proteins. Ephrin type-A receptor 7 polypeptide can also be produced using recombinant methods, synthetically produced or produced by a combination of these methods. Ephrin type-A receptor 7 can be easily prepared by any method known by persons skilled in the art, which involves producing an expression vector containing appropriate DNA of the present invention or a gene containing a DNA of the present invention, culturing a transformant transformed using the expression vector, generating and accumulating a relevant polypeptide of the present invention or a recombinant protein containing the polypeptide, and then collecting the resultant.

Recombinant Ephrin type-A receptor 7 polypeptide may be prepared by processes well known in the art from genetically engineered host cells comprising expression systems. Accordingly, the present invention also relates to expression systems which comprise an Ephrin type-A receptor 7 polypeptide or nucleic acid, to host cells which are genetically engineered with such expression systems and to the production of Ephrin type-A receptor 7 polypeptide by recombinant techniques. For recombinant Ephrin type-A receptor 7 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127,3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda]

phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRα promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the Ephrin type-A receptor 7 polypeptide to allow secretion of the translated protein into the lumen of the endoplasmic reticulum, the periplasmic space or the extracellular environment. These signals may be endogenous to the Ephrin type-A receptor 7 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an Ephrin type-A receptor 7 polypeptide is to be expressed for use in cell-based screening assays, it is preferred that the polypeptide be produced at the cell surface. In this event, the cells may be harvested prior to use in the screening assay. If the Ephrin type-A receptor 7 polypeptide is secreted into the medium, the medium can be recovered in order to isolate said polypeptide. If produced intracellularly, the cells must first be lysed before the Ephrin type-A receptor 7 polypeptide is recovered.

Ephrin type-A receptor 7 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an Ephrin type-A receptor 7 polypeptide can be used to deplete a sample comprising an Ephrin type-A receptor 7 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the Ephrin type-A receptor 7 polypeptide when the polypeptide has been denatured during isolation and or purification. In the context of the present invention, Ephrin type-A receptor 7 polypeptide can be obtained from a biological sample from any source, such as and without limitation, a blood sample or tissue sample, e.g. a bladder, breast, colorectal, gastric, head and neck, kidney, lung, osteoblast, pancreatic, prostate, skin, thyroid or uterine tissue sample.

Ephrin type-A receptor 7 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

Ephrin type-A receptor 7 may, for example, be fused with a heterologous fusion partner such as the surface protein, known as protein D from Haemophilus Influenza B, a non-structural protein from influenzae virus such as NS1, the S antigen from Hepatitis B or a protein known as LYTA such as the C terminal thereof.

An additional sequence that may provide stability during recombinant production may also be used. Such sequences may be optionally removed as required by incorporating a cleavable sequence as an additional sequence or part thereof. Thus, an Ephrin type-A receptor 7 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to Ephrin Type-A Receptor 7

According to those in the art, there are three main types of immunoaffinity reagent—monoclonal antibodies, phage display antibodies and smaller antibody-derived molecules such as Affibodies, Domain Antibodies (dAbs), Nanobodies, UniBodies, DARPins, Anticalins, Duocalins, Avimers or Versabodies. In general in applications according to the present invention where the use of antibodies is stated, other affinity reagents (e.g. Affibodies, Domain Antibodies, Nanobodies, UniBodies, DARPins, Anticalins, Duocalins, Avimers or Versabodies) may be employed. Such substances may be said to be capable of immunospecific binding to Ephrin type-A receptor 7. Where appropriate the term "affinity agent" shall be construed to embrace immunoaffinity reagents and other substances capable of specific binding to Ephrin type-A receptor 7 including but not limited to ligands, lectins, streptavidins, antibody mimetics and synthetic binding agents.

Production of Antibodies to Ephrin Type-A Receptor 7

According to the invention Ephrin type-A receptor 7, an Ephrin type-A receptor 7 analog, an Ephrin type-A receptor 7-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175: 267-273; Yarmush (1992) *J. Biochem. Biophys. Methods* 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VII domain; and (vi) an isolated complementarity determining region (CDR). Single chain antibodies are also included by reference in the term "antibody". Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g. IgG, IgE, IgM, IgD and IgA such as IgG) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is typically about 5-fold greater when compared to its affinity for a non-target molecule. Suitably there is no significant cross-reaction or cross-binding with undesired substances, especially naturally occurring proteins or tissues of a healthy person or animal. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In some embodiments, specific binding between an antibody or other binding agent and an antigen means a binding affinity of at least $10^6$ M$^{-1}$. Antibodies may, for example, bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$.

Affinity is calculated as $K_d=k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: r/c=K(n−r):

where r=moles of bound ligand/mole of receptor at equilibrium;

c=free ligand concentration at equilibrium;

K=equilibrium association constant; and n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g. U.S. Pat. No. 6,316,409). The affinity of a targeting agent for its target molecule is for example at least about $1\times10^{-6}$ moles/liter, such as at least about $1\times10^{-7}$ moles/liter, such as at least about $1\times10^{-8}$ moles/liter, especially at least about $1\times10^{-9}$ moles/liter, and particularly at least about 1×10−10 moles/liter. Antibody affinity measurement by Scatchard analysis is well known in the art. See, e.g. van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding Ephrin type-A receptor 7 are publicly available. In another embodiment, methods known to those skilled in the art are used to produce antibodies that recognize Ephrin type-A receptor 7, an Ephrin type-A receptor 7 analog, an Ephrin type-A receptor 7-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of Ephrin type-A receptor 7 are produced. In a specific embodiment, hydrophilic fragments of Ephrin type-A receptor 7 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of Ephrin type-A receptor 7, one may assay generated hybridomas for a product which binds to an Ephrin type-A receptor 7 fragment containing such domain. For selection of an antibody that specifically binds a first Ephrin type-A receptor 7 homolog but which does not specifically bind to (or binds less avidly to) a second Ephrin type-A receptor 7 homolog, one can select on the basis of positive binding to the first Ephrin type-A receptor 7 homolog and a lack of binding to (or reduced binding to) the second Ephrin type-A receptor 7 homolog. Similarly, for selection of an antibody that specifically binds Ephrin type-A receptor 7 but which does not specifically bind to (or binds less avidly to) a different isoform of the same protein (such as a different glycoform having the same core peptide as Ephrin type-A receptor 7), one can select on the basis of positive binding to Ephrin type-A receptor 7 and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to Ephrin type-A receptor 7 than to a different isoform or isoforms (e.g. glycoforms) of Ephrin type-A receptor 7.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to Ephrin type-A receptor 7, a fragment of Ephrin type-A receptor 7, an Ephrin type-A receptor 7-related polypeptide, or a fragment of an Ephrin type-A receptor 7-related polypeptide. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. If Ephrin type-A receptor 7 is purified by gel electrophoresis, Ephrin type-A receptor 7 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward Ephrin type-A receptor 7, a fragment of Ephrin type-A receptor 7, an Ephrin type-A receptor 7-related polypeptide, or a fragment of an Ephrin type-A receptor 7-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb. (See, e.g. Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239: 1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of Ephrin type-A receptor 7. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. No. 5,625,126; U.S. Pat. No. 5,633,425; U.S. Pat. No. 5,569,825; U.S. Pat. No. 5,661,016; and U.S.

Pat. No. 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogs of the anti-Ephrin type-A receptor 7 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAB) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of Ephrin type-A receptor 7, e.g. for imaging this protein, measuring levels thereof in appropriate physiological samples, in diagnostic methods, etc.

Production of Affibodies to Ephrin Type-A Receptor 7

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of Affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to Ephrin Type-A Receptor 7

References to antibodies herein embrace references to Domain Antibodies. Domain Antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to Ephrin Type-A Receptor 7

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells.

Production of UniBodies to Ephrin Type-A Receptor 7

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Production of DARPins to Ephrin Type-A Receptor 7

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO 02/20565, both of which are hereby incorporated by reference in their entirety.

Production of Anticalins to Ephrin Type-A Receptor 7

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein; they can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Production of Avimers to Ephrin Type-A Receptor 7

Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Production of Versabodies to Ephrin Type-A Receptor 7

Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, for example, by generating monoclonal antibodies. Alternatively, a clone encoding at least the Fab portion of the antibody may be obtained by screening Fab expression libraries (e.g. as described in Huse et al., 1989, Science 246:1275-1281) for clones of Fab fragments that bind the specific antigen or by screening antibody libraries (See, e.g. Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253: 6551), PCT based methods, etc.

In addition, techniques developed for the production of "chimeric antibodies" (Morrison et al., 1984, Proc. Natl. Acad. Sci. 81:851-855; Neuberger et al., 1984, *Nature* 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or a specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitrilo-acetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. Ephrin type-A receptor 7) as immunogen. Humanisation typically involves grafting CDRs identified thereby into human framework regions. Normally some subsequent retromutation to optimize the conformation of chains is required. Such processes are known to persons skilled in the art.
Expression of Affibodies The construction of Affibodies has been described elsewhere (Ronnmark J, Gronlund H, Uhlen, M., Nygren P. A, Human immunoglobulin A (IgA)-specific ligands from combinatorial engineering of protein A, 2002, Eur. J. Biochem. 269, 2647-2655.), including the construction of Affibody phage display libraries (Nord, K., Nilsson, J., Nilsson, B., Uhlen, M. & Nygren, P. A, A combinatorial library of an a-helical bacterial receptor domain, 1995, Protein Eng. 8, 601-608. Nord, K., Gunneriusson, E., Ringdahl, J., Stahl, S., Uhlen, M. & Nygren, P. A, Binding proteins selected from combinatorial libraries of an a-helical bacterial receptor domain, 1997, Nat. Biotechnol. 15, 772-777.)

The biosensor analyses to investigate the optimal Affibody variants using biosensor binding studies has also been described elsewhere (Ronnmark J, Gronlund H, Uhlen, M., Nygren P. A, Human immunoglobulin A (IgA)-specific ligands from combinatorial engineering of protein A, 2002, Eur. J. Biochem. 269, 2647-2655.).
Affinity Reagent Modifications In a preferred embodiment, anti-Ephrin type-A receptor 7 affinity reagents such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$. $^{68}Ga$ may also be employed.

Anti-Ephrin type-A receptor 7 antibodies or fragments thereof as well as other affinity reagents can be conjugated to a therapeutic agent or drug moiety to modify a given biological response. An exemplary therapeutic agent to which the affinity reagent may be conjugated is a cytotoxic moiety. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g. Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery ($2^{nd}$ Ed.), Robinson et al. (eds.), pp.

623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanised antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and Xenomouse (Abgenix Inc., CA). A humanised antibody is one in which the constant region of a non-human antibody molecule of appropriate antigen specificity, is replaced by the constant region of a human antibody, preferably of the IgG subtype, with appropriate effector functions (Morrison et al., 1984, Proc. Natl. Acad. Sci. 81:851-855; Neuberger et al., 1984, *Nature* 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu3+) from Eu3+ labelled, living cells in the presence of an antigen-specific antibody and peripheral blood mononuclear cells extracted from an immunocompetent, living human subject. The ADCC process is described in detail in Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p 2153-68 and Weng, W.-K. et al., Journal of Clinical Oncology, 2003, 21:p 3940-3947. Suitable methods for the detection and quantification of ADCC can be found in Blomberg et al., Journal of Immunological Methods. 1986, 86:p 225-9; Blomberg et al., Journal of Immunological Methods. 1986, 21; 92:p 117-23 and Patel & Boyd, Journal of Immunological Methods. 1995, 184:p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perforin and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha1,6-linked fucose moieties in the complex oligosaccharide chains that are normally added to the Fc of antibodies during natural or recombinant synthesis in mammalian cells. In a preferred embodiment, non-fucosylated anti-Ephrin type-A receptor 7 affinity reagents such as antibodies or fragments thereof are produced for the purpose of enhancing their ability to induce the ADCC response.

Techniques for reducing or ablating alpha1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. Preferably, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8−/− CHO/DG44 cell lines. Techniques for synthesizing partially fucosylated, or non-fucosylated antibodies and affinity reagents are described in Shinkawa et al., J. Biol. Chem. 278:3466-34735 (2003); Yamane-Ohnuki et al., Biotechnology and Bioengineering 87: 614-22 (2004) and in WO00/61739 A1, WO02/31140 A1 and WO03/085107 A1. In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO9954342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103:p 4005-4010; WO03074679 and WO2007039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

Diagnosis of Bladder Cancer, Breast Cancer, Colorectal Cancer, Gastric Cancer, Head and Neck Cancer, Kidney Cancer, Lung Cancer, Osteosarcoma, Pancreatic Cancer, Prostate Cancer, Skin Cancer, Thyroid Cancer or Uterine Cancer, Including Metastatic Cancer In accordance with the present invention, test samples of bladder, breast, colorectal, gastric, head and neck, kidney, lung, osteoblast, pancreatic, prostate, skin, thyroid or uterine tissue, serum, plasma or urine obtained from a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer can be used for diagnosis or monitoring. In one embodiment, a change in the abundance of Ephrin type-A receptor 7 in a test sample relative to a control sample (from a subject or subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer) or a previously determined reference range indicates the presence of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. In another embodiment, the relative abundance of Ephrin type-A receptor 7 in a test sample compared to a control sample or a previously determined reference range indicates a subtype of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer (e.g. squamous cell bladder cancer, inflammatory breast cancer, familial or sporadic colorectal cancer, gastrointestinal stromal tumors (GIST); nasopharyngeal cancer; transitional cell kidney carcinoma, squamous cell lung carcinoma, parosteal or periosteal osteosarcoma, endocrine tumours of the pancreas or anaplastic thyroid carcinoma). In yet another embodiment, the relative abundance of Ephrin type-A receptor 7 in a test sample relative to a control sample or a previously determined reference range indicates the degree or severity of bladder cancer, breast cancer, colorectal cancer, gastric cancer, head and neck cancer, kidney cancer, lung cancer, osteosarcoma, pancreatic cancer, prostate cancer, skin cancer or uterine cancer (e.g. the likelihood for metastasis). In any of the aforesaid methods, detection of Ephrin type-A receptor 7 may optionally be combined with detection of one or more of additional biomarkers for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Any suitable method in the art can be employed to measure the level of Ephrin type-A receptor 7, including but not limited to the Preferred Technologies described herein, kinase assays, immunoassays to detect and/or visualize the Ephrin type-A receptor 7 (e.g. Western blot, immunoprecipitation followed by sodium dodecyl sulfate polyacrylamide gel electrophoresis, immunocytochemistry, etc.). In a further embodiment, a change in the abundance of mRNA encoding Ephrin type-A receptor 7 in a test sample relative to a control sample or a previously determined reference range indicates the presence of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Any suitable hybridization assay can be used to detect Ephrin type-A receptor 7 expression by detecting and/or visualizing mRNA encoding the Ephrin type-A receptor 7 (e.g. Northern assays, dot blots, in situ hybridization, etc.).

In another embodiment of the invention, labeled antibodies (or other affinity reagents), derivatives and analogs thereof, which specifically bind to Ephrin type-A receptor 7 can be used for diagnostic purposes to detect, diagnose, or monitor bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Preferably, bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is detected in an animal, more preferably in a mammal and most preferably in a human.

Screening Assays

The invention provides methods for identifying agents (e.g. candidate compounds or test compounds) that bind to Ephrin type-A receptor 7 or have a stimulatory or inhibitory effect on the expression or activity of Ephrin type-A receptor 7. The invention also provides methods of identifying agents, candidate compounds or test compounds that bind to an Ephrin type-A receptor 7-related polypeptide or an Ephrin type-A receptor 7 fusion protein or have a stimulatory or inhibitory effect on the expression or activity of an Ephrin type-A receptor 7-related polypeptide or an Ephrin type-A receptor 7 fusion protein. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e. bind to) Ephrin type-A receptor 7, an Ephrin type-A receptor 7 fragment (e.g. a functionally active fragment), an Ephrin type-A receptor 7-related polypeptide, a fragment of an Ephrin type-A receptor 7-related polypeptide, or an Ephrin type-A receptor 7 fusion protein are identified in a cell-based assay system. In accordance with this embodiment, cells expressing Ephrin type-A receptor 7, a fragment of an Ephrin type-A receptor 7, an Ephrin type-A receptor 7-related polypeptide, a fragment of the Ephrin type-A receptor 7-related polypeptide, or an Ephrin type-A receptor 7 fusion protein are contacted with a candidate compound or a control compound and the ability of the candidate compound to interact with the Ephrin type-A receptor 7 is determined. If desired, this assay may be used to screen a plurality (e.g. a library) of candidate compounds. The cell, for example, can be of prokaryotic origin (e.g. E. coli) or eukaryotic origin (e.g. yeast or mammalian). Further, the cells can express Ephrin type-A receptor 7, a fragment of Ephrin type-A receptor 7, an Ephrin type-A receptor 7-related polypeptide, a fragment of the Ephrin type-A receptor 7-related polypeptide, or an Ephrin type-A receptor 7 fusion protein endogenously or be genetically engineered to express Ephrin type-A receptor 7, a fragment of Ephrin type-A receptor 7, an Ephrin type-A receptor 7-related polypeptide, a fragment of the Ephrin type-A receptor 7-related polypeptide, or an Ephrin type-A receptor 7 fusion protein. In certain instances, Ephrin type-A receptor 7, a fragment of Ephrin type-A receptor 7, an Ephrin type-A receptor 7-related polypeptide, a fragment of the Ephrin type-A receptor 7-related polypeptide, or an Ephrin type-A receptor 7 fusion protein or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between Ephrin type-A receptor 7 and a candidate compound. The ability of the candidate compound to interact directly or indirectly with Ephrin type-A receptor 7, a fragment of an Ephrin type-A receptor 7, an Ephrin type-A receptor 7-related polypeptide, a fragment of an Ephrin type-A receptor 7-related polypeptide, or an Ephrin type-A receptor 7 fusion protein can be determined by methods known to those of skill in the art. For example, the interaction between a candidate compound and Ephrin type-A receptor 7, an Ephrin type-A receptor 7-related polypeptide, a fragment of an Ephrin type-A receptor 7-related polypeptide, or an Ephrin type-A receptor 7 fusion protein can be determined by flow cytometry, a scintillation assay, immunoprecipitation or western blot analysis.

In another embodiment, agents that interact with (i.e. bind to) Ephrin type-A receptor 7, an Ephrin type-A receptor 7 fragment (e.g. a functionally active fragment), an Ephrin type-A receptor 7-related polypeptide, a fragment of an Ephrin type-A receptor 7-related polypeptide, or an Ephrin type-A receptor 7 fusion protein are identified in a cell-free assay system. In accordance with this embodiment, native or recombinant Ephrin type-A receptor 7 or a fragment thereof, or a native or recombinant Ephrin type-A receptor 7-related polypeptide or fragment thereof, or an Ephrin type-A receptor 7-fusion protein or fragment thereof, is contacted with a candidate compound or a control compound and the ability of the candidate compound to interact with Ephrin type-A receptor 7 or Ephrin type-A receptor 7-related polypeptide, or Ephrin type-A receptor 7 fusion protein is determined. If desired, this assay may be used to screen a plurality (e.g. a library) of candidate compounds. Preferably, Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7-fusion protein is first immobilized, by, for example, contacting Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein with an immobilized antibody (or other affinity reagent) which specifically recognizes and binds it, or by contacting a purified preparation of Ephrin type-A receptor 7, an Ephrin type-A receptor 7 fragment, an Ephrin type-A receptor 7-related polypeptide, fragment of an Ephrin type-A receptor 7-related polypeptide, or an Ephrin type-A receptor 7 fusion protein with a surface designed to bind proteins. Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein may be partially or completely purified (e.g. partially or completely free of other polypeptides) or part of a cell lysate. Further, Ephrin type-A receptor 7, an Ephrin type-A receptor 7 fragment, an Ephrin type-A receptor 7-related polypeptide, or a fragment of an Ephrin type-A receptor 7-related polypeptide may be a fusion protein comprising Ephrin type-A receptor 7 or a biologically active portion thereof, or Ephrin type-A receptor 7-related polypeptide and a domain such as glutathionine-S-transferase. Alternatively, Ephrin type-A receptor 7, an Ephrin type-A receptor 7 fragment, an Ephrin type-A receptor 7-related polypeptide, a fragment of an Ephrin type-A receptor 7-related polypeptide or an Ephrin type-A receptor 7 fusion protein can be biotinylated using techniques well known to those of skill in the art (e.g. biotinylation kit, Pierce Chemicals; Rockford, Ill.). The ability of the candidate compound to interact with Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of Ephrin type-A receptor 7 or is responsible for the post-translational modification of Ephrin type-A receptor 7. In a primary screen, a plurality (e.g. a library) of compounds are contacted with cells that naturally or recombinantly express: (i) Ephrin type-A receptor 7, an isoform of Ephrin type-A receptor 7, an Ephrin type-A receptor 7 homolog, an Ephrin type-A receptor 7-related polypeptide, an Ephrin type-A receptor 7 fusion protein, or a biologically active fragment of any of the foregoing; and (ii) a protein that is responsible for processing of Ephrin type-A receptor 7, an Ephrin type-A receptor 7 isoform, an Ephrin type-A receptor 7 homolog, an Ephrin type-A receptor 7-related polypeptide, an Ephrin type-A receptor 7 fusion protein, or a fragment in order to identify compounds that modulate the production, degradation, or post-translational modification of Ephrin type-A receptor 7, an Ephrin type-A receptor 7 isoform, an Ephrin type-A receptor 7 homolog, an Ephrin type-A receptor 7-related polypeptide, an Ephrin type-A receptor 7 fusion protein or fragment. If desired, compounds identified in the primary screen can then be assayed in a secondary screen against cells naturally or recombinantly expressing Ephrin type-A receptor 7. The ability of the candidate compound to modulate the production, degradation or post-translational modification of Ephrin type-A receptor 7, isoform, homolog, Ephrin type-A receptor 7-related polypeptide, or Ephrin type-A receptor 7 fusion protein can be determined by methods known to those of skill in the art, including without limitation, flow cytometry, a scintillation assay, immunoprecipitation and western blot analysis.

In another embodiment, agents that competitively interact with (i.e. bind to) Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein are identified in a competitive binding assay. In accordance with this embodiment, cells expressing Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein are contacted with a candidate compound and a compound known to interact with Ephrin type-A receptor 7, an Ephrin type-A receptor 7 fragment, an Ephrin type-A receptor 7-related polypeptide, a fragment of an Ephrin type-A receptor 7-related polypeptide or an Ephrin type-A receptor 7 fusion protein; the ability of the candidate compound to preferentially interact with Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein is then determined. Alternatively, agents that preferentially interact with (i.e. bind to) Ephrin type-A receptor 7, an Ephrin type-A receptor 7 fragment, an Ephrin type-A receptor 7-related polypeptide or fragment of an Ephrin type-A receptor 7-related polypeptide are identified in a cell-free assay system by contacting Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein with a candidate compound and a compound known to interact with Ephrin type-A receptor 7, an Ephrin type-A receptor 7-related polypeptide or an Ephrin type-A receptor 7 fusion protein. As stated above, the ability of the candidate compound to interact with Ephrin type-A receptor 7, an Ephrin type-A receptor 7 fragment, an Ephrin type-A receptor 7-related polypeptide, a fragment of an Ephrin type-A receptor 7-related polypeptide, or an Ephrin type-A receptor 7 fusion protein can be determined by methods known to those of skill in the art. These assays, whether cell-based or cell-free, can be used to screen a plurality (e.g. a library) of candidate compounds.

In another embodiment, agents that modulate (i.e. upregulate or downregulate) the expression or activity of Ephrin type-A receptor 7 or an Ephrin type-A receptor 7-related polypeptide are identified by contacting cells (e.g. cells of prokaryotic origin or eukaryotic origin) expressing Ephrin type-A receptor 7 or an Ephrin type-A receptor 7-related polypeptide with a candidate compound or a control compound (e.g. phosphate buffered saline (PBS)) and determining the expression of Ephrin type-A receptor 7, Ephrin type-A receptor 7-related polypeptide, or Ephrin type-A receptor 7 fusion protein, mRNA encoding Ephrin type-A receptor 7, or mRNA encoding the Ephrin type-A receptor 7-related polypeptide. The level of expression of Ephrin type-A receptor 7, Ephrin type-A receptor 7-related polypeptide, mRNA encoding Ephrin type-A receptor 7, or mRNA encoding the Ephrin type-A receptor 7-related polypeptide in the presence of the candidate compound is compared to the level of expression of Ephrin type-A receptor 7, Ephrin type-A receptor 7-related polypeptide, mRNA encoding Ephrin type-A receptor 7, or mRNA encoding the Ephrin type-A receptor 7-related polypeptide in the absence of the candidate compound (e.g. in the presence of a control compound). The candidate compound can then be identified as a modulator of the expression of Ephrin type-A receptor 7, or the Ephrin type-A receptor 7-related polypeptide based on this comparison. For example, when expression of Ephrin type-A receptor 7 or mRNA is significantly greater in the presence of the candidate compound than in its absence, the candidate compound is identified as a stimulator of expression of Ephrin type-A receptor 7 or mRNA. Alternatively, when expression of Ephrin type-A receptor 7 or mRNA is significantly less in the presence of the candidate compound than in its absence, the candidate compound is identified as an inhibitor of the expression of Ephrin type-A receptor 7 or mRNA. The level of expression of Ephrin type-A receptor 7 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of Ephrin type-A receptor 7 or an Ephrin type-A receptor 7-related polypeptide are identified by contacting a preparation containing Ephrin type-A receptor 7 or Ephrin type-A receptor 7-related polypeptide or cells (e.g. prokaryotic or eukaryotic cells) expressing Ephrin type-A receptor 7 or Ephrin type-A receptor 7-related polypeptide with a test compound or a control compound and determining the ability of the test compound to modulate (e.g. stimulate or inhibit) the activity of Ephrin type-A receptor 7 or Ephrin type-A receptor 7-related polypeptide. The activity of Ephrin type-A receptor 7 or an Ephrin type-A receptor 7-related polypeptide can be assessed by detecting induction of a cellular signal transduction pathway of Ephrin type-A receptor 7 or Ephrin type-A receptor 7-related polypeptide (e.g. intracellular $Ca^{2+}$, diacylglycerol, IP3, etc.), detecting catalytic or enzymatic activity of the target on a suitable substrate, detecting the induction of a reporter gene (e.g. a regulatory element that is responsive to Ephrin type-A receptor 7 or an Ephrin type-A receptor 7-related polypeptide and is operably linked to a nucleic acid encoding a detectable marker, e.g. luciferase), or detecting a cellular response, for example, cellular differentiation, or cell proliferation. Based on the present description, techniques known to those of skill in the art can be used for measuring these activities (see, e.g. U.S. Pat. No. 5,401,639, which is incorporated herein by reference). The candidate compound can then be identified as a modulator of the activity of Ephrin type-A receptor 7 or an Ephrin type-A receptor 7-related polypeptide by comparing the effects of the candidate compound to the control compound. Suitable control compounds include phosphate buffered saline (PBS) and normal saline (NS).

In another embodiment, agents that modulate (i.e. upregulate or downregulate) the expression, activity or both the expression and activity of Ephrin type-A receptor 7 or an Ephrin type-A receptor 7-related polypeptide are identified in an animal model. Examples of suitable animals include, but are not limited to, mice, rats, rabbits, monkeys, guinea pigs, dogs and cats. Preferably, the animal used represent a model of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer (e.g. xenografts of bladder cancer cell lines such as UCRU-BL-12, UCRU-BL-13 and UCRU-BL-14, Russell et al. Cancer Res. 1986 April; 46(4 Pt 2):2035-40; xenografts of breast cancer cell lines such as MCF-7 (Ozzello L, Sordat M., Eur J Cancer. 1980; 16:553-559) and MCFlOAT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of head and neck cancer cell lines such as FaDu and HNX-OE; xenografts of renal cell cancer cell lines such as LABAZ1 in immune compromised mice, Zisman et al, Cancer Research 63, 4952-4959, Aug. 15, 2003;

xenografts of non small cell lung cancer cell lines such as A549 and H460 and xenografts of small cell lung cancer cell lines such as NCI-H345; xenografts of human osteosarcoma cell lines such as HuO9 in nude mice, Kimura et al., Clin Exp Metastasis 2002; 19(6):477-85; xenografts of pancreatic cancer cell lines such as MIA PaCa-2 in nude mice, Marincola et al., J Surg Res 1989 December; 47(6):520-9; xenografts of prostate cancer cell lines such as CWR-22 in nude mice, Pretlow et al, J Natl Cancer Inst. 1993 Mar. 3; 85(5):394-8; xenografts of skin cancer cell lines such as MV3 in nude mice, van Muijen et al, Int J Cancer 1991 Apr. 22; 48(1):85-91; xenografts of thyroid cancer cell lines such as ARO, Viaggi et al., Thyroid 2003 June; 13(6):529-36; and xenografts of uterine cancer cell lines such as HEC-1A and RL-95-2, Li et al., J Cancer Res Clin Oncol. 2007 May; 133(5):315-20). These can be utilized to test compounds that modulate Ephrin type-A receptor 7 levels, since the pathology exhibited in these models is similar to that of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer. In accordance with this embodiment, the test compound or a control compound is administered (e.g. orally, rectally or parenterally such as intraperitoneally or intravenously) to a suitable animal and the effect on the expression, activity or both expression and activity of Ephrin type-A receptor 7 or Ephrin type-A receptor 7-related polypeptide is determined. Changes in the expression of Ephrin type-A receptor 7 or an Ephrin type-A receptor 7-related polypeptide can be assessed by the methods outlined above.

In yet another embodiment, Ephrin type-A receptor 7 or an Ephrin type-A receptor 7-related polypeptide is used as a "bait protein" in a two-hybrid assay or three hybrid assay to identify other proteins that bind to or interact with Ephrin type-A receptor 7 or an Ephrin type-A receptor 7-related polypeptide (see, e.g. U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by Ephrin type-A receptor 7 as, for example, upstream or downstream elements of a signaling pathway involving Ephrin type-A receptor 7.

This invention further provides novel agents identified by the above-described screening assays and uses thereof for treatments as described herein. In addition, the invention also provides the use of an agent which interacts with, or modulates the activity of, Ephrin type-A receptor 7 in the manufacture of a medicament for the treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Therapeutic Use of Ephrin Type-A Receptor 7

The invention provides for treatment or prevention of various diseases and disorders by administration of a therapeutic compound. Such compounds include but are not limited to: Ephrin type-A receptor 7, Ephrin type-A receptor 7 analogs, Ephrin type-A receptor 7-related polypeptides and derivatives (including fragments) thereof; antibodies (or other affinity reagents) to the foregoing; nucleic acids encoding Ephrin type-A receptor 7, Ephrin type-A receptor 7 analogs, Ephrin type-A receptor 7-related polypeptides and fragments thereof; antisense nucleic acids to a gene encoding Ephrin type-A receptor 7 or an Ephrin type-A receptor 7-related polypeptide; and modulator (e.g. agonists and antagonists) of a gene encoding Ephrin type-A receptor 7 or an Ephrin type-A receptor 7-related polypeptide. An important feature of the present invention is the identification of genes encoding Ephrin type-A receptor 7 involved in bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer can be treated (e.g. to ameliorate symptoms or to retard onset or progression) or prevented by administration of a therapeutic compound that reduces function or expression of Ephrin type-A receptor 7 in the serum or tissue of subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

In one embodiment, one or more antibodies (or other affinity reagents) each specifically binding to Ephrin type-A receptor 7 are administered alone or in combination with one or more additional therapeutic compounds or treatments.

A biological product such as an antibody (or other affinity reagent) is allogeneic to the subject to which it is administered. In one embodiment, a human Ephrin type-A receptor 7 or a human Ephrin type-A receptor 7-related polypeptide, a nucleotide sequence encoding a human Ephrin type-A receptor 7 or a human Ephrin type-A receptor 7-related polypeptide, or an antibody (or other affinity reagent) to a human Ephrin type-A receptor 7 or a human Ephrin type-A receptor 7-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents) which specifically bind to Ephrin type-A receptor 7 may be achieved through the phenomenon of Antibody-Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p 2153-68 and Weng, W.-K. et al., Journal of Clinical Oncology, 2003, 21:p 3940-3947).

Treatment and Prevention of Bladder Cancer, Breast Cancer, Colorectal Cancer, Gastric Cancer, Head and Neck Cancer, Kidney Cancer, Lung Cancer, Osteosarcoma, Pancreatic Cancer, Prostate Cancer, Skin Cancer, Thyroid Cancer or Uterine Cancer, Including Metastatic Cancer Bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is treated or prevented by administration to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or to be at risk of developing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer of a compound that modulates (i.e. increases or decreases) the level or activity (i.e. function) of Ephrin type-A receptor 7 that is differentially present in the serum or tissue of subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer compared with serum or tissue of subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer. In one embodiment, bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is treated or prevented by administering to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or to be at risk of developing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer a compound that upregulates (i.e. increases) the level or activity (i.e. function) of Ephrin type-A receptor 7 that are decreased in the serum or tissue of subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Examples of such a compound include, but are not limited to, Ephrin type-A receptor 7 antisense oligonucleotides, ribozymes, antibodies (or other affinity reagents) directed against Ephrin type-A receptor 7, and compounds that inhibit the enzymatic activity of Ephrin type-A receptor 7. Other useful compounds e.g. Ephrin type-A receptor 7 antagonists and small molecule Ephrin type-A receptor 7 antagonists, can be identified using in vitro assays.

Bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is also treated or prevented by administration to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer or to be at risk of developing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer of a compound that downregulates the level or activity (i.e. function) of Ephrin type-A receptor 7 that are increased in the serum or tissue of subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Examples of such a compound include but are not limited to: Ephrin type-A receptor 7, Ephrin type-A receptor 7 fragments and Ephrin type-A receptor 7-related polypeptides; nucleic acids encoding Ephrin type-A receptor 7, an Ephrin type-A receptor 7 fragment and an Ephrin type-A receptor 7-related polypeptide (e.g. for use in gene therapy); and, for those Ephrin type-A receptor 7 or Ephrin type-A receptor 7-related polypeptides with enzymatic activity, compounds or molecules known to modulate that enzymatic activity. Other compounds that can be used, e.g. Ephrin type-A receptor 7 agonists, can be identified using in in vitro assays.

In another embodiment, therapy or prophylaxis is tailored to the needs of an individual subject. Thus, in specific embodiments, compounds that promote the level or function of Ephrin type-A receptor 7 are therapeutically or prophylactically administered to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, in whom the level or function of Ephrin type-A receptor 7 are absent or are decreased relative to a control or normal reference range. In further embodiments, compounds that promote the level or function of Ephrin type-A receptor 7 are therapeutically or prophylactically administered to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in whom the level or function of Ephrin type-A receptor 7 are increased relative to a control or to a reference range. In further embodiments, compounds that decrease the level or function of Ephrin type-A receptor 7 are therapeutically or prophylactically administered to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in whom the level or function of Ephrin type-A receptor 7 are increased relative to a control or to a reference range. In further embodiments, compounds that decrease the level or function of Ephrin type-A receptor 7 are therapeutically or prophylactically administered to a subject suspected of having or known to have bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in whom the level or function of Ephrin type-A receptor 7 are decreased relative to a control or to a reference range. The change in Ephrin type-A receptor 7 function or level due to the administration of such compounds can be readily detected, e.g. by obtaining a sample (e.g. blood or urine) and assaying in vitro the level or activity of Ephrin type-A receptor 7, or the level of mRNA encoding Ephrin type-A receptor 7, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the Ephrin type-A receptor 7 profile towards normal. The compounds of the invention may be given in combination with any other chemotherapy drugs.

Vaccine Therapy

Another aspect of the invention is an immunogenic composition, suitably a vaccine composition, comprising Ephrin type-A receptor 7 or an epitope containing fragment thereof, or nucleic acid encoding Ephrin type-A receptor 7 or a fragment thereof optionally together with an immunostimulant.

There is also provided a method of raising an immune response which comprises administering to a subject such compositions and a method for treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer which comprises administering to a subject in need thereof a therapeutically effective amount of such compositions and such compositions for use in preventing or treating bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Thus, Ephrin type-A receptor 7 may be useful as antigenic material, and may be used in the production of vaccines for treatment or prophylaxis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal. "Immunogenic" is taken to mean that the protein is capable of eliciting an immune response such as a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting e.g. a T-cell proliferation assay. The generation of an appropriate immune response may require the presence of one or more adjuvants and/or appropriate presentation of an antigen.

The skilled person will appreciate that homologues or derivatives of Ephrin type-A receptor 7 will also find use as antigenic/immunogenic material. Thus, for instance proteins which include one or more additions, deletions, substitutions or the like are encompassed by the present invention. In addition, it may be possible to replace one amino acid with another of similar "type". For instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided, for example, homologues or derivatives having at least 70% similarity, such as at least 80% similarity are provided. Particularly, homologues or derivatives having at least 90% or even 95% similarity are provided. Suitably, homologues or derivatives have at least 60% sequence identity with the proteins or polypeptides described herein. Preferably, homologues or derivatives have at least 70% identity, more preferably at least 80% identity. Most preferably, homologues or derivatives have at least 90% or even 95% identity.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of Ephrin type-A receptor 7, or of homologues or derivatives thereof.

Ephrin type-A receptor 7, or antigenic fragments thereof, can be provided alone, as a purified or isolated preparation. They may be provided as part of a mixture with one or more other proteins of the invention, or antigenic fragments thereof. In a further aspect, therefore, the invention provides an antigen composition comprising Ephrin type-A receptor 7 and/or one or more antigenic fragments thereof. Such a composition can be used for the detection and/or diagnosis of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. Other useful adjuvants will be well known to the skilled person.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204.

The adjuvants employed may be a combination of components, for example MPL and QS21 or MPL, QS21 and a CpG containing moiety.

Adjuvants may be formulated as oil-in-water emulsions or liposomal formulations.

Such preparations may include other vehicles.

In another embodiment, a preparation of oligonucleotides comprising 10 or more consecutive nucleotides complementary to a nucleotide sequence encoding Ephrin type-A receptor 7 or an Ephrin type-A receptor 7 peptide fragments is used as vaccines for the treatment of bladder cancer, breast cancer, colorectal cancer, gastric cancer, head and neck cancer, kidney cancer, lung cancer, osteosarcoma, pancreatic cancer, Inhibition of Ephrin Type-A Receptor 7 to Treat Bladder Cancer, Breast Cancer, Colorectal Cancer, Gastric Cancer, Head and Neck Cancer, Kidney Cancer, Lung Cancer, Osteosarcoma, Pancreatic Cancer, Prostate Cancer, Skin Cancer, Thyroid Cancer or Uterine Cancer, Including Metastatic Cancer In one embodiment of the invention, bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is treated or prevented by administration of a compound that antagonizes (inhibits) the level and/or function of Ephrin type-A receptor 7 which are elevated in the serum or tissue of subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer as compared with serum or tissue of subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer.

Compounds useful for this purpose include but are not limited to anti-Ephrin type-A receptor 7 antibodies (or other affinity reagents, and fragments and derivatives containing the binding region thereof), Ephrin type-A receptor 7 antisense or ribozyme nucleic acids, and nucleic acids encoding dysfunctional Ephrin type-A receptor 7 that may be used to "knockout" endogenous Ephrin type-A receptor 7 function by homologous recombination (see, e.g. Capecchi, 1989, *Science* 244:1288-1292). Other compounds that inhibit Ephrin type-A receptor 7 function can be identified by use of known in vitro assays, e.g. assays for the ability of a test compound to inhibit binding of Ephrin type-A receptor 7 to another protein or a binding partner, or to inhibit a known Ephrin type-A receptor 7 function.

Such inhibition may, for example, be assayed in vitro or in cell culture, but genetic assays may also be employed. The Preferred Technologies described herein can also be used to detect levels of Ephrin type-A receptor 7 before and after the administration of the compound. Suitable in vitro or in vivo assays are utilized to determine the effect of a specific compound and whether its administration is indicated for treatment of the affected tissue, as described in more detail below.

In a specific embodiment, a compound that inhibits Ephrin type-A receptor 7 function (activity) is administered therapeutically or prophylactically to a subject in whom an increased serum or tissue level or functional activity of Ephrin type-A receptor 7 (e.g. greater than the normal level or desired level) is detected as compared with serum or tissue of subjects with bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer who do not receive treatment according to the invention or to bring the level or activity to that found in subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer or a predetermined reference range. Methods standard in the art can be employed to measure the increase in Ephrin type-A receptor 7 level or function, as outlined above. Suitable Ephrin type-A receptor 7 inhibitor compositions may, for example, include small molecules, i.e. molecules of 1000 Daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

Thus there is provided a method of screening for compounds that modulate the activity of Ephrin type-A receptor 7, the method comprising: (a) contacting Ephrin type-A receptor 7 or a biologically active portion thereof with a candidate compound; and (b) determining whether activity of Ephrin type-A receptor 7 is thereby modulated. Such a process may comprise (a) contacting Ephrin type-A receptor 7 or a biologically active portion thereof with a candidate compound in a sample; and (b) comparing the activity of Ephrin type-A receptor 7 or a biologically active portion thereof in said sample after contact with said candidate compound with the activity of Ephrin type-A receptor 7 or a biologically active portion thereof in said sample before contact with said candidate compound, or with a reference level of activity.

The method of screening may be a method of screening for compounds that inhibit activity of Ephrin type-A receptor 7.

Ephrin type-A receptor 7 or a biologically active portion thereof may, for example be expressed on or by a cell. Ephrin type-A receptor 7 or a biologically active portion thereof may, for example, be isolated from cells which express it. Ephrin type-A receptor 7 or a biologically active portion thereof may, for example, be immobilised onto a solid phase.

There is also provided a method of screening for compounds that modulate the expression of Ephrin type-A receptor 7 or nucleic acid encoding Ephrin type-A receptor 7, the method comprising: (a) contacting cells expressing Ephrin type-A receptor 7 or nucleic acid encoding Ephrin type-A receptor 7 with a candidate compound; and (b) determining whether expression of Ephrin type-A receptor 7 or nucleic acid encoding Ephrin type-A receptor 7 is thereby modulated. Such a process may comprise (a) contacting cells expressing Ephrin type-A receptor 7 or nucleic acid encoding Ephrin type-A receptor 7 with a candidate compound in a sample; and (b) comparing the expression of Ephrin type-A receptor 7 or nucleic acid encoding Ephrin type-A receptor 7 by cells in said sample after contact with said candidate compound with the expression of Ephrin type-A receptor 7 or nucleic acid encoding Ephrin type-A receptor 7 of cells in said sample before contact with said candidate compound, or with a reference level of expression.

The method may be a method of screening for compounds that inhibit expression of Ephrin type-A receptor 7 or nucleic acid encoding Ephrin type-A receptor 7.

Other aspects of the invention include: a compound obtainable by an aforementioned screening method, a compound which modulates the activity or expression of Ephrin type-A receptor 7 or nucleic acid encoding Ephrin type-A receptor 7, for example a compound which inhibits the activity or expression of Ephrin type-A receptor 7 or nucleic acid encoding Ephrin type-A receptor 7.

Such a compound is provided for use in treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

There is also provided a method for treating or preventing bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer which comprises administering to a subject in need thereof a therapeutically effective amount of such a compound.

Test compounds can be assayed for their ability to restore Ephrin type-A receptor 7 levels in a subject having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer towards levels found in subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer or to produce similar changes in experimental animal models of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Compounds able to restore Ephrin type-A receptor 7 levels in a subject having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer towards levels found in subjects free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer or to produce similar changes in experimental animal models of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer can be used as lead compounds for further drug discovery, or used therapeutically. Ephrin type-A receptor 7 expression can be assayed by the Preferred Technologies described herein, immunoassays, gel electrophoresis followed by visualization, detection of Ephrin type-A receptor 7 activity, or any other method taught herein or known to those skilled in the art. Such assays can be used to screen candidate drugs, in clinical monitoring or in drug development, where abundance of Ephrin type-A receptor 7 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer include, but are not limited to xenografts of bladder cancer cell lines such as UCRU-BL-12, UCRU-BL-13 and UCRU-BL-14, Russell et al. Cancer Res. 1986 April; 46(4 Pt 2):2035-40; xenografts of breast cancer cell lines such as MCF-7, Ozzello L, Sordat M., Eur J Cancer. 1980; 16:553-559 and MCF10AT, Miller et al., J Natl Cancer Inst. 1993; 85:1725-1732 in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of head and neck cancer cell lines such as FaDu and HNX-OE; xenografts of renal cell cancer cell lines such as LABAZ1 in immune compromised mice, Zisman et al, Cancer Research 63, 4952-4959, Aug. 15, 2003; xenografts of non small cell lung cancer cell lines such as A549 and H460 and xenografts of small cell lung cancer cell lines such as NCI-H345; xenografts of human osteosarcoma cell lines such as HuO9 in nude mice, Kimura et al., Clin Exp Metastasis 2002; 19(6):477-85; xenografts of pancreatic cancer cell lines such as MIA PaCa-2 in nude mice, Marincola et al., J Surg Res 1989 December; 47(6):520-9; xenografts of prostate cancer cell lines such as CWR-22 in nude mice, Pretlow et al, J Natl Cancer Inst. 1993 Mar. 3; 85(5):394-8; xenografts of skin cancer cell lines such as MV3 in nude mice, van Muijen et al, Int J Cancer 1991 Apr. 22; 48(1):85-91; xenografts of thyroid cancer cell lines such as ARO, Viaggi et al., Thyroid 2003 June; 13(6):529-36; and xenografts of uterine cancer cell lines such as HEC-1A and RL-95-2, Li et al., J Cancer Res Clin Oncol. 2007 May; 133(5):315-20. These can be utilized to test compounds that modulate Ephrin type-A receptor 7 levels, since the pathology exhibited in these models is similar to that of bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer. It is also apparent to the skilled artisan that based upon the present disclosure, transgenic animals can be produced with "knock-out" mutations of the gene or genes encoding Ephrin type-A receptor 7. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of Ephrin type-A receptor 7 are identified in non-human animals (e.g. mice, rats, monkeys, rabbits, and guinea pigs), preferably non-human animal models for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, expressing Ephrin type-A receptor 7. In accordance with this embodiment, a test compound or a control compound is administered to the animals, and the effect of the test compound on expression of Ephrin type-A receptor 7 is determined. A test compound that alters the expression of Ephrin type-A receptor 7 can be identified by comparing the level of Ephrin type-A receptor 7 (or mRNA encoding the same) in an animal or group of animals treated with a test compound with the level of Ephrin type-A receptor 7 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of Ephrin type-A receptor 7 or a biologically active portion thereof are identified in non-human animals (e.g. mice, rats, monkeys, rabbits, and guinea pigs), preferably non-human animal models for bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, expressing Ephrin type-A receptor 7. In accordance with this embodiment, a test compound or a control compound is administered to the animals, and the effect of a test compound on the activity of Ephrin type-A receptor 7 is determined. A test compound that alters the activity of Ephrin type-A receptor 7 can be identified by assaying animals treated with a control compound and animals treated with the test compound. The activity of Ephrin type-A receptor 7 can be assessed by detecting induction of a cellular second messenger of Ephrin type-A receptor 7 (e.g. intracellular $Ca^{2+}$, diacylglycerol, IP3, etc.), detecting catalytic or enzymatic activity of Ephrin type-A receptor 7 or binding partner thereof, detecting the induction of a reporter gene (e.g. a regulatory element that is responsive to Ephrin type-A receptor 7 operably linked to a nucleic acid encoding a detectable marker, such as luciferase or green fluorescent protein), or detecting a cellular response (e.g. cellular differentiation or cell proliferation). Techniques known to those of skill in the art can be utilized to detect changes in the activity of Ephrin type-A receptor 7 (see, e.g. U.S. Pat. No. 5,401,639, which is incorporated herein by reference).

In yet another embodiment, test compounds that modulate the level or expression of Ephrin type-A receptor 7 are identified in human subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, preferably those having severe bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. In accordance with this embodiment, a test compound or a control compound is administered to the human subject, and the effect of a test compound on Ephrin type-A receptor 7 expression is determined by analyzing the expression of Ephrin type-A receptor 7 or the mRNA encoding the same in a biological sample (e.g. serum, plasma, or urine). A test compound that alters the expression of Ephrin type-A receptor 7 can be identified by comparing the level of Ephrin type-A receptor 7 or mRNA encoding the same in a subject or group of subjects treated with a control compound to that in a subject or group of subjects treated with a test compound. Alternatively, alterations in the expression of Ephrin type-A receptor 7 can be identified by comparing the level of Ephrin type-A receptor 7 or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of Ephrin type-A receptor 7.

In another embodiment, test compounds that modulate the activity of Ephrin type-A receptor 7 are identified in human subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer (preferably those with severe bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer). In this embodiment, a test compound or a control compound is administered to the human subject, and the effect of a test compound on the activity of Ephrin type-A receptor 7 is determined. A test compound that alters the activity of Ephrin type-A receptor 7 can be identified by comparing biological samples from subjects treated with a control compound to samples from subjects treated with the test compound. Alternatively, alterations in the activity of Ephrin type-A receptor 7 can be identified by comparing the activity of Ephrin type-A receptor 7 in a subject or group of subjects before and after the administration of a test compound. The activity of Ephrin type-A receptor 7 can be assessed by detecting in a biological sample (e.g. serum, plasma, or urine) induction of a cellular signal transduction pathway of Ephrin type-A receptor 7 (e.g. intracellular $Ca^{2+}$, diacylglycerol, IP3, etc.), catalytic or enzymatic activity of Ephrin type-A receptor 7 or a binding partner thereof, or a cellular response, for example, cellular differentiation, or cell proliferation. Techniques known to those of skill in the art can be used to detect changes in the induction of a second messenger of Ephrin type-A receptor 7 or changes in a cellular response. For example, RT-PCR can be used to detect changes in the induction of a cellular second messenger.

In another embodiment, a test compound that changes the level or expression of Ephrin type-A receptor 7 towards levels detected in control subjects (e.g. humans free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer) is selected for further testing or therapeutic use. In another embodiment, a test compound that changes the activity of Ephrin type-A receptor 7 towards the activity found in control subjects (e.g. humans free from bladder cancer, breast cancer, colorectal cancer, gastric cancer, head and neck cancer, kidney cancer, lung cancer, osteosarcoma, pancreatic cancer, prostate cancer, skin cancer, thyroid cancer and uterine cancer, including metastatic cancer) is selected for further testing or therapeutic use.

In another embodiment, test compounds that reduce the severity of one or more symptoms associated with bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer are identified in human subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer, preferably subjects with severe bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. In accordance with this embodiment, a test compound or a control compound is administered to the subjects, and the effect of a test compound on one or more symptoms of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is determined. A test compound that reduces one or more symptoms can be identified by comparing the subjects treated with a control compound to the subjects treated with the test compound. Techniques known to physicians familiar with bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer can be used to determine whether a test compound reduces one or more symptoms associated with bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. For example, a test compound that reduces tumour burden in a subject having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer will be beneficial for subjects having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer.

In another embodiment, a test compound that reduces the severity of one or more symptoms associated with bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer in a human having bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer is selected for further testing or therapeutic use.

Therapeutic and Prophylactic Compositions and their Use

The invention provides methods of treatment (and prophylaxis) comprising administering to a subject an effective amount of a compound of the invention. In a particular aspect, the compound is substantially purified (e.g. substantially free from substances that limit its effect or produce undesired side-effects). The subject is for example an animal, including but not limited to animals such as cows, pigs, horses, chickens, cats, dogs, etc., and is for example a mammal, such as a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g. encapsulation in liposomes, microparticles, microcapsules, recombinant cells capable of expressing the compound, receptor-mediated endocytosis (see, e.g. Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In one aspect of the invention a nucleic acid employed in the invention may be delivered to the dermis, for example employing particle mediated epidermal delivery.

In a specific embodiment, it may be desirable to administer the pharmaceutical compositions of the invention locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sialastic membranes, or fibers. In one embodiment, administration can be by direct injection into bladder, breast, colorectal, head and neck, kidney, lung, osteoblast, pancreatic, prostate, skin, thyroid or uterine tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e. the bladder, breast, colon, stomach, head/neck, kidney, lung, bone, pancreas, prostate, skin, thyroid or uterus thus requiring only a fraction of the systemic dose (see, e.g. Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g. by use of a retroviral vector (see U.S. Pat. No. 4,980,286), or by direct injection, or by use of microparticle bombardment (e.g. a gene gun; Biolistic, Dupont), or coating with lipids or cell-surface receptors or transfecting agents, or by administering it in linkage to a homeobox-like peptide which is known to enter the nucleus (see e.g. Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means suitable for approval by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, for example in purified form, together with a suitable amount of carrier so as to provide the form for proper administration to the subject. The formulation should suit the mode of administration.

In one embodiment, for example where one or more antibodies are employed, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts, where appropriate, include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Thus in one aspect the kit comprises antibodies employed in the invention, for example the antibodies may be lyophilized for reconstitution before administration or use. Where the kit is for use in therapy/treatment such as cancer the antibody or antibodies may be reconstituted with an isotonic aqueous solution, which may optionally be provided with the kit. In one aspect the kit may comprise a polypeptide such as an immunogenic polypeptide employed in the invention, which may for example be lyophilized. The latter kit may further comprise an adjuvant for reconstiting the immunogenic polypeptide.

The invention also extends to a composition as described herein for example a pharmaceutical composition and/or vaccine composition for use in inducing an immune response in a subject.

Determining Abundance of Ephrin Type-A Receptor 7 by Imaging Technology

An advantage of determining abundance of Ephrin type-A receptor 7 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of Ephrin type-A receptor 7 using such techniques requires incorporation or binding of a suitable label e.g. a radiotracer such as $^{18}F$, $^{11}C$ or $^{123}I$ (see e.g. NeuroRx—The Journal of the American Society for Experimental NeuroTherapeutics (2005) 2(2), 348-360 and idem pages 361-371 for further details of the techniques). Radiotracers or other labels may be incorporated into Ephrin type-A receptor 7 by administration to the subject (e.g. by injection) of a suitably labelled specific ligand. Alternatively they may be incorporated into a binding affinity reagent (e.g. an antibody) specific for Ephrin type-A receptor 7 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding Affibody molecule, Cancer Res. 2006 Apr. 15; 66(8): 4339-48).

Diagnosis and Treatment of Bladder Cancer, Breast Cancer, Colorectal Cancer, Gastric Cancer, Head and Neck Cancer, Kidney Cancer, Lung Cancer, Osteosarcoma, Pancreatic Cancer, Prostate Cancer, Skin Cancer, Thyroid Cancer or Uterine Cancer, Including Metastatic Cancer Using Immunohistochemistry Immunohistochemistry is an excellent detection technique and may therefore be very useful in the diagnosis and treatment of bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer. Immunohistochemistry may be used to detect, diagnose, or monitor bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer through the localization of Ephrin type-A receptor 7 antigens in tissue sections by the use of labeled antibodies (or other affinity reagents), derivatives and analogs thereof, which specifically bind to Ephrin type-A receptor 7, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutic approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

Preferred features of each aspect of the invention are as for each of the other aspects mutatis mutandis. The prior art documents mentioned herein are incorporated to the fullest extent permitted by law.

EXAMPLE 1

Identification of Membrane Proteins Expressed in Colorectal Cancer and Osteosarcoma Tissue Samples Using 1D Gel Electrophoresis Using the following Reference Protocol, membrane proteins extracted from colorectal cancer and osteosarcoma tissue samples were separated by 1D gel and analysed.
1.1 Materials and Methods
1.1.1—Plasma Membrane Fractionation The cells recovered from colorectal cancer or osteosarcoma were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was either run directly on 1D gels (see section 1.1.4 below), or further fractionated into heparin binding and nucleotide binding fractions as described below.
1.1.2—Plasma Membrane Heparin-Binding Fraction The pooled solution from 1.1.1 above was applied to a Heparin column, eluted from column and run on 1D gels (see section 1.1.4 below).
1.1.3—Plasma Nucleotide-Binding Fraction The pooled solution from 1.1.1 above was applied to a Cibacrom Blue 3GA column, eluted from column and run on 1D gels (see section 1.1.4 below).

1.1.4—1D Gel Technology

Protein or membrane pellets were solubilised in 1D sample buffer (1-2 µg/µl). The sample buffer and protein mixture was then heated to 95° C. for 3 min.

A 9-16% acrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent and the molecular weight standards (66, 45, 31, 21, 14 kDa) were added to the stacking gel wells using a 10 microliter pipette tip and the samples run at 40 mA for 5 hours.

The plates were then prised open, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 µl)) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and Analysis of Selected Proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analyzed by mass spectrometry using a PerSeptive Biosystems Voyager-DETM STR Matrix-Assisted Laser Desorption Ionization Time-of-Flight (MALDI-TOF) mass spectrometer, and selected tryptic peptides were analyzed by tandem mass spectrometry (MS/MS) using a Micromass Quadrupole Time-of-Flight (Q-TOF) mass spectrometer (Micromass, Altrincham, U.K.) equipped with a nanoflow™ electrospray Z-spray source. For partial amino acid sequencing and identification of Ephrin type-A receptor 7, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI) which is accessible at www.ncbi.nlm.nih.gov. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun. Mass Spectrom. 6:658-662).

1.1.6—Discrimination of Colorectal Cancer and Osteosarcoma Associated Proteins

The process to identify Ephrin type-A receptor 7 uses the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to Form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.
4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.
5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome.

Various elimination rules, based on cluster observation scoring and multiple mapping to the genome are used to refine the output. The resulting 'confirmed genes' are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 506 genes in bladder cancer, 4,713 genes in breast cancer, 766 genes in burkitt's lymphoma, 1,371 genes in cervical cancer, 949 genes in colorectal cancer, 1,782 genes in hepatocellular carcinoma, 2,424 genes in chronic lymphocytic leukaemia, 978 genes in lung cancer, 1,764 genes in melanoma, 1,033 genes in ovarian cancer, 2,961 genes in pancreatic cancer and 3,307 genes in prostate cancer, illustrated here by Ephrin type-A receptor 7 isolated and identified from breast cancer, colorectal cancer, lung cancer, osteosarcoma and prostate cancer samples. Following comparison of the experimentally determined sequences with sequences in the OGAP® database, Ephrin type-A receptor 7 showed a high degree of specificity to breast cancer, colorectal cancer, lung cancer, osteosarcoma and prostate cancer indicative of the prognostic and diagnostic nature.

1.2 Results

These experiments identified Ephrin type-A receptor 7, as further described herein. The full-length Ephrin type-A receptor 7 was detected in the plasma membrane of colorectal cancer and osteosarcoma samples and was not detected in the cytosol.

The Protein Index was calculated for Ephrin type-A receptor 7. For each gene, the protein index uses the mass spectrometry data to assign a score to each disease, relative to the global database. The Protein Index can then be used to identify cancer specific genes with a high score in cancer indications and low/negligible scores in normal and other diseases. The index contains ~1 million peptides sequenced via mass spectrometry from 56 diseases. For each gene, this yields a score for each disease and subcellular location.

The Protein Index for Ephrin type-A receptor 7 is medium in breast cancer whole cell (see Example 3 below), medium in colorectal cancer plasma membrane, medium in lung cancer plasma membrane (see Example 2 below), medium in osteosarcoma plasma membrane, high in prostate cancer membrane (see Example 4 below) and very low in normal plasma membrane, membrane and whole cell. Ephrin type-A receptor 7 was not detected in any other diseases. This indicates that Ephrin type-A receptor 7 is potentially a good target for breast cancer, colorectal cancer, lung cancer, osteosarcoma and prostate cancer.

EXAMPLE 2

Identification of Membrane Proteins Expressed in Colorectal Cancer and Lung Cancer Tissue Samples Using Isotope Tagging for Absolute and Relative Quantitation (iTRAQ)

Using the following Reference Protocol, membrane proteins extracted from colorectal cancer and lung cancer tissue and normal adjacent colorectal and lung tissue samples were digested, labelled with Isotope Tagging for Absolute & Relative Quantitation reagents (iTRAQ; Applied Biosystems, Foster City, Calif., USA) and the resulting relative peptide expression levels determined by MRM mass spectrometry.

2.1 Materials and Methods 2.1.1—Plasma Membrane Fractionation

The cells recovered from a colorectal cancer or lung cancer or normal adjacent colorectal or lung tissue were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was then analysed directly by iTRAQ (see section 2.1.2 below).

2.1.2—iTRAQ Methodology

Membrane protein pellets from colorectal cancer or lung cancer and normal adjacent colorectal or lung tissue were solubilised in sample buffer (2-4 µg/µl in 0.5% SDS) by the addition of buffer and then heating to 95° C. for 3 min.

To a volume of each protein solution equating to 50 µg, 150 µl of 0.5M triethylammonium bicarbonate (TEAB) solution was added. To each sample, 3 µl of 50 mM tris-(2-carboxyethyl)phosphine was added and the mixture was incubated at 60° C. for 1 hour. 1 µl of cysteine blocking reagent, 200 mM methyl methanethiosulphonate (MMTS) in isopropanol, was then added. After incubation at room temperature for 10 minutes, 15 µl of 1 µg/µl trypsin was added to each sample followed by incubation at 37° C. overnight.

The digested samples were dried under a vacuum and re-constituted with 30 µl of 0.5M TEAB solution. 70 µl ethanol was added to each of the four iTRAQ reagents (114/115/116/117) and one reagent added to each of the four samples analysed (two colorectal cancer or lung cancer samples and two corresponding normal adjacent tissue samples) and left at room temperature for 1 hour. The specific reagent added to each sample was recorded. The four labeled samples were combined & vortexed.

The combined sample was reduced to dryness under a vacuum and de-salted by loading onto a C18 spin column, washing with aqueous solvent and then eluting with 70% acetonitrile. The sample fraction was again reduced to dryness and then re-dissolved in 40 µl of solvent A (97.9 water, 2% acetonitrile, 0.1% formic acid) prior to ion exchange fractionation.

2.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 µm; 50×0.8 mm) using a 20 µl/min gradient of 0-100 mM sodium acetate over 20 minutes and then to 1M over 10 minutes. 1 minute fractions were collected over the 30 minute run.

Each fraction was analysed by liquid chromatography/mass spectrometry using a Tempo chromatograph (Applied Biosystems, Framingham, Mass., USA) fitted with a PepMap 100-C18 150 mm×75 μm column (Dionex Corporation, Sunnyvale, Calif., USA) and a 4000 Q Trap hybrid triple quadrupole/linear ion trap instrument (Applied Biosystems, Framingham, Mass., USA). Peptides were eluted with a 300 nl/min gradient increasing from 5% to 40% acetonitrile in 60 minutes. Data was acquired in MRM mode by selecting up to 6 precursor ions (Q1) and 6 fragment ions (Q3) consisting of the 4 iTRAQ reporter ions and the 2y and 1b above precursor sequence ions. Peak areas from the 6 fragment ions were analysed to produce a ratio of the relative peptide expression levels between the colorectal cancer and lung cancer samples and their matched normal adjacent samples.

2.2 Results

These experiments identified Ephrin type-A receptor 7, as further described herein. The analysis of the ratio of the relative peptide expression levels between the colorectal cancer and lung cancer samples and their matched normal adjacent samples showed that levels of Ephrin type-A receptor 7 in the cancer samples were higher than in the matched normal adjacent tissue samples.

See Example 1 section 1.2 for a description of the Protein Index for Ephrin type-A receptor 7.

EXAMPLE 3

Identification of Proteins Expressed in Breast Cancer Tissue Lysate Samples Using Isotope Tagging for Absolute and Relative Quantitation (iTRAQ)

Using the following Reference Protocol, breast cancer tissue lysates and normal adjacent breast tissue samples were digested, labelled with Isotope Tagging for Absolute & Relative Quantitation reagents (iTRAQ; Applied Biosystems, Foster City, Calif., USA) and the resulting relative peptide expression levels determined by MRM mass spectrometry.

3.1 Materials and Methods 31.1—Breast Lysates

Human breast tissue lysates from breast cancer and normal adjacent tissue were obtained from Protein Biotechnologies at a concentration of 1 mg/ml.

The lysates were then analysed directly by iTRAQ (see section 3.1.2 below).

3.1.2—iTRAQ Methodology

To a volume of each protein solution equating to 50 μg, 20 μl of 0.5M triethylammonium bicarbonate (TEAB) solution was added. To each sample, 2 μl of 50 mM tris-(2-carboxyethyl)phosphine was added and the mixture was incubated at 60° C. for 1 hour. 1 μl of cysteine blocking reagent, 200 mM methyl methanethiosulphonate (MMTS) in isopropanol, was then added. After incubation at room temperature for 10 minutes, 5 μl of 1 μg/μl trypsin was added to each sample followed by incubation at 37° C. overnight.

The digested samples were dried under a vacuum and re-constituted with 30 μl of 0.5M TEAB solution. 50 μl isopropanol was added to each of the eight iTRAQ reagents (113/114/115/116/117/118/119/121) and one reagent added to each of the eight samples analysed (four breast cancer samples and four corresponding normal adjacent tissue samples) and left at room temperature for 2 hours. The specific reagent added to each sample was recorded. The eight labeled samples were combined & vortexed.

The combined sample was reduced to dryness under a vacuum and de-salted by loading onto a C18 spin column, washing with aqueous solvent and then eluting with 70% acetonitrile. The sample fraction was again reduced to dryness and then re-dissolved in 40 μl of solvent A (97.9 water, 2% acetonitrile, 0.1% formic acid) prior to ion exchange fractionation.

3.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 μm; 50×0.8 mm) using a 20 μl/min gradient of 0-100 mM sodium acetate over 20 minutes and then to 1M over 10 minutes. 1 minute fractions were collected over the 30 minute run.

Each fraction was analysed by liquid chromatography/mass spectrometry using a Tempo chromatograph (Applied Biosystems, Framingham, Mass., USA) fitted with a PepMap 100-C18 150 mm×75 μm column (Dionex Corporation, Sunnyvale, Calif., USA) and a 4000 Q Trap hybrid triple quadrupole/linear ion trap instrument (Applied Biosystems, Framingham, Mass., USA). Peptides were eluted with a 300 nl/min gradient increasing from 5% to 40% acetonitrile in 60 minutes. Data was acquired in MRM mode by selecting up to 10 precursor ions (Q1) and 10 fragment ions (Q3) consisting of the 8 iTRAQ reporter ions and the 2y and 1b above precursor sequence ions. Peak areas from the 10 fragment ions were analysed to produce a ratio of the relative peptide expression levels between the breast cancer samples and their matched normal adjacent samples.

3.2 Results

These experiments identified Ephrin type-A receptor 7, as further described herein. The analysis of the ratio of the relative peptide expression levels between the breast cancer samples and their matched normal adjacent samples showed that levels of Ephrin type-A receptor 7 in the cancer samples were higher than in the matched normal adjacent breast tissue samples.

See Example 1 section 1.2 for a description of the Protein Index for Ephrin type-A receptor 7.

EXAMPLE 4

Identification of Membrane Proteins Expressed in Prostate Cancer Blood and Tissue Samples Using the following Reference Protocol, membrane proteins extracted from prostate cancer tissue samples were analysed using Isotope-Coded Affinity Tags (ICAT).

4.1 Materials and Methods 4.1.1—Preparation of Membrane Fractions

The cells recovered from a prostate cancer were lysed and submitted to centrifugation at 1000 G. The supernatant was taken, and it was subsequently centrifuged at 3000 G. Once again, the supernatant was taken, and it was then centrifuged at 100 000 G.

The resulting pellets were dissolved by boiling in labeling buffer (50 mM Tris-HCl pH 8.3, 5 mM EDTA, 0.5% SDS), and the protein concentration was measured.

A Western blot was used to verify membrane protein markers.

4.1.2—Synthesis of ICAT Reagents

The ICAT reagents used were synthesized with the following isotopically different substrates: 4,7,10-trioxa-1,13-tridecanediamine (A) (Aldrich, Milwaukee, Wis.) and 2,2',3,3',11, 11',12,12'-octadeutero-4,7,10-trioxa-1,13-tridecanediamine (B) (Gerber, S. A., Scott, C. R., Turecek, F. & Gelb, M. H. Analysis of rates of multiple enzymes in cell lysates by electrospray ionization mass spectrometry. *J. Am. Chem. Soc.* 121, 1102-1103 (1999)). Synthesis of N-(13-amino-4,7,10-trioxatridecanyl)biotinamide (C) was as follows. To biotin-pentafluorophenylester (Pierce, Rockford, Ill.) in dry dimethylformamide containing excess N,N-diisopropylethylamine (Aldrich) were added five equivalents of (A) with stirring at room temperature for 3 h. Solvent was removed under reduced pressure and (C) was purified to homogeneity by reverse-phase HPLC. The heavy analog was prepared as per (C), but with five equivalents of (B). Synthesis of N-(13-iodoacetamido-4,7,10-trioxatridecanyl)biotinamide (D) was as follows. To (C) (or heavy analog) in dry dimethylformamide containing excess N,N-diisopropylethylamine was added two equivalents iodoacetic anhydride (Aldrich) with stirring at room temperature for 3 h. Solvent was removed under reduced pressure, and (D) was purified to homogeneity by reverse-phase HPLC and characterized by MS.

4.1.3—ICAT Analysis 100 ug of total protein was used. Disulfide bonds in the denatured protein mixtures were reduced (50 mM Tris buffer pH 8.5, 6 M guanidine HCl, 5 mM tributyl phosphine) for 1 h at 37° C. Cysteinyl groups in each mixture were independently biotinylated with a fivefold molar excess of the appropriate ICAT reagent. Excess ICAT reagent was removed from the combined samples by gel filtration (Bio-Rad, Richmond, Calif.) in Tris buffer (50 mM, pH 8.5) with 0.1% SDS, and the protein fraction was digested with trypsin (Promega, Madison, Wis.) overnight at 37° C. The peptide solution was then passed over a prepared monomeric avidin column (Pierce). The column was washed with water, and biotinylated peptides were eluted with 0.3% formic acid (1 ml fractions). The volume of sample eluted (in 0.3% formic acid) was reduced from 1,000 to 50 ul. Peptide recovery across the entire procedure was estimated at approximately 70%.

An LCQ ion trap mass spectrometer (Finnigan MAT, San Jose, Calif.) was used with an in-house fabricated microelectrospray source (see e.g. Figeys, D. et al. Electrophoresis combined with novel mass spectrometry techniques: powerful tools for the analysis of proteins and proteomes. *Electrophoresis* 19, 1811-1818 (1998)) and an HP1100 solvent delivery system (Hewlett Packard, Palo Alto, Calif.). A 60 min binary gradient with 5-80% solvent B (acetonitrile and 0.005% heptafluorobutyric acid (HFBA)). Solvent A consisted of 0.4% acetic acid and 0.005% HFBA. A flow rate of 0.5 ul/min was used with a 100 um×12 cm fused silica capillary column in-house packed with Monitor spherical silica (Column Engineering, Ontario, Calif.). Functional chromatography has been achieved with this setup with peptide loads as high as 500 pmol. in H2O. One microliter of the peptide mixture was pressure loaded onto the column. Eluting peptides were analyzed by uLC-MS and uLC-MS/MS techniques as described elsewhere (see e.g. Gygi, S. P., Rochon, Y., Franza, B. R. & Aebersold, R, Correlation between protein and mRNA abundance in yeast, *Mol. Cell. Biol.* 19, 1720-1730 (1999) and Gygi, S. P., Han, D. K. M., Gingras, A. C., Sonenberg, N. & Aebersold, R, Protein analysis by mass spectrometry and sequence database searching: tools for cancer research in the post-genomic era, *Electrophoresis* 20, 310-319 (1999)). The intensities of eluting peptide pairs were measured in the scanning mass spectrometer. There is a slight difference in the elution times of differentially tagged peptide pairs, with the heavy analog eluting 1-2 s before the light analog. For this reason, the entire peak area of each eluting peptide was reconstructed and used in the ratio calculation. To determine the amino acid sequence, the mass spectrometer operated in a data-dependent MS/MS mode (a full-scan mass spectrum is followed by a tandem mass spectrum), where the precursor ion is selected "on the fly" from the previous scan. An m/z ratio for an ion that had been selected for fragmentation was placed in a list and dynamically excluded for 1 min from further fragmentation. For partial amino acid sequencing and identification of Ephrin type-A receptor 7, uninterpreted tandem mass spectra of tryptic peptides were searched using the SEQUEST search program (Eng, J., McCormack, A. L. & Yates, J. R. An approach to correlate tandem mass spectral data of peptides with amino acid sequences in a protein database. *J. Am. Soc. Mass Spectrom.* 5, 976-989 (1994)), which searched tandem mass spectra against the OWL nonredundant sequence database (Bleasby, A. J., Akrigg, D. & Attwood, T. K. OWL—a non-redundant composite protein sequence database. *Nucleic Acids Res.* 22, 3574-3577 (1994)).

4.1.4—Discrimination of Prostate Cancer Associated Proteins

The process described in Example 1 section 1.1.6 was employed to discriminate the prostate cancer associated proteins in the experimental samples.

4.2 Results

These experiments identified Ephrin type-A receptor 7, as further described herein. The full-length Ephrin type-A receptor 7 was detected in the membrane of prostate cancer samples and was not detected in the cytosol.

See Example 1 section 1.2 for a description of the Protein Index for Ephrin type-A receptor 7.

EXAMPLE 5

Immunohistochemistry Using Antibody to Ephrin Type-A Receptor 7

Using the following Reference Protocol, immunohistochemistry was performed on FFPE tumour and normal tissues using a rabbit polyclonal antibody to Ephrin type-A receptor 7 (Abcam, UK, ab5400).

5.1 Materials and Methods

Anti-rabbit EnVision plus kit (K4010) was from DAKO, CA, USA.

EZ-De-Wax was from BioGenex, CA, USA.

Tissue sections and arrays were from Biomax, MD, USA.

5.1.1—Deparaffinisation and Rehydration

Slides were heated for 2 h at 60° C. in 50 ml Falcons in a water bath with no buffer. Each Falcon had one slide or two slides back-to back with long gel loading tip between them to prevent slides from sticking to each other. Slides were deparaffinised in EZ-DeWax for 5 min in black slide rack, then rinsed well with the same DeWax solution using 1 ml pipette, then washed with water from the wash bottle. Slides were placed in a coplin jar filled with water until the pressure cooker was ready; the water was changed a couple of times.

5.1.2—Antigen Retrieval

Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 minutes. Then the hob was switched off and the cooker was placed onto the cold hob and the pressure was released by carefully moving the handle into the position between "open" and "closed". The whole system was left to release the pressure and to cool down for another 20 minutes. The lid was opened and samples taken out to rest on the bench. The slides were washed 1×5 min with PBS-3T (0.5 L PBS+3 drops of Tween-20) and the slides were placed in PBS.

5.1.3.—Staining

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T and 1×2 ml PBS, waiting until all PBS had gone through the slide and virtually no PBS was left in the funnel.

Endogenous peroxide blockade was performed using solution supplied with EnVision+kits. 1-4 drops of peroxide solution was used per slide and incubated for 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilutions were determined to be 1:75 and 1:50. 50-200 μl of diluted primary antibody was applied to each section and/or tissue microarray; taking care to cover the whole tissue. The slide was gently tapped to distribute the antibody evenly over the section or a pipette tip was used over the top of the section. The slide was incubated for 45 minutes in a moist chamber at room temperature. Slides were washed with 2×2 ml (or 4×1 ml) PBS-3T and then 1×2 ml PBS, waiting until all PBS had gone through the slide and virtually no PBS was left in the funnel.

The anti-rabbit peroxidase polymer was applied 2×2 drops per slide and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time. All of the DAB was distributed between the slides. The slides were incubated for 10 min. The slides were washed 1×2 ml (or 2×1 ml) with PBS-3T and 1×2 ml (or 2×1 ml) with PBS, waiting until all PBS had gone through the slide and virtually no PBS was left in the funnel.

Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into black slide rack. Tissues were dehydrated by incubating in EZ-DeWax for 5 min and then in 95% ethanol for 2-5 min.

Slides were left to dry on the bench at room temperature and then mounted in mounting media and covered with coverslip.

5.2 Results

Immunohistochemical analysis revealed specific staining of tumor cells. Distinct cytoplasmic staining was observed in normal cells whereas in the cancer cells it was evident that delocalization of the cancer cells resulted in most of the cells being heavily stained in the plasma membrane and cytoplasm. Scoring of clinical samples was therefore based on observation of membrane and cytoplasmic staining in cancer tissues.

Table 4 below shows the results of tissue arrays of colorectal cancer, lung cancer and metastatic tumours. In a colorectal tissue array representing 74 patients with colorectal cancer, elevated staining of Ephrin type-A receptor 7 was noted in tumor cells of 43 patients (56%), compared to normal adjacent tissue. In a lung tissue array representing 76 patients with lung cancer, elevated staining of Ephrin type-A receptor 7 in cancer cells, compared to normal adjacent tissue, was seen in 27 patients (35%). In a tissue array representing 18 additional patients with metastatic colorectal, gastric, breast, lung and thyroid tumours, elevated staining of Ephrin type-A receptor 7 in cancer cells, compared to normal adjacent tissue, was seen in 16 patients (89%). Metastatic breast cancer showed particularly strong staining with invasion of the surrounding stroma in a single-file pattern known as Indian filing.

Table 5 below shows the results of a high density array containing 500 tissue cores from the 20 most common types of cancer (20 cases/type) and normal controls (5 cases/type). Elevated staining of Ephrin type-A receptor 7 in cancer cells was seen in colorectal cancer, bladder cancer, uterine cancer, head and neck cancer, skin cancer, kidney cancer, thyroid cancer and pancreatic cancer.

In a normal tissue array, expression was highly restricted with only very weak, diffuse staining observed in some tissues and no staining at all in most tissues.

TABLE 4

Ephrin type-A receptor 7 scoring on tissue microarrays (Biomax, US)

| Tissue Array | No. of Patients Negative | No. of Patients Positive | No. of Patients Strongly Positive |
|---|---|---|---|
| Colorectal cancer | 31 | 15 | 28 |
| Lung cancer | 49 | 20 | 7 |
| Metastatic tumours | 2 | 6 | 10 |

TABLE 5

Ephrin type-A receptor 7 scoring on tissue microarray (Biomax, US).

| Tissue | Malignant (%) | | | |
|---|---|---|---|---|
| | + | ++ | +++ | Total |
| Colon | 19 | 29 | 33 | 81 |
| Bladder | 25 | 35 | 20 | 80 |
| Uterus | 15 | 20 | 15 | 50 |
| Head and neck | 28 | 22 | 11 | 61 |
| Skin | 19 | 38 | 10 | 67 |
| Kidney | 20 | 15 | 10 | 45 |
| Thyroid | 20 | 15 | 10 | 45 |
| Pancreas | 35 | 35 | 5 | 75 |
| Cerebrum | 45 | 10 | 5 | 60 |
| Liver | 15 | 5 | 5 | 25 |
| Stomach | 48 | 4 | 4 | 56 |
| Breast | 20 | 20 | 3 | 43 |
| Lung | 23 | 20 | 0 | 43 |
| Prostate | 35 | 0 | 0 | 35 |
| Ovary | 18 | 6 | 0 | 24 |
| Lymph node | 20 | 0 | 0 | 20 |
| Testis | 0 | 5 | 0 | 5 |
| Bone | 0 | 0 | 0 | 0 |
| Fatty tissue | 0 | 0 | 0 | 0 |
| Fibrous tissue | 0 | 0 | 0 | 0 |
| Intestine | 0 | 0 | 0 | 0 |
| Mesentery | 0 | 0 | 0 | 0 |

TABLE 5-continued

Ephrin type-A receptor 7 scoring on tissue microarray (Biomax, US).

| Tissue | Malignant (%) | | | |
|---|---|---|---|---|
| | + | ++ | +++ | Total |
| Retroperitoneum | 0 | 0 | 0 | 0 |
| Spleen | 0 | 0 | 0 | 0 |

Multiple organ cancer tissue array with normal tissues (+ = weak staining; ++ = moderate staining; +++ = strong staining).

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

Embodiments of the invention are described herein, which comprise certain elements. The invention also extends to separate embodiments consisting of or consisting essentially of the same elements, and vice versa.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

SEQUENCE LISTING

| Sequence | Seq ID |
|---|---|
| MVFQTRYPSWIILCYIWLLRFAHTGEAQAAKEVLLLDSKAQQTELEWISSPPNGWE EISGLDENYTPIRTYQVCQVMEPNQNNWLRTNWISKGNAQRIFVELKFTLRDCNSL PGVLGTCKETFNLYYYETDYDTGRNIRENLYVKIDTIAADESFTQGDLGERKMKLNT EVREIGPLSKKGFYLAFQDVGACIALVSVKVYYKKCWSIIENLAIFPDTVTGSEFSSL VEVRGTCVSSAEEEAENAPRMHCSAEGEWLVPIGKCICKAGYQQKGDTCEPCGR GFYKSSSQDLQCSRCPTHSFSDKEGSSRCECEDGYYRAPSDPPYVACTRPPSAP QNLIFNINQTTVSLEWSPPADNGGRNDVTYRILCKRCSWEQGECVPCGSNIGYMP QQTGLEDNYVTVMDLLAHANYTFEVEAVNGVSDLSRSQRLFAAVSITTGQAAPSQ VSGVMKERVLQRSVELSWQEPEHPNGVITEYEIKYYEKDQRERTYSTVKTKSTSAS INNLKPGTVYVFQIRAFTAAGYGNYSPRLDVATLEEATGKMFEATAVSSEQNPVIIIA VVAVAGTIILVFMVFGFIIGRRHCGYSKADQEGDEELYFHFKFPGTKTYIDPETYEDP NRAVHQFAKELDASCIKIERVIGAGEFGEVCSGRLKLPGKRDVAVAIKTLKVGYTEK QRRDFLCEASIMGQFDHPNVVHLEGVVTRGKPVMIVIEFMENGALDAFLRKHDGQ FTVIQLVGMLRGIAAGMRYLADMGYVHRDLAARNILVNSNLVCKVSDFGLSRVIED DPEAVYTTTGGKIPVRWTAPEAIQYRKFTSASDVWSYGIVMWEVMSYGERPYWD MSNQDVIKAIEEGYRLPAPMDCPAGLHQLMLDCWQKERAERPKFEQIVGILDKMIR NPNSLKTPLGTCSRPISPLLDQNTPDFTTFCSVGEWLQAIKMERYKDNFTAAGYNS LESVARMTIEDVMSLGITLVGHQKKIMSSIQTMRAQMLHLHGTGIQV | 1 |
| MVFQTRYPSWIILCYIWLLRFAHTGEAQAAKEVLLLDSKAQQTELEWISSPPNGWE EISGLDENYTPIRTYQVCQVMEPNQNNWLRTNWISKGNAQRIFVELKFTLRDCNSL PGVLGTCKETFNLYYYETDYDTGRNIRENLYVKIDTIAADESFTQGDLGERKMKLNT EVREIGPLSKKGFYLAFQDVGACIALVSVKVYYKKCWSIIENLAIFPDTVTGSEFSSL VEVRGTCVSSAEEEAENAPRMHCSAEGEWLVPIGKCICKAGYQQKGDTCEPCGR GFYKSSSQDLQCSRCPTHSFSDKEGSSRCECEDGYYRAPSDPPYVACTRPPSAP QNLIFNINQTTVSLEWSPPADNGGRNDVTYRILCKRCSWEQGECVIDCGSNIGYMP QQTGLEDNYVTVMDLLAHANYTFEVEAVNGVSDLSRSQRLFAAVSITTGQAAPSQ VSGVMKERVLQRSVELSWQEPEHPNGVITEYEIKYYEKDQRERTYSTVKTKSTSAS INNLKPGTVYVFQIRAFTAAGYGNYSPRLDVATLEEATATAVSSEQNPVIIIAVVAVA GTIILVFMVFGFIIGRRHCGYSKADQEGDEELYFHFKFPGTKTYIDPETYEDPNRAV HQFAKELDASCIKIERVIGAGEFGEVCSGRLKLPGKRDVAVAIKTLKVGYTEKQRRD FLCEASIMGQFDHPNVVHLEGVVTRGKPVMIVIEFMENGALDAFLRKHDGQFTVIQ LVGMLRGIAAGMRYLADMGYVHRDLAARNILVNSNLVCKVSDFGLSRVIEDDPEAV YTTTGGKIPVRWTAPEAIQYRKFTSASDVWSYGIVMWEVMSYGERPYWDMSNQD VIKAIEEGYRLPAPMDCPAGLHQLMLDCWQKERAERPKFEQIVGILDKMIRNPNSL KTPLGTCSRPISPLLDQNTPDFTTFCSVGEWLQAIKMERYKDNFTAAGYNSLESVA RMTIEDVMSLGITLVGHQKKIMSSIQTMRAQMLHLHGTGIQV | 2 |
| ADQEGDEELYFHFK | 3 |
| AFTAAGYGNYSPR | 4 |
| AIEEGYR | 5 |
| CPTHSFSDK | 6 |
| HDGQFTVIQLVGMLR | 7 |
| MTIEDVMSLGITLVGHQK | 8 |
| RHCGYSK | 9 |
| VSDFGLSR | 10 |
| WTAPEAIQYR | 11 |

The invention claimed is:

1. A method for treating bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer which comprises administering to a subject in need thereof a therapeutically effective amount of a composition comprising an antibody or antigen-binding fragment thereof, wherein the antibody or antigen-binding fragment thereof is conjugated to a therapeutic moiety, capable of specific binding to Ephrin type-A receptor 7 or a fragment thereof, and a pharmaceutically acceptable diluent or carrier, wherein Ephrin type-A receptor 7 is overexpressed in said cancers.

2. A method for treating bladder cancer, breast cancer, colorectal cancer, gastric cancer, head and neck cancer, kidney cancer, lung cancer, osteosarcoma, pancreatic cancer, prostate cancer, skin cancer, thyroid cancer or uterine cancer, including metastatic cancer which comprises administering to a subject in need thereof a therapeutically effective amount of an antibody or antigen-binding fragment thereof, wherein the antibody or antigen-binding fragment thereof is conjugated to a therapeutic moiety, as defined in claim 1.

3. A method for killing a cell expressing Ephrin type-A receptor 7 with a therapeutic moiety comprising contacting said cell with an antibody or antigen-binding fragment thereof capable of specific binding to Ephrin type-A receptor 7, wherein said antibody or antigen-binding fragment thereof is conjugated to the therapeutic moiety.

4. The method according to claim 1, wherein the therapeutic moiety is a cytotoxic moiety or radioactive isotope.

5. The method according to claim 2, wherein the therapeutic moiety is a cytotoxic moiety or radioactive isotope.

6. The method according to claim 1, wherein the antibody or antigen-binding fragment thereof is selected from a group consisting of an isolated monoclonal antibody, an antigen-binding portion of an isolated monoclonal antibody, an antibody mimetic, a full-length IgG1 antibody isotype, a full-length IgG2 antibody isotype, a full-length IgG3 antibody isotype, a full-length IgG4 antibody isotype, a humanised antibody, a single chain antibody, an immunoconjugate, a defucosylated antibody, and a bispecific antibody.

7. The method according to claim 6, wherein the antigen-binding fragment of the antibody is selected from the group consisting of a domain antibody and an antibody mimetic.

8. The method according to claim 2, wherein the antibody or antigen-binding fragment thereof is selected from a group consisting of an isolated monoclonal antibody, an antigen-binding portion of an isolated monoclonal antibody, an antibody mimetic, a full-length IgG1 antibody isotype, a full-length IgG2 antibody isotype, a full-length IgG3 antibody isotype, a full-length IgG4 antibody isotype, a humanised antibody, a single chain antibody, an immunoconjugate, a defucosylated antibody, and a bispecific antibody.

9. The method according to claim 8, wherein the antigen-binding fragment of the antibody is selected from the group consisting of a domain antibody and an antibody mimetic.

10. The method according to claim 1, wherein the cancer is lung cancer.

11. The method according to claim 2, wherein the cancer is lung cancer.

12. The method according to claim 4, wherein the cancer is lung cancer.

13. The method according to claim 5, wherein the cancer is lung cancer.

* * * * *

SEQUENCE LISTING

<160> NUMBER OF SEQ ID NOS: 11

<210> SEQ ID NO 1
<211> LENGTH: 998
<212> TYPE: PRT
<213> ORGANISM: Homo sapiens

<400> SEQUENCE: 1

Met Val Phe Gln Thr Arg Tyr Pro Ser Trp Ile Ile Leu Cys Tyr Ile
1               5                   10                  15

Trp Leu Leu Arg Phe Ala His Thr Gly Glu Ala Gln Ala Ala Lys Glu
            20                  25                  30

Val Leu Leu Leu Asp Ser Lys Ala Gln Gln Thr Glu Leu Glu Trp Ile
        35                  40                  45

Ser Ser Pro Pro Asn Gly Trp Glu Glu Ile Ser Gly Leu Asp Glu Asn
    50                  55                  60

Tyr Thr Pro Ile Arg Thr Tyr Gln Val Cys Gln Val Met Glu Pro Asn
65                  70                  75                  80

Gln Asn Asn Trp Leu Arg Thr Asn Trp Ile Ser Lys Gly Asn Ala Gln
                85                  90                  95

Arg Ile Phe Val Glu Leu Lys Phe Thr Leu Arg Asp Cys Asn Ser Leu
            100                 105                 110

Pro Gly Val Leu Gly Thr Cys Lys Glu Thr Phe Asn Leu Tyr Tyr Tyr
        115                 120                 125

Ala Asp Glu Ser Phe Thr Gln Gly Asp Leu Gly Glu Arg Lys Met Lys
    130                 135                 140

Leu Asn Thr Glu Val Arg Glu Ile Gly Pro Leu Ser Lys Lys Gly Phe
145                 150                 155                 160

Tyr Leu Ala Phe Gln Asp Val Gly Ala Cys Ile Ala Leu Val Ser Val
                165                 170                 175

Lys Val Glu Thr Asp Tyr Asp Thr Gly Arg Asn Ile Arg Glu Asn Leu
            180                 185                 190

Tyr Val Lys Ile Asp Thr Ile Ala Tyr Tyr Lys Lys Cys Trp Ser Ile
        195                 200                 205

Ile Glu Asn Leu Ala Ile Phe Pro Asp Thr Val Thr Gly Ser Glu Phe
    210                 215                 220

Ser Ser Leu Val Glu Val Arg Gly Thr Cys Val Ser Ser Ala Glu Glu
225                 230                 235                 240

Glu Ala Glu Asn Ala Pro Arg Met His Cys Ser Ala Glu Gly Glu Trp
                245                 250                 255

Leu Val Pro Ile Gly Lys Cys Ile Cys Lys Ala Gly Tyr Gln Gln Lys
            260                 265                 270

Gly Asp Thr Cys Glu Pro Cys Gly Arg Gly Phe Tyr Lys Ser Ser Ser
        275                 280                 285

Gln Asp Leu Gln Cys Ser Arg Cys Pro Thr His Ser Phe Ser Asp Lys
    290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                325                 330                 335

Asn Leu Ile Phe Asn Ile Asn Gln Thr Thr Val Ser Leu Glu Trp Ser
            340                 345                 350

Pro Pro Ala Asp Asn Gly Gly Arg Asn Asp Val Thr Tyr Arg Ile Leu
        355                 360                 365

-continued

```
Cys Lys Arg Cys Ser Trp Glu Gln Gly Glu Cys Val Pro Cys Gly Ser
        370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                405                 410                 415

Ala Val Asn Gly Val Ser Asp Leu Ser Arg Ser Gln Arg Leu Phe Ala
                420                 425                 430

Ala Val Ser Ile Thr Thr Gly Gln Ala Ala Pro Ser Gln Val Ser Gly
                435                 440                 445

Val Met Lys Glu Arg Val Leu Gln Arg Ser Val Glu Leu Ser Trp Gln
        450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Val Lys Thr Lys
                485                 490                 495

Ser Thr Ser Ala Ser Ile Asn Asn Leu Lys Pro Gly Thr Val Tyr Val
                500                 505                 510

Phe Gln Ile Arg Ala Phe Thr Ala Ala Gly Tyr Gly Asn Tyr Ser Pro
        515                 520                 525

Arg Leu Asp Val Ala Thr Leu Glu Glu Ala Thr Gly Lys Met Phe Glu
        530                 535                 540

Ala Thr Ala Val Ser Ser Glu Gln Asn Pro Val Ile Ile Ala Val
545                 550                 555                 560

Val Ala Val Ala Gly Thr Ile Ile Leu Val Phe Met Val Phe Gly Phe
                565                 570                 575

Ile Ile Gly Arg Arg His Cys Gly Tyr Ser Lys Ala Asp Gln Glu Gly
                580                 585                 590

Asp Glu Glu Leu Tyr Phe His Phe Lys Phe Pro Gly Thr Lys Thr Tyr
                595                 600                 605

Ile Asp Pro Glu Thr Tyr Glu Asp Pro Asn Arg Ala Val His Gln Phe
        610                 615                 620

Ala Lys Glu Leu Asp Ala Ser Cys Ile Lys Ile Glu Arg Val Ile Gly
625                 630                 635                 640

Ala Gly Glu Phe Gly Glu Val Cys Ser Gly Arg Leu Lys Leu Pro Gly
                645                 650                 655

Lys Arg Asp Val Ala Val Ala Ile Lys Thr Leu Lys Val Gly Tyr Thr
        660                 665                 670

Glu Lys Gln Arg Arg Asp Phe Leu Cys Glu Ala Ser Ile Met Gly Gln
        675                 680                 685

Phe Asp His Pro Asn Val Val His Leu Glu Gly Val Val Thr Arg Gly
        690                 695                 700

Lys Pro Val Met Ile Val Ile Glu Phe Met Glu Asn Gly Ala Leu Asp
705                 710                 715                 720

Ala Phe Leu Arg Lys His Asp Gly Gln Phe Thr Val Ile Gln Leu Val
                725                 730                 735

Gly Met Leu Arg Gly Ile Ala Ala Gly Met Arg Tyr Leu Ala Asp Met
                740                 745                 750

Gly Tyr Val His Arg Asp Leu Ala Ala Arg Asn Ile Leu Val Asn Ser
                755                 760                 765

Asn Leu Val Cys Lys Val Ser Asp Phe Gly Leu Ser Arg Val Ile Glu
770                 775                 780

Asp Asp Pro Glu Ala Val Tyr Thr Thr Thr Gly Gly Lys Ile Pro Val
```

```
                785                 790                 795                 800
Arg Trp Thr Ala Pro Glu Ala Ile Gln Tyr Arg Lys Phe Thr Ser Ala
                    805                 810                 815
Ser Asp Val Trp Ser Tyr Gly Ile Val Met Trp Glu Val Met Ser Tyr
                820                 825                 830
Gly Glu Arg Pro Tyr Trp Asp Met Ser Asn Gln Asp Val Ile Lys Ala
            835                 840                 845
Ile Glu Glu Gly Tyr Arg Leu Pro Ala Pro Met Asp Cys Pro Ala Gly
        850                 855                 860
Leu His Gln Leu Met Leu Asp Cys Trp Gln Lys Glu Arg Ala Glu Arg
865                 870                 875                 880
Pro Lys Phe Glu Gln Ile Val Gly Ile Leu Asp Lys Met Ile Arg Asn
                885                 890                 895
Pro Asn Ser Leu Lys Thr Pro Leu Gly Thr Cys Ser Arg Pro Ile Ser
                900                 905                 910
Pro Leu Leu Asp Gln Asn Thr Pro Asp Phe Thr Thr Phe Cys Ser Val
                915                 920                 925
Gly Glu Trp Leu Gln Ala Ile Lys Met Glu Arg Tyr Lys Asp Asn Phe
        930                 935                 940
Thr Ala Ala Gly Tyr Asn Ser Leu Glu Ser Val Ala Arg Met Thr Ile
945                 950                 955                 960
Glu Asp Val Met Ser Leu Gly Ile Thr Leu Val Gly His Gln Lys Lys
                965                 970                 975
Ile Met Ser Ser Ile Gln Thr Met Arg Ala Gln Met Leu His Leu His
                980                 985                 990
Gly Thr Gly Ile Gln Val
        995

<210> SEQ ID NO 2
<211> LENGTH: 993
<212> TYPE: PRT
<213> ORGANISM: Homo sapiens

<400> SEQUENCE: 2

Met Val Phe Gln Thr Arg Tyr Pro Ser Trp Ile Ile Leu Cys Tyr Ile
1               5                   10                  15
Trp Leu Leu Arg Phe Ala His Thr Gly Glu Ala Gln Ala Ala Lys Glu
                20                  25                  30
Val Leu Leu Leu Asp Ser Lys Ala Gln Gln Thr Glu Leu Glu Trp Ile
            35                  40                  45
Ser Ser Pro Pro Asn Gly Trp Glu Glu Ile Ser Gly Leu Asp Glu Asn
        50                  55                  60
Tyr Thr Pro Ile Arg Thr Tyr Gln Val Cys Gln Val Met Glu Pro Asn
65                  70                  75                  80
Gln Asn Asn Trp Leu Arg Thr Asn Trp Ile Ser Lys Gly Asn Ala Gln
                85                  90                  95
Arg Ile Phe Val Glu Leu Lys Phe Thr Leu Arg Asp Cys Asn Ser Leu
                100                 105                 110
Pro Gly Val Leu Gly Thr Cys Lys Glu Thr Phe Asn Leu Tyr Tyr Tyr
            115                 120                 125
Glu Thr Asp Tyr Asp Thr Gly Arg Asn Ile Arg Glu Asn Leu Tyr Val
        130                 135                 140
Lys Ile Asp Thr Ile Ala Ala Asp Glu Ser Phe Thr Gln Gly Asp Leu
145                 150                 155                 160
Gly Glu Arg Lys Met Lys Leu Asn Thr Glu Val Arg Glu Ile Gly Pro
```

```
                        165                 170                 175
Leu Ser Lys Lys Gly Phe Tyr Leu Ala Phe Gln Asp Val Gly Ala Cys
            180                 185                 190

Ile Ala Leu Val Ser Val Lys Val Tyr Tyr Lys Lys Cys Trp Ser Ile
            195                 200                 205

Ile Glu Asn Leu Ala Ile Phe Pro Asp Thr Val Thr Gly Ser Glu Phe
            210                 215                 220

Ser Ser Leu Val Glu Val Arg Gly Thr Cys Val Ser Ala Glu Glu
225                 230                 235                 240

Glu Ala Glu Asn Ala Pro Arg Met His Cys Ser Ala Glu Gly Glu Trp
                245                 250                 255

Leu Val Pro Ile Gly Lys Cys Ile Cys Lys Ala Gly Tyr Gln Gln Lys
            260                 265                 270

Gly Asp Thr Cys Glu Pro Cys Gly Arg Gly Phe Tyr Lys Ser Ser Ser
            275                 280                 285

Gln Asp Leu Gln Cys Ser Arg Cys Pro Thr His Ser Phe Ser Asp Lys
            290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                325                 330                 335

Asn Leu Ile Phe Asn Ile Asn Gln Thr Thr Val Ser Leu Glu Trp Ser
            340                 345                 350

Pro Pro Ala Asp Asn Gly Gly Arg Asn Asp Val Thr Tyr Arg Ile Leu
            355                 360                 365

Cys Lys Arg Cys Ser Trp Glu Gln Gly Glu Cys Val Pro Cys Gly Ser
            370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                405                 410                 415

Ala Val Asn Gly Val Ser Asp Leu Ser Arg Ser Gln Arg Leu Phe Ala
            420                 425                 430

Ala Val Ser Ile Thr Thr Gly Gln Ala Ala Pro Ser Gln Val Ser Gly
            435                 440                 445

Val Met Lys Glu Arg Val Leu Gln Arg Ser Val Glu Leu Ser Trp Gln
450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Val Lys Thr Lys
                485                 490                 495

Ser Thr Ser Ala Ser Ile Asn Asn Leu Lys Pro Gly Thr Val Tyr Val
            500                 505                 510

Phe Gln Ile Arg Ala Phe Thr Ala Ala Gly Tyr Gly Asn Tyr Ser Pro
            515                 520                 525

Arg Leu Asp Val Ala Thr Leu Glu Glu Ala Thr Ala Thr Ala Val Ser
            530                 535                 540

Ser Glu Gln Asn Pro Val Ile Ile Ala Val Val Ala Val Ala Gly
545                 550                 555                 560

Thr Ile Ile Leu Val Phe Met Val Phe Gly Phe Ile Ile Gly Arg Arg
                565                 570                 575

His Cys Gly Tyr Ser Lys Ala Asp Gln Glu Gly Asp Glu Glu Leu Tyr
            580                 585                 590
```

```
Phe His Phe Lys Phe Pro Gly Thr Lys Thr Tyr Ile Asp Pro Glu Thr
            595                 600                 605
Tyr Glu Asp Pro Asn Arg Ala Val His Gln Phe Ala Lys Glu Leu Asp
    610                 615                 620
Ala Ser Cys Ile Lys Ile Glu Arg Val Ile Gly Ala Glu Phe Gly
625                 630                 635                 640
Glu Val Cys Ser Gly Arg Leu Lys Leu Pro Gly Lys Arg Asp Val Ala
                645                 650                 655
Val Ala Ile Lys Thr Leu Lys Val Gly Tyr Thr Glu Lys Gln Arg Arg
                660                 665                 670
Asp Phe Leu Cys Glu Ala Ser Ile Met Gly Gln Phe Asp His Pro Asn
        675                 680                 685
Val Val His Leu Glu Gly Val Val Thr Arg Gly Lys Pro Val Met Ile
        690                 695                 700
Val Ile Glu Phe Met Glu Asn Gly Ala Leu Asp Ala Phe Leu Arg Lys
705                 710                 715                 720
His Asp Gly Gln Phe Thr Val Ile Gln Leu Val Gly Met Leu Arg Gly
                725                 730                 735
Ile Ala Ala Gly Met Arg Tyr Leu Ala Asp Met Gly Tyr Val His Arg
                740                 745                 750
Asp Leu Ala Ala Arg Asn Ile Leu Val Asn Ser Asn Leu Val Cys Lys
        755                 760                 765
Val Ser Asp Phe Gly Leu Ser Arg Val Ile Glu Asp Asp Pro Glu Ala
770                 775                 780
Val Tyr Thr Thr Thr Gly Gly Lys Ile Pro Val Arg Trp Thr Ala Pro
785                 790                 795                 800
Glu Ala Ile Gln Tyr Arg Lys Phe Thr Ser Ala Ser Asp Val Trp Ser
                805                 810                 815
Tyr Gly Ile Val Met Trp Glu Val Met Ser Tyr Gly Glu Arg Pro Tyr
                820                 825                 830
Trp Asp Met Ser Asn Gln Asp Val Ile Lys Ala Ile Glu Glu Gly Tyr
        835                 840                 845
Arg Leu Pro Ala Pro Met Asp Cys Pro Ala Gly Leu His Gln Leu Met
850                 855                 860
Leu Asp Cys Trp Gln Lys Glu Arg Ala Glu Arg Pro Lys Phe Glu Gln
865                 870                 875                 880
Ile Val Gly Ile Leu Asp Lys Met Ile Arg Asn Pro Asn Ser Leu Lys
                885                 890                 895
Thr Pro Leu Gly Thr Cys Ser Arg Pro Ile Ser Pro Leu Leu Asp Gln
                900                 905                 910
Asn Thr Pro Asp Phe Thr Thr Phe Cys Ser Val Gly Glu Trp Leu Gln
        915                 920                 925
Ala Ile Lys Met Glu Arg Tyr Lys Asp Asn Phe Thr Ala Ala Gly Tyr
930                 935                 940
Asn Ser Leu Glu Ser Val Ala Arg Met Thr Ile Glu Asp Val Met Ser
945                 950                 955                 960
Leu Gly Ile Thr Leu Val Gly His Gln Lys Lys Ile Met Ser Ser Ile
                965                 970                 975
Gln Thr Met Arg Ala Gln Met Leu His Leu His Gly Thr Gly Ile Gln
                980                 985                 990
Val

<210> SEQ ID NO 3
<211> LENGTH: 14
```

```
<212> TYPE: PRT
<213> ORGANISM: Homo sapiens

<400> SEQUENCE: 3

Ala Asp Gln Glu Gly Asp Glu Glu Leu Tyr Phe His Phe Lys
1               5                   10

<210> SEQ ID NO 4
<211> LENGTH: 13
<212> TYPE: PRT
<213> ORGANISM: Homo sapiens

<400> SEQUENCE: 4

Ala Phe Thr Ala Ala Gly Tyr Gly Asn Tyr Ser Pro Arg
1               5                   10

<210> SEQ ID NO 5
<211> LENGTH: 7
<212> TYPE: PRT
<213> ORGANISM: Homo sapiens

<400> SEQUENCE: 5

Ala Ile Glu Glu Gly Tyr Arg
1               5

<210> SEQ ID NO 6
<211> LENGTH: 9
<212> TYPE: PRT
<213> ORGANISM: Homo sapiens

<400> SEQUENCE: 6

Cys Pro Thr His Ser Phe Ser Asp Lys
1               5

<210> SEQ ID NO 7
<211> LENGTH: 15
<212> TYPE: PRT
<213> ORGANISM: Homo sapiens

<400> SEQUENCE: 7

His Asp Gly Gln Phe Thr Val Ile Gln Leu Val Gly Met Leu Arg
1               5                   10                  15

<210> SEQ ID NO 8
<211> LENGTH: 18
<212> TYPE: PRT
<213> ORGANISM: Homo sapiens

<400> SEQUENCE: 8

Met Thr Ile Glu Asp Val Met Ser Leu Gly Ile Thr Leu Val Gly His
1               5                   10                  15

Gln Lys

<210> SEQ ID NO 9
<211> LENGTH: 7
<212> TYPE: PRT
<213> ORGANISM: Homo sapiens

<400> SEQUENCE: 9

Arg His Cys Gly Tyr Ser Lys
1               5

<210> SEQ ID NO 10
<211> LENGTH: 8
<212> TYPE: PRT
```

```
<213> ORGANISM: Homo sapiens

<400> SEQUENCE: 10

Val Ser Asp Phe Gly Leu Ser Arg
1               5

<210> SEQ ID NO 11
<211> LENGTH: 10
<212> TYPE: PRT
<213> ORGANISM: Homo sapiens

<400> SEQUENCE: 11

Trp Thr Ala Pro Glu Ala Ile Gln Tyr Arg
1               5                   10
```